US011725194B2

(12) United States Patent
Boden et al.

(10) Patent No.: US 11,725,194 B2
(45) Date of Patent: *Aug. 15, 2023

(54) HEPATITIS B VIRUS (HBV) VACCINES AND USES THEREOF

(71) Applicant: Janssen Sciences Ireland Unlimited Company, County Cork (IE)

(72) Inventors: Daniel Boden, San Mateo, CA (US); Helen Horton, Mol (BE); Jean-Marc Edmond Fernand Marie Neefs, Lier (BE); Soumitra Roy, Townsend, DE (US)

(73) Assignee: JANSSEN SCIENCES IRELAND UNLIMITED COMPANY

( * ) Notice: Subject to any disclaimer, the term of this patent is extended or adjusted under 35 U.S.C. 154(b) by 164 days.

This patent is subject to a terminal disclaimer.

(21) Appl. No.: 17/324,494

(22) Filed: May 19, 2021

(65) Prior Publication Data

US 2021/0269778 A1  Sep. 2, 2021

Related U.S. Application Data

(63) Continuation of application No. 16/223,251, filed on Dec. 18, 2018, now Pat. No. 11,021,692.

(60) Provisional application No. 62/607,426, filed on Dec. 19, 2017.

(51) Int. Cl.
  *C12N 9/12* (2006.01)
  *A61K 39/12* (2006.01)
  *A61P 31/20* (2006.01)
  *C07K 14/005* (2006.01)
  *A61K 39/00* (2006.01)

(52) U.S. Cl.
  CPC .............. *C12N 9/12* (2013.01); *A61K 39/12* (2013.01); *A61P 31/20* (2018.01); *C07K 14/005* (2013.01); *A61K 39/00* (2013.01); *A61K 2039/5256* (2013.01); *A61K 2039/53* (2013.01); *C12N 2710/10343* (2013.01); *C12N 2730/10122* (2013.01); *C12N 2730/10134* (2013.01)

(58) Field of Classification Search
  None
  See application file for complete search history.

(56) References Cited

U.S. PATENT DOCUMENTS

| 4,522,811 A | 6/1985 | Eppstein |
| 4,727,138 A | 2/1988 | Goeddel |
| 4,738,927 A | 4/1988 | Taniguchi |
| 4,762,791 A | 8/1988 | Goeddel |
| 4,810,643 A | 3/1989 | Souza |
| 4,892,743 A | 1/1990 | Leibowitz |
| 4,966,843 A | 10/1990 | McCormick |
| 4,999,291 A | 3/1991 | Souza |
| 5,017,691 A | 5/1991 | Lee |
| 5,116,742 A | 5/1992 | Cech |
| 5,225,337 A | 7/1993 | Robertson |
| 5,246,921 A | 9/1993 | Reddy |
| 5,273,525 A | 12/1993 | Hofmann |
| 5,780,036 A * | 7/1998 | Chisari ............... A61P 31/12 424/193.1 |
| 5,873,849 A | 2/1999 | Bernard |
| 5,958,060 A | 9/1999 | Premerlani |
| 6,041,252 A | 3/2000 | Walker |
| 6,110,161 A | 8/2000 | Mathiesen |
| 6,117,660 A | 9/2000 | Walters |
| 6,224,879 B1 | 5/2001 | Sjoeberg |
| 6,261,281 B1 | 7/2001 | Mathiesen |
| 6,273,525 B1 | 8/2001 | Erban |
| 6,278,895 B1 | 8/2001 | Bernard |
| 6,319,901 B1 | 11/2001 | Bernard |
| 6,697,669 B2 | 2/2004 | Dev |
| 6,873,549 B2 | 3/2005 | Khalid |
| 6,873,849 B2 | 3/2005 | De La Red |
| 6,912,417 B1 | 6/2005 | Bernard |
| 6,939,862 B2 | 9/2005 | Bureau |
| 6,958,060 B2 | 10/2005 | Mathiesen |
| 6,982,087 B2 | 1/2006 | Johnston |
| 7,328,064 B2 | 2/2008 | Mathiesen |
| 7,419,674 B2 | 9/2008 | Chulay |
| 7,664,545 B2 | 2/2010 | Westersten |
| 7,850,977 B2 | 12/2010 | Kamrud |
| 8,080,255 B2 | 12/2011 | Smith |
| 8,187,249 B2 | 5/2012 | Bernard |
| 8,209,006 B2 | 6/2012 | Smith |
| 8,216,589 B2 * | 7/2012 | Yum ................. A61P 31/20 435/69.3 |
| 8,809,293 B2 | 8/2014 | Chin |
| 8,859,198 B2 * | 10/2014 | Bartholomeusz ...... C12Q 1/706 435/5 |

(Continued)

FOREIGN PATENT DOCUMENTS

JP  H10500017  1/1998
WO  8502862  7/1985

(Continued)

OTHER PUBLICATIONS

Araujo, Natalia M. et al. "Expression of Hepatitis B Virus Surface Antigen (HBsAg) from Genotypes A, D and F and Influence of Amino Acid Variations Related or Not to Genotypes on HBsAg Detection," The Brazilian Journal of Infectious Diseases, vol. 13, issue 4, pp. 266-271 (Aug. 13, 2009).

(Continued)

*Primary Examiner* — Agnieszka Boesen
(74) *Attorney, Agent, or Firm* — Ice Miller LLP

(57) ABSTRACT

Polynucleotides encoding hepatitis B virus (HBV) core antigen and polymerase antigen, and related combinations are described. Also described are vectors, such as DNA plasmids or viral vectors, expressing the HBV core and polymerase antigens, and immunogenic compositions containing the expression vectors. Methods of inducing an immune response against HBV or treating a HBV-induced disease, particularly in individuals having chronic HBV infection, using the immunogenic compositions are also described.

25 Claims, 8 Drawing Sheets

Specification includes a Sequence Listing.

(56) References Cited

U.S. PATENT DOCUMENTS

| | | |
|---|---|---|
| 8,961,995 B2 | 2/2015 | Frolov |
| 9,364,664 B2 | 6/2016 | Masterson |
| 9,452,285 B2 | 9/2016 | Draghia-Akli |
| 9,801,897 B2 | 10/2017 | Geall |
| 9,802,035 B2 | 10/2017 | Masterson |
| 10,538,786 B2 | 1/2020 | Kamrud |
| 10,780,108 B2 | 9/2020 | Li |
| 11,020,476 B2 | 6/2021 | Boden |
| 11,021,692 B2 * | 6/2021 | Boden .................. C07K 14/005 |
| 11,185,688 B2 | 11/2021 | Hannaman |
| 2004/0213805 A1 | 10/2004 | Verheije |
| 2004/0235133 A1 | 11/2004 | Frolov |
| 2005/0070700 A1 | 3/2005 | Giese |
| 2005/0277605 A1 | 12/2005 | Wu |
| 2008/0279891 A1 | 11/2008 | Johnston |
| 2009/0018031 A1 | 1/2009 | Trinklein |
| 2009/0075384 A1 | 3/2009 | Kamrud |
| 2011/0110974 A1 | 5/2011 | Depla |
| 2012/0078161 A1 | 3/2012 | Masterson |
| 2012/0121650 A1 | 5/2012 | Johnston |
| 2014/0079734 A1 | 3/2014 | Frolov |
| 2014/0222105 A1 | 8/2014 | Broderick |
| 2015/0328404 A1 | 11/2015 | Murakami |
| 2016/0074500 A1 | 3/2016 | Pushko |
| 2016/0166678 A1 | 6/2016 | Kallen |
| 2016/0362472 A1 | 12/2016 | Bitter |
| 2017/0314043 A1 | 11/2017 | Kamrud |
| 2018/0104359 A1 | 4/2018 | Kamrud |
| 2018/0171340 A1 | 6/2018 | Kamrud |
| 2018/0285285 A1 | 10/2018 | Carnevale |
| 2019/0163936 A1 | 5/2019 | Pedrone |
| 2020/0164062 A1 | 5/2020 | Goh |
| 2021/0269778 A1 | 9/2021 | Boden |
| 2022/0305107 A1 | 9/2022 | Horton |
| 2022/0305117 A1 | 9/2022 | Horton |

FOREIGN PATENT DOCUMENTS

| | | |
|---|---|---|
| WO | 8504188 | 9/1985 |
| WO | 9006370 | 6/1990 |
| WO | 9503777 A1 | 2/1995 |
| WO | 9531565 | 11/1995 |
| WO | 9637616 | 11/1996 |
| WO | 2000053722 | 9/2000 |
| WO | 0138358 | 5/2001 |
| WO | 200224224 A2 | 3/2002 |
| WO | 2002042480 A2 | 5/2002 |
| WO | 02062959 | 8/2002 |
| WO | 2004055161 A2 | 7/2004 |
| WO | 2005007196 | 1/2005 |
| WO | 2005087311 A1 | 9/2005 |
| WO | 2008020656 | 2/2008 |
| WO | 2008022309 | 2/2008 |
| WO | 2008093976 A1 | 8/2008 |
| WO | 2011015656 A2 | 2/2011 |
| WO | 2011104169 | 9/2011 |
| WO | 2012006376 | 1/2012 |
| WO | 2012083185 | 6/2012 |
| WO | 2012087983 A1 | 6/2012 |
| WO | 2012109668 A1 | 8/2012 |
| WO | 2013003520 | 1/2013 |
| WO | 2013007772 A1 | 1/2013 |
| WO | 2014170493 A2 | 10/2014 |
| WO | 2016020538 A1 | 2/2016 |
| WO | 2016054003 A1 | 4/2016 |
| WO | 2016075250 | 5/2016 |
| WO | 2016184822 A1 | 11/2016 |
| WO | 2016198531 | 12/2016 |
| WO | 2017024000 A1 | 2/2017 |
| WO | 2017076988 | 5/2017 |
| WO | 2017172838 A1 | 10/2017 |
| WO | 2017176319 A1 | 10/2017 |
| WO | 2017180770 A1 | 10/2017 |
| WO | 2018027106 A2 | 2/2018 |
| WO | 2018075235 A1 | 4/2018 |
| WO | 2018106615 A1 | 6/2018 |
| WO | 2018189522 | 10/2018 |
| WO | 2018199338 | 11/2018 |
| WO | 2018225731 A1 | 12/2018 |
| WO | 2019040102 | 2/2019 |
| WO | 2019051257 | 3/2019 |
| WO | 2019099624 A1 | 5/2019 |
| WO | 2019123250 | 6/2019 |
| WO | 2019123252 A1 | 6/2019 |
| WO | 2019126120 | 6/2019 |
| WO | 2020076775 | 4/2020 |
| WO | 2020163747 A1 | 8/2020 |
| WO | 2020255007 | 12/2020 |
| WO | 2020255008 | 12/2020 |
| WO | 2022008613 | 1/2022 |
| WO | 2022133230 | 6/2022 |

OTHER PUBLICATIONS

B. Niedre-Otomere et al, "Recombinant Semliki Forest virus vectors encoding hepatitis B virus small surface and pre-S1 antigens induce broadly reactive neutralizing antibodies : Semliki forest virus vector encoding HBV surface proteins", Journal of Viral Hepatitis, Oxford, UK, (May 17, 2012), vol. 19, No. 9, doi:10.1111/i.1365-2893.2012.01594.x, ISSN 1352-0504, pp. 664-673, XP055491418.

C. Wooddell et al, "Development of subcutaneously administered RNAi therapeutic ARO-HBV for chronic hepatitis B virus infection", Journal of Hepatology, Amsterdam, NL, (Apr. 12, 2018), vol. 68, doi:10.1016/S0168-8278(18)30255-1, ISSN 0168-8278, pp. S18-S19, XP055691743.

Soriano Vicente et al, "Advances in hepatitis B therapeutics", Therapeutic Advances in Infectious Disease Jun. 2016, vol. 7, doi:10.1177/2049936120965027, ISSN 2049-9361, (Oct. 15, 2020), URL: http://journals.sagepub.com/doi/full-xml/10.1177/2049936120965027, XP055905796.

Disterer, Petra, "To (Hep)B or not to (Hep)B?—Oligonucleotide Therapeutics Society", Oligonucleotide Therapeutics Society, (May 23, 2018), URL: https://www.oligotherapeutics.org/to-hepb-or-not-to-hepb/, (May 5, 2020), XP055691740.

Johansson et al, 2012, Plos One, Intradermal Electroporation of Naked Replicon RNA Elicits Strong Immune Responses, 7(1):e29732.

Horng-Tay Tzeng, et al., "PD-1 Blockage Reverses Immune Dysfunction and Hepatitis B Viral Persistence in a Mouse Animal Model," Plos One, vol. 7, No. 6, 9 pages, Jun. 22, 2012.

Guo Z.S., et al., "PP-023 Enhancing the immune responses of HBsAg-pulsed DC vaccine to hepatitis B virus by booking PD-1:PD-L1 signal," International Journal of Infectious Diseases, International Society for Infectious Diseases, vol. 12, 1 page, Nov. 1, 2008.

Azam Bolhassani, et al., "Polymeric nanoparticles: Potent vectors for vaccine delivery targeting cancer and infectious diseases," Human Vaccines and Immunotherapeutics, vol. 10, No. 2, pp. 321-332, Oct. 15, 2013.

Charles H. Jones, et al., Mannosylated poly(beta-amino esters) for targeted antigen presenting cell immune modulation, Biomaterials, vol. 37, pp. 333-344, Jan. 1, 2015.

Evans, T.G., et al., "The use of Flt3 ligand as an adjuvant for hepatitis B vaccination of healthy adults," Vaccine, vol. 21, No. 3-4, pp. 322-329, Dec. 13, 2002.

Ying Wang, et al., "Immunizations with hepatitis B viral antigens and a TLR7/8 agonist adjuvant induce antigen-specific immune responses in HBV-transgenic mice," International Journal of Infectious Diseases, vol. 29, pp. 31-36, Dec. 1, 2014.

International Search Report for PCT/IB2020/055785, 5 pages.
Written Opinion for PCT/IB2020/055785, 5 pages.

Berge et al., "Pharmaceutical Salts", Journal of Pharmaceutical Sciences, Jan. 1977, vol. 66, No. 1, 19 pages.

De Pooter, Dorien et al. "A Therapeutic Hepatitis B Virus DNA Vaccine Induces Specific Immune Responses in Mice and Non-Human Primates." Vaccines vol. 9,9 969. Aug. 29, 2021.

Erhardt et al., "Response to interferon alfa is hepatitis B virus genotype dependent: genotype A is more sensitive to interferon than genotype D", Gut 2005, 54, 1009-1013.

(56) References Cited

OTHER PUBLICATIONS

Lampertico et al., "EASL 2017 Clinical Practice Guidelines on the management of hepatitis B virus infection", Journal of Hepatology 2017, nol. 67, pp. 370-398.
Lok et al, "Hepatitis B Cure: From Discovery to Regulatory Approval", Hepatology, vol. 66, No. 4, 2017, 18 pages.
Paul et al. "Combination Therapy for Chronic Hepatitis B: Current Indications," Current Hepatitis Rep., 10(2), pp. 98-105 (2011).
Agapov et al., Noncytopathic Sindbis Virus RNA Vectors for Heterologous Gene Expression, Proc. Natl. Acad. Sci., 1998, pp. 12989-12994, vol. 95.
Altmann et al., Cotransfection of ICAM-1 and HLA-DR Reconstitutes Human Antigen-Presenting Cell Function in Mouse L Cells, Nature, 1989, pp. 512-514, vol. 338.
Altschul SF et al., "Basic Local Alignment Search Tool"; J. Mol. Biol. 215:403-410 (1990).
Araujo et al., "Expression of Hepatitis B virus surface antigen (HBsAg) from genotypes A, D and F and influence of amino acid variations related or not to genotypes on HBsAg detection," Brazilian Journal of Infectious Diseases, Jan. 1, 2009, vol. 13, Nr: 4.
Atkins, G, et al. Therapeutic and Prophylactic Applications of Alphavirus Vectors, Expert Reviews in Molecular Medicine, Cambridge University Press, vol. 10, No. 1, pp. 1-18 (2008).
Attwood, T. The Babel of Bioinformatics, Science (2000) vol. 290, No. 5491, pp. 471-473 (Year: 2000).
Baker et al., Protein Structure Predication and Structural Genomics, Science (2001) vol. 294, No. 5540, pp. 93-96 (Year: 2001).
Barbieri et al., Purification and partial characterization of another form of the antiviral protein from the seeds of *Phytolacca americana* L. (pokeweed), Biochem. J., 1982, pp. 55-59, vol. 203.
Barrette-Ng et al., Structure of Arterivirus nsp-4, J. Biol. Chem., 2002, pp. 39960-39966, vol. 277, Issue 42.
Bartenschlager et al., "Expression of the P-protein of the human hepatitis B virus in a vaccinia virus system and detection of the nucleocapsid-associated P-gene product by radiolabelling at newly introduced phosphorylation sites", Nucleic Acids Research, vol. 20, No. 2, pp. 195-202,1992.
Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.
Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.
Berglund, P. et al., Enhancing Immune Response Using Suicidal DNA vaccines,, Nature Biotechnology, vol. 16, pp. 562-565 (1998).
Besnard et al., Selection against expression of the *Escherichia coli* gene gpt in hprt+ mouse teratocarcinoma and hybrid cells, Mol. Cell. Biol., 1987, pp. 4139-4141, vol. 7.
Bolz et al.: "Use of Recombinant Virus Replicon Particles for Vaccination against Mycobacterium ulcerans Disease"; PLoS Negl Trop Dis,, Aug. 14, 2015, vol. 9(8):e0004011., PDF File: p. 1-18.
Boukhebza et al., "Comparative analysis of immunization schedules using a novel adenovirus-based immunotherapeutic targeting hepatitis B in naive and tolerant mouse models" Vaccine, 32(26), pp. 3258-3263, 2014.
Brakenhoff et al., Molecular cloning and expression of hybridoma growth factor in *Escherichia coli*, J. Immunol., Dec. 15, 1987, pp. 4116-4121, vol. 139, Issue 12.
Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.
Calderwood et al., Nucleotide sequence of the Shiga-like toxin genes of *Escherichia coli*, Proc. Natl. Acad. Sci. USA, Jul. 1987, pp. 4364-4368, vol. 84.
Carroll and Collier, Active Site of Pseudomonas aeruginosa Exotoxin A, J. Biol. Chem., 1987, pp. 8707-8711, vol. 262.

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.
Chen et al., The complete primary structure of abrin-a B chain. FEBS Letters, 1992, pp. 115-118, vol. 309.
Cheng, W. et al. Enhancement of Sindbis Virus Self-Replicating RNA Vaccine Potency by Linkage of *Mycobacterium tuberculosis* Heat Shock Protein 70 Gene to an Antigen Gene, Journal of Immunology, vol. 166, pp. 6218-6226 (2001).
Chin et al., Tissue-specific Expression of Hepatic Functions Genetic Aspects, Ann. N.Y. Acad. Sci., Oct. 1986, pp. 120-130, vol. 478.
Cohen et al. "Is chronic hepatitis B being undertreated in the United States?" J. Viral Hepat., 18(6), 377-83,2011.
Collins et al., Primary Amino Acid Sequence of α-Trichosanthin and Molecular Models for Abrin A-chain and α-Trichosanthin, J. Biol. Chem., 1990, pp. 8665-8669, vol. 265.
Coussens et al., Tyrosine kinase receptor with extensive homology to EGF receptor shares chromosomal location with neu oncogene, Science, 1985, pp. 1132-1139, vol. 230.
Davis, N. et al., In Vitro Synthesis of Infectious Venezuelan Equine Encephalitis Virus RNA from a cDNA Clone: Analysis of a Viable Deletion Mutant Virology, vol. 171, pp. 189-204 (1989).
De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.
De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for In Vitro and In Vivo Gene Transfer, Journal of Virology, vol. 70, No. 1, pp. 508-519 (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient-2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.
Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).

(56) References Cited

OTHER PUBLICATIONS

Frolov et al., (Journal of Virology, 1999, p. 3854-3865).
Frolov, I et al., Translation of Sindbis Virus mRNA: analysis of sequences downstream of the initiating AUG codon that enhance translation. Journal of Virology, vol. 70, No. 2, pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).
Frolov, I et al. Cis-acting RNA elements at the 5' end of Sindbis virus genome RNA regulate minus-and plus-strand RNA synthesis, RNO, vol. 7, pp. 1638-1651 (2001).
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
GenBank accession # JX473847, dated Dec. 22, 2012; accessed Apr. 17, 2019, 6 pages.
GenBank: KT121715.1: Accession KT121715, Version KT121715.1. 2015, Sindbis virus isolate Treatmant1_population9, complete genome (Year: 2015).
GenBank: L01443.1 Accession No. L01443, 2004, Venezuelan equine encephalitis virus strain TC-83, complete genome (Year: 2004).
GenBank/NCBI accession No. J02363, dated Oct. 25, 2000; accessed Jul. 16, 2018, 7 pages.
GenBank/NCBI accession No. L01443.1., dated Nov. 17, 2014; accessed Octobers, 2016, 7 pages.
GenBank/NCBI accession No. L04653, dated Jun. 1, 2001; accessed Jul. 16, 2018, 6 pages.
GenBank/NCBI accession No. NC_001449, dated Feb. 10, 2015; accessed Jul. 16, 2018, 7 pages.
GenBank/NCBI accession No. NC_003215, dated Feb. 10, 2015; accessed Jul. 16, 2018, 6 pages.
GenBank/NCBI accession No. U38304; dated Feb. 10, 2015; accessed Jul. 16, 2018, 5 pages.
GenBank/NCBI accession No. U38305, dated Jan. 30, 2016, accessed Jul. 16, 2018, 5 pages.
GenBank/NCBI accession No. X04129, dated Mar. 13, 2001; accessed Jul. 16, 2018, 5 pages.
Gibson et al., Enzymatic assembly of DNA molecules up to several hundred kilobases, Nature Methods, Apr. 12, 2009, pp. 343-345, vol. 6.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75 (2004).
Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).
Grabstein et al., Cloning of a T cell growth factor that interacts with the beta chain of the interleukin-2 receptor. Science, 1994, pp. 965-968, vol. 264.
Hardy, R. et al. Requirements at the 3 End of the Sindbis Virus Genome for Efficient Synthesis of Minus-Strand RNA, Journal of Virology, pp. 4630-4639 (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.

Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Huang et al. Development of a vaccine vector based on a subgenomic replicon of porcine reproductive and respiratory syndrome virus. J Virol Methods. Sep. 2009;160(1-2):22-8. (Year: 2009).
Hyde, J. et al., The 5' and 3' ends of alphavirus RNAs—non-coding is not non-functional, Virus Res., vol. 206, pp. 99-107 (2015).
Int'l Search Report and Written Opinion dated Feb. 14, 2019 in Int'l Application No. PCT/US2018/066157, 19 pages.
Int'l Search Report and Written Opinion dated Mar. 26, 2018 in Int'l Application No. PCT/IB2017058148, 14 pages.
Int'l Search Report and Written Opinion dated Mar. 27, 2019 in Int'l Application No. PCT/IB2018/060257, 15 pages.
Int'l Search Report and Written Opinion dated Apr. 17, 2019 in Int'l Application No. PCT/IB2018/060259, 16 pages.
Int'l Search Report and Written Opinion dated May 22, 2018 in Int'l Application No. PCT/IB2017/058142, 17 pages.
Int'l Search Report and Written Opinion dated Jun. 25, 2018 in Int'l Application No. PCT/US2017/067269, 17 pages.
International Search Report and Written Opinion dated Dec. 13, 2019 in International Appl. No. PCT/US2019/055125, 15 pages.
International Search Report and Written Opinion, dated Dec. 1, 2017, in International Application No. PCT/US2017/054928, 18 pages.
International Search Report and Written Opinion, dated Jul. 10, 2017, in International Patent Application No. PCT/US2017/027249, filed Apr. 12, 2017, 16 pages.
International Search Report and Written Opinion, dated Jul. 3, 2018, in International Application No. PCT/US2017/064561, 22 pages.
International Search Report dated Apr. 23, 2019, regarding PCT/US2019/014210, 13 pages.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Irvin JD, Pokeweed antiviral protein, Pharmac. Ther., 1983, pp. 371-387, vol. 21, Issue 3.
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Jeeva S, Lee JA, Park SY, Song CS, Choi IS, Lee JB. Development of porcine respiratory and reproductive syndrome virus replicon vector for foot-and-mouth disease vaccine. Clin Exp Vaccine Res. Jan. 2014;3(1):100-9. doi: 10.7774/cevr.2014.3.1.100. Epub Dec. 18, 2013. PMID: 24427767; PMCID: PMC3890444. (Year: 2014).
Jones et al., "Hepatitis B virus reverse transcriptase: diverse functions as classical and emerging targets for antiviral intervention", Emerging Microbes and Infections, 2(9), e56, 9 pages, 2013.
Kamrud et al., Alphavirus Replicon Approach to Promoterless Analysis of IRES Elements, Virology, 2007, pp. 376-387, vol. 360.
Karlin & Altschul, Applications and statistics for multiple high-scoring segments in molecular sequences Proc. Nat'l. Acad. Sci. USA 90:5873-87 (1993).
Karupiah et al., Elevated natural killer cell responses in mice infected with recombinant vaccinia virus encoding murine IL-2, J. Immunol., Jan. 1, 1990, pp. 290-298, vol. 144, Issue 1.
Kelly, B. et al. Potential of Alphavirus Vectors in the Treatment of Advanced Solid Tumors, Recent Patents on Anti-Drug Discovery, vol. 2, No. 2, pp. 159-166 (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.

(56) References Cited

OTHER PUBLICATIONS

Kim et al. 2014. Enhancement of protein expression by alphavirus replicons by designing self-replicating subgenomic RNAs. Proceedings National Academy of Sciences, 111 (29):10708-10713.
Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Klimstra et al., Adaptation of Sindbis Virus to BHK Cells Selects for Use of Heparan Sulfate as an Attachment Receptor. J. Virol. 72: pp. 7357 (1988), 10 pages.
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).
Kulasegaran-Shylini et al., The 5'UTR-specific mutation in Veev TC-83 genome has a strong effect on RNA replication and subgenomic RNA synthesis, but not on translation of the encoded proteins. Virology, 387(1): 211-221 (2009).
Lamb et al., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Lundstrom, Kenneth L: "Replicon RNA Viral Vectors as Vaccines"; Vaccines, 2016, vol. 4(4). pii: E39. PDF File: p. 1-23.
Luo, R., et al., Antiviral activity of type I and type III interferons against porcine reproductive and respiratory syndrome virus (PRRSV), Antiviral Research, vol. 91, pp. 99-101 (2011).
Maher and Dolinick, Specific hybridization arrest of dihydrofolate reductase mRNA in vitro using antisense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.
Maruggi Giulietta et al, "Engineered alphavirus replicon vaccines based on known attenuated viral mutants show limited effects on immunogenicity", Virology, (Oct. 5, 2013), vol. 447, No. 1, doi:10.1016/J.VIROL.2013.07.021, ISSN 0042-6822, pp. 254-264, XP028754361.

McKnight et al., Deduced consensus sequence of Sindbis virus strain AR339: mutations contained in laboratory strains which affect cell culture and in vivo phenotypes. Virol. 70:1981 (1996), 9 pages.
McLoughlin, M. et al. Alphavirus infections in salmonids—a review, Journal of Fish Diseases, vol. 30, pp. 511-531 (2007).
Mekalanos et al., Cholera toxin genes: nucleotide sequence, deletion analysis and vaccine development, Nature, 1983, pp. 551-557, vol. 306.
Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).
Michel et al. "Therapeutic vaccines and immune-based therapies for the treatment of chronic hepatitis B: perspectives and challenges." J. Hepatol., 54(6), 1286-1296, 2011.
Mir et. al. A Multicistronic DNA Vaccine Induces Significant Protection against Tuberculosis in Mice and Offers Flexibility in the Expressed Antigen Repertoire. 2009. Clinical and Vaccine Immunology. vol. 16, No. 10. p. 1467-1475 (Year: 2009).
Mogler, M. et al., RNA-based viral vectors, Expert Rev. Vaccines, pp. 1-30 (2014).
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Molenkamp et al., Isolation and Characterization of an Arterivirus Defective Interfering RNA Genome, J. Virol., 2000, pp. 3156-3165, vol. 74, Issue 7.
Molenkamp R et al, "The arterivirus replicase is the only viral protein required for genome replication and subgenomic mRNA transcription.", The Journal of General Virology Oct. 2000, (Oct. 2000), vol. 81, No. Pt 10, ISSN 0022-1317, pp. 2491-2496, XP002771366.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264 (2013).
Nagata, et al., Synthesis in $E.$ $coli$ of a polypeptide with human leukocyte interferon activity, Nature, 1980, pp. 316-320, vol. 284.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Needleman, S. et al., A general method applicable to the search for similarities in the amino acid sequence of two proteins J. Mol. Biol. 48:443-53 (1970).
Nolz, J et al. Strategies and Implications for Prime-Boost Vaccination to Generate Memory CD8 T Cells, Advances in Experimental Medicine and Biology, pp. 69-83, (2011).
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 352-662, 2013.
Obeng-Adjei et al., "Synthetic DNA immunogen encoding hepatitis B core antigen drives immune response in liver," Cancer Gene Therapy, Nov. 5, 2012 Appleton & Lange, New York, vol. 19, Nr: 11, pp. 779-787.
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Regulation of Relative Abundance of Arterivirus Subgenomic mRNAs, J. Virol., Aug. 2004, pp. 8102-8113, vol. 78, Issue 15.
Pasternak, Sequence requirements for RNA strand transfer during nidovirus discontinuous subgenomic RNA synthesis, EMBO J., 2001, pp. 7220-7228, vol. 20, Issue 24.

(56) References Cited

OTHER PUBLICATIONS

Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pearson, W. et al., Improved tools for biological sequence comparison, Proc. Natl. Acad. Sci. US, vol. 85, pp. 2444-2448 (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Perrine Martin et al, "TG1050, an immunotherapeutic to treat chronic hepatitis B, induces robust T cells and exerts an antiviral effect in HBV-persistent mice", Gut, UK, (Nov. 26, 2014), vol. 64, No. 12, doi:10.1136/gutjnl-2014-308041, ISSN 0017-5749, pp. 1961-1971, XP055453477.
Petrakova et al., Noncytopathic Replication of Venezuelan Equine Encephalitis Virus and Eastern Equine Encephalitis Virus Replicons in Mammalian Cells, Journal of Virology, Jun. 2005, p. 7597-7608.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015.
Ramirez et at., "Biology of Attenuated Modified Vaccinia Virus Ankara Recombinant Vector in Mice: Virus Fate and Activation of B- and T-Cell Immune Responses in Comparision with the Western Reserve Strain and advantages as a Vaccine", Journal of Virology, Vo. 74, No. 2, pp. 923-933, 2000.
Reyes-Sandoval Arturo et al, "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (Jan. 2010), vol. 78, No. 1, pp. 145-153, XP002778539.
Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819 (1987).
Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.
Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009) 147 pages.
Sjoberg,E et al., A Significantly Improved Semliki Forest Virus Expression System Based on Translation Enhancer Segments from the Viral Capsid Gene, Biotechnology, Vo,. 12, pp. 1127-1131, (1994).
Smith et al., Comparison of Biosequences, Adv. Appl. Math., 2:482-89 (1981).
Snijder EJ et al., "Identification of a Novel Structural Protein of Arteriviruses," J. Virol, Aug. 1999, pp. 6335-6345, vol. 37, Issue 8.
Snijder et al., 2005. The order Nidovirales, pp. 390-404, In Topley and Wilson's microbiology and microbial infections, B. W. Mahy and V. ter Meulen (ed.), Hodder Arnold, London, United Kingdom.
Snijder et al., Heterodimerization of the Two Major Envelope Proteins is Essential for Arterivirus Infectivity, J. Virol., 2003, pp. 97-104, vol. 77, Issue 1.
Snijder et al., Proteolytic Processing of the Arterivirus Replicase, 1995, pp. 443-451. In Corona-and Related Viruses, P.J. Talbot and G.A. Levy (ed.), Plenum Press, NY.
Snijder et al., The Arterivirus Nsp2 Protease, J. Biol. Chem., 1995, pp. 16671-16676, vol. 270, Issue 28.
Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.
Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.
Stanton et al., Nucleotide sequence comparison of normal and translocated murine c-myc genes, Nature, Aug. 1984, pp. 423-425, vol. 310.
Stirpe et al., Gelonin, a New Inhibitor of Protein Synthesis, Nontoxic to Intact Cells, J. Biol. Chem., Jul. 25, 1980, pp. 6947-6953, vol. 255.
Strauss et al., The AlpahViruses: Gene Expression, Replication and Evolution, Microbiological Reviews, pp. 491-562, Sep. 1994.
Te Velthuis, et al., Zn2+ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.
Tepper et al., Murine interleukin-4 displays potent anti-tumor activity in vivo, Cell, May 5, 1989, pp. 503-512, vol. 57.
Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.
Tian et al. Arterivirus minor envelope proteins are a major determinant of viral tropism in cell culture. J Virol. Apr. 2012;86(7):3701-12. (Year: 2012).
Tijerina et al., DMS Footprinting of Structured RNAs and RNA-Protein Complexes, Nat. Protoc., 2007, pp. 2608-2623, vol. 2, Issue 10.
Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.
Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.
Toribio et al., An RNA Trapping Mechanism in Alphavirus MRNA Promotes Translation and Initiation Nucleic Acids Res. 19, 44(9): pp. 4368-4380 (2016).
Toribio et al., Inhibition of host translation by virus infection in vivo, PNAS, vol. 107, No. 21, pp. 9837-9842 (2010).

(56) References Cited

OTHER PUBLICATIONS

Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.

Twu et al., Hepatitis B virus X gene can transactivate heterologous viral sequences, Proc Natl. Acad. Sci. USA, Mar. 1989, pp. 2046-2050, vol. 86.

Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.

Van Aken et al., Expression, Purification, and In Vitro Activity of an Arterivirus Main Proteinase, Virus Res., 2006, pp. 97-106, vol. 120.

Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.

Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.

Van Den Born, et al., "An infectious recombinant equine arteritis virus expressing green fluorescent protein from its replicase gene," J. Genl. ViroL, Apr. 2007, pp. 1196-1205, vol. 88.

Van Den Born, Value of routine funduscopy in patients with hypertension: systematic review, BMJ, Jul. 9, 2005, pp. 1-5, vol. 331.

Van Der Meer et al., ORF1a-Encoded Replicase Subunits are Involved in the Membrane Association of the Arterivirus Replication Complex, J. ViroL, 1998, pp. 6689-6698, vol. 72, Issue 8.

Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.

Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.

Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.

Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.

Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.

Van Kasteren et al., Deubiquitinase Function of Arterivirus Papain-Like Protease 2 Suppresses the Innate Immune Response in Infected Host Cells, PNAS, 2013, pp. E838-E847.

Van Marie et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

Van Marie, et al., Characterization of an Equine Arteritis Virus Replicase Mutant Defective in Subgenomic mRNA Synthesis, J. Virol., 1999, pp. 5274-5281, vol. 73, Issue 7.

Ventoso, I. et al. Translational resistance of late alphavirus mRNA to eIF2 phosphorylation: a strategy to overcome the antiviral effect of protein kinase PKR, Genes and Development, vol. 20, pp. 87-100 (2006).

Ventoso, I., Adaptive Changes in Alphavirus mRNA Translation Allowed Colonization of Vertebrate Hosts, Journal of Virology, vol. 86, No. 17, pp. 9484-9494 (2012).

Vrudhula et al., Prodrugs of doxorubicin and melphalan and their activation by a monoclonal antibody-penicillin-G amidase conjugate, J. Med. Chem., 1993, pp. 919-923, vol. 36, Issue 7.

Ward, S. et al., Generation of CTL responses using Kunjin replicon RNA, Immunology and Cell Biology, vol. 81, pp. 73-78 (2003).

Warner et al. Induction of the HIV-Specific and Antibody Responses in Mice Using Retroviral Vector-Transduced Cells, AIDS Res. and Human Retroviruses, vol. 7, No. 8, pp. 645-655 (1991).

Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.

Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.

Weber et al., Immunotherapy of a murine tumor with interleukin 2. J. Exp. Med., 1987, pp. 1716-1733, vol. 166.

White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).

Wilson et al., Prospects for gene therapy of familial hypercholesterolemia, Mol. Biol. Med., Jun. 1, 1990, pp. 223-232, vol. 7, Issue 3.

Wood et al., Preproabrin: genomic cloning, characterisation and the expression of the A-chain in *Escherichia coli*, Eur. J. Biochem., 1991, pp. 723-732, vol. 198.

World Health Organization, Hepatitis B: Fact sheet No. 204 [Internet] Mar. 2015. Available from https://www.who.int/news-room/fact-sheets/detail/hepatitis-b, 6 pages.

Xu et al.: "Type-specific and cross-reactive antibodies induced by human papillomavirus 31 L1/L2 virus-like particle";, J Med Microbiol. 2007, vol. 56(Pt 7), p. 907-13.

Yamamoto et al., The human LDL receptor: a cysteine-rich protein with multiple Alu sequences in its mRNA, Cell, Nov. 1984, pp. 27-38, vol. 39, Issue 1.

Yin et al. Similarities and Differences in Antagonism of Neuron Alpha/Beta and Sindbis Alphaviruses 2009. Journal of Virology. 83 ( 19) p. 10036-10047 (Year: 2009).

Zhou, X. et al. Self-replicating Semliki Forest virus RNA as recombinant vaccine, Vaccine, vol. 12, No. 16, pp. 1510-1514 (1994).

\* cited by examiner

FIG. 2A
FIG. 2B
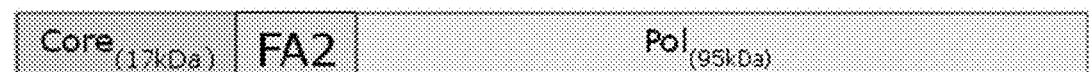
FIG. 2C
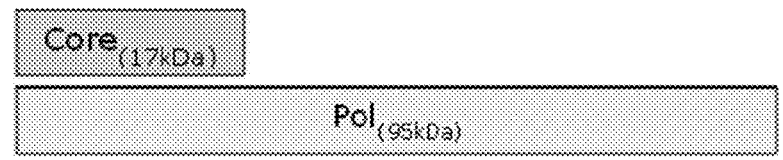
FIG. 2D    FIG. 2E
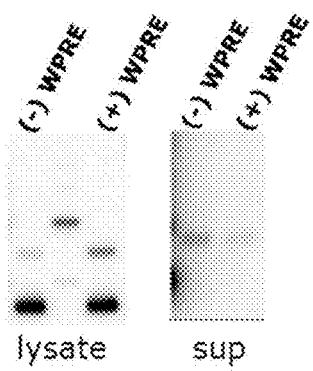 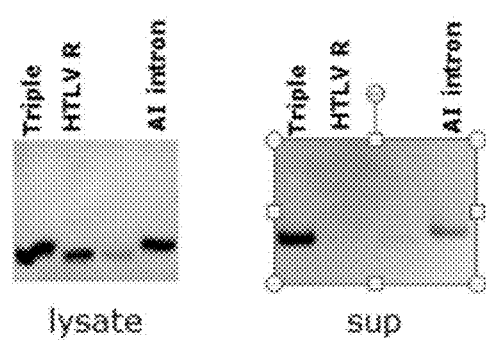
FIG. 2F
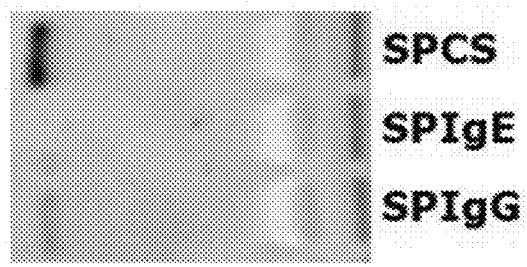

```
                              SEQUENCE LISTING

<160> NUMBER OF SEQ ID NOS: 24

<210> SEQ ID NO 1
<211> LENGTH: 444
<212> TYPE: DNA
<213> ORGANISM: Artificial Sequence
<220> FEATURE:
<223> OTHER INFORMATION: HBV truncated core antigen gene

<400> SEQUENCE: 1
gacatcgacc cttacaagga gttcggcgcc agcgtggaac tgctgtcttt tctgcccagt        60
gatttctttc cttccattcg agacctgctg gataccgcct ctgctctgta tcgggaagcc       120
ctggagagcc agaacactg ctccccacac cataccgctc tgcgacaggc aatcctgtgc       180
tggggggagc tgatgaacct ggccacatgg gtgggatcga atctggagga ccccgcttca       240
cgggaactgg tggtcagcta cgtgaacgtc aatatgggc tgaaaatccg ccagctgctg       300
tggttccata ttagctgcct gactttggga cgagagaccg tgctggaata cctggtgtcc       360
ttcggcgtct ggattcgcac tcccctgct tatcgaccac ccaacgcacc aattctgtcc       420
accctgcccg agaccacagt ggtc                                            444

<210> SEQ ID NO 2
<211> LENGTH: 148
<212> TYPE: PRT
<213> ORGANISM: Artificial Sequence
<220> FEATURE:
<223> OTHER INFORMATION: HBV truncated core antigen

<400> SEQUENCE: 2

Asp Ile Asp Pro Tyr Lys Glu Phe Gly Ala Ser Val Glu Leu Leu Ser
1               5                   10                  15

Phe Leu Pro Ser Asp Phe Phe Pro Ser Ile Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Asn Leu Ala Thr Trp Val Gly Ser Asn Leu Glu Asp Pro Ala Ser
65                  70                  75                  80

Arg Glu Leu Val Val Ser Tyr Val Asn Val Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125
```

Pro Ala Tyr Arg Pro Pro Asn Ala Pro Ile Leu Ser Thr Leu Pro Glu
    130                 135                 140

Thr Thr Val Val
145

<210> SEQ ID NO 3
<211> LENGTH: 2529
<212> TYPE: DNA
<213> ORGANISM: Artificial Sequence
<220> FEATURE:
<223> OTHER INFORMATION: HBV pol antigen gene

<400> SEQUENCE: 3

| | | | | | |
|---|---|---|---|---|---|
| atgcccctgt | cttaccagca | ctttagaaag | cttctgctgc | tggacgatga | agccgggcct | 60 |
| ctggaggaag | agctgccaag | gctggcagac | gaggggctga | accggagagt | ggccgaagat | 120 |
| ctgaatctgg | gaaacctgaa | cgtgagcatc | ccttggactc | ataaagtcgg | caacttcacc | 180 |
| gggctgtaca | gctccacagt | gcctgtcttc | aatccagagt | ggcagacacc | atcctttccc | 240 |
| aacattcacc | tgcaggagga | catcattaat | agatgcgaac | agttcgtggg | acctctgaca | 300 |
| gtcaacgaaa | agaggcgcct | gaaactgatc | atgcctgcca | ggttttaccc | aaatgtgact | 360 |
| aagtatctgc | cactggataa | gggcatcaag | ccttactatc | cagagcacct | ggtgaaccat | 420 |
| tacttccaga | ctagacacta | tctgcatacc | ctgtggaagg | ccggaatcct | gtacaaacga | 480 |
| gaaactaccc | ggagtgcttc | attttgtggc | tccccatatt | cttgggaaca | ggagctgcag | 540 |
| catggcaggc | tggtgttcca | gaccagcaca | cgccacgggg | atgagtcctt | ttgccagcag | 600 |
| tctagtggca | tcctgagcag | atcccccgtg | gggccttgtc | tgcagtctca | gctgcggaag | 660 |
| agtagactgg | gactgcagcc | acagcaggga | cacctggcac | gacggcagca | gggaaggtct | 720 |
| ggcagtatcc | gggctagagt | gcatcccaca | actagaaggc | ctttcggcgt | cgagccatca | 780 |
| ggaagcggcc | acaccacaaa | caccgcatca | agctcctcta | gttgcctgca | tcagtcagcc | 840 |
| gtgagaaagg | ccgcttacag | ccacctgtcc | acatctaaaa | ggcactcaag | ctccgggcat | 900 |
| gctgtggagc | tgcacaacat | ccctccaaat | tctgcacgca | gtcagtcaga | aggacccgtg | 960 |
| ttcagctgct | ggtggctgca | gtttcggaac | tcaaagcctt | gcagcgacta | ttgtctgagc | 1020 |
| catattgtga | atctgctgga | ggattggggc | ccttgtaccg | agcacgggga | acaccatatc | 1080 |
| aggattccac | gaacaccagc | acgagtgact | ggagggggtgt | tcctggtgga | caagaacccc | 1140 |
| cacaatacta | ccgagagccg | gctggtggtc | gatttcagtc | agttttcaag | aggcaacaca | 1200 |
| agggtgtcat | ggcccaaatt | cgccgtccct | aatctgcaga | gtctgactaa | cctgctgtct | 1260 |
| agtaatctga | gctggctgtc | cctggacgtg | tccgcagcct | tttaccacct | gcctctgcat | 1320 |
| ccagctgcaa | tgccccatct | gctggtgggg | tcaagcggac | tgagtcgcta | cgtcgcccga | 1380 |
| ctgtcctcta | actcacgcat | cattaatcac | cagcatggca | ccatgcagaa | cctgcacgat | 1440 |
| agctgttccc | ggaatctgta | cgtgtctctg | ctgctgctgt | ataagacatt | cggcagaaaa | 1500 |
| ctgcacctgt | acagccatcc | tatcattctg | gggtttagga | gatcccaat | gggagtgggaa | 1560 |
| ctgagccccct | tcctgctggc | acagtttacc | tccgccatt | gctctgtggt | ccgccgagcc | 1620 |
| ttcccacact | gtctggcttt | ttcctatatg | aacaatgtgg | tcctgggcgc | caaatccgtg | 1680 |
| cagcatctgg | agtctctgtt | cacagctgtc | actaactttc | tgctgagcct | ggggatccac | 1740 |
| ctgaacccaa | ataagactaa | acgctggggg | tacagcctga | atttcatggg | atatgtgatt | 1800 |
| ggatcctggg | ggaccctgcc | acaggagcac | atcgtgcaga | agatcaagga | atgctttcgg | 1860 |
| aagctgcccg | tcaacagacc | tatcgactgg | aaagtgtgcc | agcggattgt | cggactgctg | 1920 |

```
ggcttcgccg ctcccttac ccagtgcggg tacccagcac tgatgcccct gtatgcctgt    1980
atccagtcta agcaggcttt cacctttagt cctacataca aggcattcct gtgcaaacag    2040
tacctgaacc tgtatccagt ggcaaggcag cgacctggac tgtgccaggt ctttgcaaat    2100
gccactccta ccggctgggg gctggctatc ggacatcagc gaatgcgggg cacattcgtg    2160 gccccctgc ctattcacac tgctcagctg ctggcagcct gctttgctag atctaggagt    2220
ggagcaaagc tgatcggcac cgacaatagt gtggtcctgt caagaaaata cacatccttc    2280
ccatggctgc tgggatgtgc tgcaaactgg attctgaggg gcaccagctt cgtgtacgtc    2340
ccctcagccc tgaatcctgc tgacgatcca tcccgcgggc gactgggact gtaccgacct    2400
ctgctgagac tgcccttcag gcctacaact ggccggacat ctctgtatgc cgattcacca    2460
agcgtgccct cacacctgcc tgacagagtc cactttgctt caccccctgca cgtcgcttgg    2520 cggcctcca                                                             2529
```

<210> SEQ ID NO 4
<211> LENGTH: 843
<212> TYPE: PRT
<213> ORGANISM: Artificial Sequence
<220> FEATURE:
<223> OTHER INFORMATION: HBV pol antigen

<400> SEQUENCE: 4

```
Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

Asn Ile His Leu Gln Glu Asp Ile Ile Asn Arg Cys Glu Gln Phe Val
                85                  90                  95

Gly Pro Leu Thr Val Asn Glu Lys Arg Arg Leu Lys Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Gln Gln Ser Ser Gly Ile Leu Ser Arg Ser
        195                 200                 205

Pro Val Gly Pro Cys Leu Gln Ser Gln Leu Arg Lys Ser Arg Leu Gly
    210                 215                 220

Leu Gln Pro Gln Gln Gly His Leu Ala Arg Gln Gln Gly Arg Ser
225                 230                 235                 240

Gly Ser Ile Arg Ala Arg Val His Pro Thr Thr Arg Arg Pro Phe Gly
                245                 250                 255
```

```
Val Glu Pro Ser Gly Ser Gly His Thr Thr Asn Thr Ala Ser Ser Ser
            260                 265                 270

Ser Ser Cys Leu His Gln Ser Ala Val Arg Lys Ala Ala Tyr Ser His
        275                 280                 285

Leu Ser Thr Ser Lys Arg His Ser Ser Ser Gly His Ala Val Glu Leu
    290                 295                 300

His Asn Ile Pro Pro Asn Ser Ala Arg Ser Gln Ser Glu Gly Pro Val
305                 310                 315                 320

Phe Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His His Ile Arg Ile Pro Arg Thr Pro Ala Arg
                355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
                435                 440                 445

Val Gly Ser Ser Gly Leu Ser Arg Tyr Val Ala Arg Leu Ser Ser Asn
    450                 455                 460

Ser Arg Ile Ile Asn His Gln His Gly Thr Met Gln Asn Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asn Asn Val Val Leu Gly Ala Lys Ser Val
545                 550                 555                 560

Gln His Leu Glu Ser Leu Phe Thr Ala Val Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Glu Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
            660                 665                 670
```

```
Tyr Lys Ala Phe Leu Cys Lys Gln Tyr Leu Asn Leu Tyr Pro Val Ala
            675                 680                 685

Arg Gln Arg Pro Gly Leu Cys Gln Val Phe Ala Asn Ala Thr Pro Thr
        690                 695                 700

Gly Trp Gly Leu Ala Ile Gly His Gln Arg Met Arg Gly Thr Phe Val
705                 710                 715                 720

Ala Pro Leu Pro Ile His Thr Ala Gln Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu Arg Leu Pro Phe Arg Pro Thr Thr Gly Arg Thr Ser Leu Tyr
                805                 810                 815

Ala Asp Ser Pro Ser Val Pro Ser His Leu Pro Asp Arg Val His Phe
            820                 825                 830

Ala Ser Pro Leu His Val Ala Trp Arg Pro Pro
        835                 840
```

<210> SEQ ID NO 5
<211> LENGTH: 63
<212> TYPE: DNA
<213> ORGANISM: Artificial Sequence
<220> FEATURE:
<223> OTHER INFORMATION: Cystatin S signal peptide coding sequence

<400> SEQUENCE: 5

```
atggctcgac ctctgtgtac cctgctactc ctgatggcta ccctggctgg agctctggcc    60
agc                                                                  63
```

<210> SEQ ID NO 6
<211> LENGTH: 21
<212> TYPE: PRT
<213> ORGANISM: Artificial Sequence
<220> FEATURE:
<223> OTHER INFORMATION: Cystatin S signal peptide sequence

<400> SEQUENCE: 6

```
Met Ala Arg Pro Leu Cys Thr Leu Leu Leu Leu Met Ala Thr Leu Ala
1               5                   10                  15

Gly Ala Leu Ala Ser
            20
```

<210> SEQ ID NO 7
<211> LENGTH: 586
<212> TYPE: DNA
<213> ORGANISM: Artificial Sequence
<220> FEATURE:
<223> OTHER INFORMATION: hCMV promoter sequence

<400> SEQUENCE: 7

```
tgacattgat tattgactag ttattaatag taatcaatta cggggtcatt agttcatagc    60
ccatatatgg agttccgcgt tacataactt acggtaaatg gcccgcctgg ctgaccgccc   120
aacgaccccc gcccattgac gtcaataatg acgtatgttc ccatagtaac gccaataggg   180
```

| | |
|---|---|
| actttccatt gacgtcaatg ggtggactat ttacggtaaa ctgcccactt ggcagtacat | 240 |
| caagtgtatc atatgccaag tacgcccct attgacgtca atgacggtaa atggcccgcc | 300 |
| tggcattatg cccagtacat gaccttatgg gactttccta cttggcagta catctacgta | 360 |
| ttagtcatcg ctattaccat ggtgatgcgg ttttggcagt acatcaatgg gcgtggatag | 420 |
| cggtttgact cacggggatt tccaagtctc cacccattg acgtcaatgg gagtttgttt | 480 |
| tggcaccaaa atcaacggga ctttccaaaa tgtcgtaaca actccgcccc attgacgcaa | 540 |
| atgggcggta ggcgtgtacg gtgggaggtc tatataagca gagctc | 586 |

<210> SEQ ID NO 8
<211> LENGTH: 378
<212> TYPE: DNA
<213> ORGANISM: Artificial Sequence
<220> FEATURE:
<223> OTHER INFORMATION: triple enhancer regulatory sequence

<400> SEQUENCE: 8

| | |
|---|---|
| ggctcgcatc tctccttcac gcgcccgccg ccctacctga ggccgccatc cacgccggtt | 60 |
| gagtcgcgtt ctgccgcctc ccgcctgtgg tgcctcctga actgcgtccg ccgtctaggt | 120 |
| aagtttaaag ctcaggtcga gaccgggcct ttgtccggcg ctcccttgga gcctacctag | 180 |
| actcagccgg ctctccacgc tttgcctgac cctgcttgct caactctagt tctctcgtta | 240 |
| acttaatgag acagatagaa actggtcttg tagaaacaga gtagtcgcct gcttttctgc | 300 |
| caggtgctga cttctctccc ctgggctttt ttcttttct caggttgaaa agaagaagac | 360 |
| gaagaagacg aagaagac | 378 |

<210> SEQ ID NO 9
<211> LENGTH: 99
<212> TYPE: DNA
<213> ORGANISM: Artificial Sequence
<220> FEATURE:
<223> OTHER INFORMATION: Bla promoter sequence

<400> SEQUENCE: 9

| | |
|---|---|
| acccctattt gtttattttt ctaaatacat tcaaatatgt atccgctcat gagacaataa | 60 |
| ccctgataaa tgcttcaata atattgaaaa aggaagagt | 99 |

<210> SEQ ID NO 10
<211> LENGTH: 671
<212> TYPE: DNA
<213> ORGANISM: Artificial Sequence
<220> FEATURE:
<223> OTHER INFORMATION: pUC ori sequence

<400> SEQUENCE: 10

| | |
|---|---|
| cccgtagaaa agatcaaagg atcttcttga gatccttttt ttctgcgcgt aatctgctgc | 60 |
| ttgcaaacaa aaaaaccgct accagcggtg gtttgtttgc cggatcaaga gctaccaact | 120 |
| ctttttccga aggtaactgg cttcagcaga gcgcagatac caaatactgt tcttctagtg | 180 |
| tagccgtagt taggccacca cttcaagaac tctgtagcac cgcctacata cctcgctctg | 240 |
| ctaatcctgt taccagtggc tgctgccagt ggcgataagt cgtgtcttac cgggttggac | 300 |
| tcaagacgat agttaccgga taaggcgcag cggtcgggct gaacggggg ttcgtgcaca | 360 |
| cagcccagct tggagcgaac gacctacacc gaactgagat acctacagcg tgagctatga | 420 |
| gaaagcgcca cgcttcccga agggagaaag gcggacaggt atccggtaag cggcagggtc | 480 |
| ggaacaggag agcgcacgag ggagcttcca gggggaaacg cctggtatct ttatagtcct | 540 |

```
gtcgggtttc gccacctctg acttgagcgt cgattttttgt gatgctcgtc aggggggcgg      600
agcctatgga aaaacgccag caacgcggcc ttttttacggt tcctggcctt ttgctggcct      660
tttgctcaca t                                                            671

<210> SEQ ID NO 11
<211> LENGTH: 225
<212> TYPE: DNA
<213> ORGANISM: Artificial Sequence
<220> FEATURE:
<223> OTHER INFORMATION: bGH polyadenylation signal sequence

<400> SEQUENCE: 11
ctgtgccttc tagttgccag ccatctgttg tttgccccctc ccccgtgcct tccttgaccc       60
tggaaggtgc cactcccact gtcctttcct aataaaatga ggaaattgca tcgcattgtc      120
tgagtaggtg tcattctatt ctggggggtg ggtggggca ggacagcaag ggggaggatt       180
gggaagacaa tagcaggcat gctggggatg cggtgggctc tatgg                      225

<210> SEQ ID NO 12
<211> LENGTH: 795
<212> TYPE: DNA
<213> ORGANISM: Artificial Sequence
<220> FEATURE:
<223> OTHER INFORMATION: Kan R gene

<400> SEQUENCE: 12
atgattgagc aagatggtct tcacgctggc tcgccagctg cgtgggtgga acgcctgttt       60
ggttatgatt gggcgcagca gactattgga tgttccgacg cggctgtatt tcggctgtct      120
gctcagggtc gccccgtgct gtttgtgaag acggatttgt ctggcgcatt aaatgagtta      180
caggacgagg cggctcgtct gagttggttg gccaccaccg gcgtgccctg cgccgcagtg      240
ctggatgtcg tgacagaagc aggccgcgat tggctccttc tcggcgaagt gccgggccag      300
gacctgctca gcagccactt ggcaccggca gaaaaagttt ctatcatggc cgacgccatg      360
cgtcgtcttc acactctcga tccggccacg tgcccctttg accaccaggc caagcatcgt      420
attgaacgtg cgcgtactcg gatggaagca ggtttagtag accaggacga tttggatgag      480
gaacatcaag gcctggcccc ggctgaactg tttgcgcgct aaaagcgtc gatgccagat       540 ggcgaagatt tggtagtcac ccatggagat gcgtgtttgc aaacatcat ggttgaaaat       600 ggccgcttct caggctttat tgactgtggg cgcctgggtg ttgccgaccg ctatcaagat      660
attgcgctcg caactcgtga catcgctgaa gagctgggcg gagaatgggc tgaccgtttc      720
ctggtactgt atggcattgc agcgcccgat tcccaacgca tcgcatttta tcgtctgctg      780
gatgagtttt tctaa                                                       795

<210> SEQ ID NO 13
<211> LENGTH: 264
<212> TYPE: PRT
<213> ORGANISM: Artificial Sequence
<220> FEATURE:
<223> OTHER INFORMATION: Kan R protein

<400> SEQUENCE: 13

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30
```

```
Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                     85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
                115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
                195                 200                 205

Cys Gly Arg Leu Gly Val Ala Asp Arg Tyr Gln Asp Ile Ala Leu Ala
                210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
                260

<210> SEQ ID NO 14
<211> LENGTH: 149
<212> TYPE: PRT
<213> ORGANISM: Artificial Sequence
<220> FEATURE:
<223> OTHER INFORMATION: HBV truncated core antigen

<400> SEQUENCE: 14

Met Asp Ile Asp Pro Tyr Lys Glu Phe Gly Ala Ser Val Glu Leu Leu
  1               5                  10                  15

Ser Phe Leu Pro Ser Asp Phe Phe Pro Ser Ile Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125
```

Pro Pro Ala Tyr Arg Pro Pro Asn Ala Pro Ile Leu Ser Thr Leu Pro
    130                 135                 140

Glu Thr Thr Val Val
145

<210> SEQ ID NO 15
<211> LENGTH: 447
<212> TYPE: DNA
<213> ORGANISM: Artificial Sequence
<220> FEATURE:
<223> OTHER INFORMATION: HBV truncated core antigen gene

<400> SEQUENCE: 15

```
atggacatcg acccttacaa ggagttcggc gccagcgtgg aactgctgtc tttctgccc      60 agtgatttct tccttccat tcgagacctg ctggataccg cctctgctct gtatcgggaa     120
gccctggaga gcccagaaca ctgctcccca caccataccg ctctgcgaca ggcaatcctg    180
tgctgggggg agctgatgaa cctggccaca tgggtgggat ccaatctgga ggaccccgct    240
tcacgggaac tggtggtcag ctacgtgaac gtcaatatgg gcctgaaaat ccgccagctg    300
ctgtggttcc atattagctg cctgactttt ggacgagaga ccgtgctgga atacctggtg    360
tccttcggcg tctggatccg cactcccct gcttatcgac cacccaacgc accaattctg     420
tccaccctgc ccgagaccac agtggtc                                        447
```

<210> SEQ ID NO 16
<211> LENGTH: 2529
<212> TYPE: DNA
<213> ORGANISM: Artificial Sequence
<220> FEATURE:
<223> OTHER INFORMATION: HBV pol antigen gene

<400> SEQUENCE: 16

```
atgccctgt cttaccagca ctttagaaag ctgctgctgc tggacgatga agccgggcct      60
ctggaggaag agctgccaag gctggcagac gaggggctga accggagagt ggccgaagat    120
ctgaatctgg gaaacctgaa cgtgagcatc ccttggactc ataaagtcgg caacttcacc    180
gggctgtaca gctccacagt gcctgtcttc aatccagagt ggcagacacc atcctttccc    240
aacattcacc tgcaggagga catcattaat agatgcgaac agttcgtggg acctctgaca    300
gtcaacgaaa agaggcgcct gaaactgatc atgcctgcca ggttttaccc aaatgtgact    360
aagtatctgc cactggataa gggcatcaag ccttactatc cagagcacct ggtgaaccat    420
tacttccaga ctagcactta ctgcataccc tgtggaaggc cggaatcct gtacaaacga     480 gaaactaccc ggagtgcttc attttgtggc tccccatatt cttgggaaca ggagctgcag    540
catggcaggc tggtgttcca gaccagcaca cgccacgggg atgagtcctt ttgccagcag    600
tctagtggca tcctgagcag atcccccgtg gggccttgtc tgcagtctca gctgcggaag    660
agtagactgg gactgcagcc acagcaggga cacctggcac gacggcagca gggaaggtct    720
ggcagtatcc gggctagagt gcatcccaca actagaaggc ctttcggcgt cgagccatca    780
ggaagcggcc acaccacaaa caccgcatca agctcctcta gttgcctgca tcagtcagcc    840
gtgagaaagg ccgcttacag ccacctgtcc acatctaaaa ggcactcaag ctccgggcat    900
gctgtggagc tgcacaacat ccctccaaat tctgcacgca gtcagtcaga aggacccgtg    960
ttcagctgct ggtggctgca gtttcggaac tcaaagcctt gcagcgacta ttgtctgagc   1020
catattgtga atctgctgga ggattgggc ccttgtaccg agcacgggga acaccatatc    1080
aggattccac gaacaccagc acgagtgact ggaggggtgt cctggtgga caagaacccc   1140
```

| | |
|---|---|
| cacaatacta ccgagagccg gctggtggtc gatttcagtc agttttcaag aggcaacaca | 1200 |
| agggtgtcat ggcccaaatt cgccgtccct aatctgcaga gtctgactaa cctgctgtct | 1260 |
| agtaatctga gctggctgtc cctggacgtg tccgcagcct tttaccacct gcctctgcat | 1320 |
| ccagctgcaa tgccccatct gctggtgggg tcaagcggac tgagtcgcta cgtcgcccga | 1380 |
| ctgtcctcta actcacgcat cattaatcac cagcatggca ccatgcagaa cctgcacgat | 1440 |
| agctgttccc ggaatctgta cgtgtctctg ctgctgctgt ataagacatt cggcagaaaa | 1500 |
| ctgcacctgt acagccatcc tatcattctg gggtttagga agatcccaat gggagtggga | 1560 |
| ctgagcccct tcctgctggc acagtttacc tccgccattt gctctgtggt ccgccgagcc | 1620 |
| ttcccacact gtctggcttt ttcctatatg aacaatgtgg tcctgggcgc caaatccgtg | 1680 |
| cagcatctgg agtctctgtt cacagctgtc actaactttc tgctgagcct ggggatccac | 1740 |
| ctgaacccaa ataagactaa cgctggggg tacagcctga atttcatggg atatgtgatt | 1800 |
| ggatcctggg ggaccctgcc acaggagcac atcgtgcaga agatcaagga atgctttcgg | 1860 |
| aagctgcccg tcaacagacc tatcgactgg aaagtgtgcc agcggattgt cggactgctg | 1920 |
| ggcttcgccg ctccctttac ccagtgcggg tacccagcac tgatgcccct gtatgcctgt | 1980 |
| atccagtcta gcaggctttt cacctttagt cctacataca aggcattcct gtgcaaacag | 2040 |
| tacctgaacc tgtatccagt ggcaaggcag cgacctggac tgtgccaggt cttttgcaaat | 2100 |
| gccactccta ccggctgggg gctggctatc ggacatcagc gaatgcgggg cacattcgtg | 2160 |
| gccccctgc ctattcacac tgctcagctg ctggcagcct gctttgctag atctaggagt | 2220 |
| ggagcaaagc tgatcggcac cgacaatagt gtggtcctgt caagaaaata cacatccttc | 2280 |
| ccatggctgc tgggatgtgc tgcaaactgg attctgaggg gcaccagctt cgtgtacgtc | 2340 |
| ccctcagccc tgaatcctgc tgacgatcca tcccgcgggc gactgggact gtaccgacct | 2400 |
| ctgctgagac tgcccttcag gcctacaact ggccggacat ctctgtatgc cgattccacca | 2460 |
| agcgtgccct cacacctgcc tgacagagtc cactttgctt caccccctgca cgtcgcttgg | 2520 |
| cggcctcca | 2529 |

<210> SEQ ID NO 17
<211> LENGTH: 684
<212> TYPE: DNA
<213> ORGANISM: Artificial Sequence
<220> FEATURE:
<223> OTHER INFORMATION: hCMV promoter sequence

<400> SEQUENCE: 17

| | |
|---|---|
| accgccatgt tgacattgat tattgactag ttattaatag taatcaatta cggggtcatt | 60 |
| agttcatagc ccatatatgg agttccgcgt tacataactt acggtaaatg gcccgcctgg | 120 |
| ctgaccgccc aacgaccccc gcccattgac gtcaataatg acgtatgttc ccatagtaac | 180 |
| gccaataggg actttccatt gacgtcaatg ggtggagtat ttacggtaaa ctgcccactt | 240 |
| ggcagtacat caagtgtatc atatgccaag tacgccccct attgacgtca atgacggtaa | 300 |
| atggcccgcc tggcattatg cccagtacat gaccttatgg gactttccta cttggcagta | 360 |
| catctacgta ttagtcatcg ctattaccat ggtgatgcgg ttttggcagt acatcaatgg | 420 |
| gcgtggatag cggtttgact cacggggatt tccaagtctc cacccattg acgtcaatgg | 480 |
| gagtttgttt tggcaccaaa atcaacggga ctttccaaaa tgtcgtaaca actccgcccc | 540 |
| attgacgcaa atgggcggta ggcgtgtacg gtgggaggtc tatataagca gagctcgttt | 600 |

```
agtgaaccgt cagatcgcct ggagacgcca tccacgctgt tttgacctcc atagaagaca    660
ccgggaccga tccagcctcc gcgg                                           684
```

<210> SEQ ID NO 18
<211> LENGTH: 81
<212> TYPE: DNA
<213> ORGANISM: Artificial Sequence
<220> FEATURE:
<223> OTHER INFORMATION: immunoglobulin secretion signal coding sequence

<400> SEQUENCE: 18

```
atggagttcg gcctgtcttg ggtctttctg gtggcaatcc tgaagggcgt gcagtgtgaa    60
gtgcagctgc tggagtctgg a                                              81
```

<210> SEQ ID NO 19
<211> LENGTH: 27
<212> TYPE: PRT
<213> ORGANISM: Artificial Sequence
<220> FEATURE:
<223> OTHER INFORMATION: immunoglobulin secretion signal sequence

<400> SEQUENCE: 19

Met Glu Phe Gly Leu Ser Trp Val Phe Leu Val Ala Ile Leu Lys Gly
1               5                   10                  15

Val Gln Cys Glu Val Gln Leu Leu Glu Ser Gly
            20                  25

<210> SEQ ID NO 20
<211> LENGTH: 996
<212> TYPE: PRT
<213> ORGANISM: Artificial Sequence
<220> FEATURE:
<223> OTHER INFORMATION: HBV core-pol fusion antigen sequence

<400> SEQUENCE: 20

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Ala Gly Ala Gly Met Pro Leu Ser Tyr Gln His
145                 150                 155                 160

Phe Arg Lys Leu Leu Leu Leu Asp Asp Glu Ala Gly Pro Leu Glu Glu
                165                 170                 175

Glu Leu Pro Arg Leu Ala Asp Glu Gly Leu Asn Arg Arg Val Ala Glu
            180                 185                 190

```
Asp Leu Asn Leu Gly Asn Leu Asn Val Ser Ile Pro Trp Thr His Lys
            195                 200                 205

Val Gly Asn Phe Thr Gly Leu Tyr Ser Ser Thr Val Pro Val Phe Asn
    210                 215                 220

Pro Glu Trp Gln Thr Pro Ser Phe Pro Asn Ile His Leu Gln Glu Asp
225                 230                 235                 240

Ile Ile Asn Arg Cys Glu Gln Phe Val Gly Pro Leu Thr Val Asn Glu
                245                 250                 255

Lys Arg Arg Leu Lys Leu Ile Met Pro Ala Arg Phe Tyr Pro Asn Val
            260                 265                 270

Thr Lys Tyr Leu Pro Leu Asp Lys Gly Ile Lys Pro Tyr Tyr Pro Glu
        275                 280                 285

His Leu Val Asn His Tyr Phe Gln Thr Arg His Tyr Leu His Thr Leu
    290                 295                 300

Trp Lys Ala Gly Ile Leu Tyr Lys Arg Glu Thr Thr Arg Ser Ala Ser
305                 310                 315                 320

Phe Cys Gly Ser Pro Tyr Ser Trp Glu Gln Glu Leu Gln His Gly Arg
                325                 330                 335

Leu Val Phe Gln Thr Ser Thr Arg His Gly Asp Glu Ser Phe Cys Gln
            340                 345                 350

Gln Ser Ser Gly Ile Leu Ser Arg Ser Pro Val Gly Pro Cys Leu Gln
        355                 360                 365

Ser Gln Leu Arg Lys Ser Arg Leu Gly Leu Gln Pro Gln Gln Gly His
    370                 375                 380

Leu Ala Arg Arg Gln Gln Gly Arg Ser Gly Ser Ile Arg Ala Arg Val
385                 390                 395                 400

His Pro Thr Thr Arg Arg Pro Phe Gly Val Glu Pro Ser Gly Ser Gly
                405                 410                 415

His Thr Thr Asn Thr Ala Ser Ser Ser Ser Cys Leu His Gln Ser
            420                 425                 430

Ala Val Arg Lys Ala Ala Tyr Ser His Leu Ser Thr Ser Lys Arg His
        435                 440                 445

Ser Ser Ser Gly His Ala Val Glu Leu His Asn Ile Pro Pro Asn Ser
    450                 455                 460

Ala Arg Ser Gln Ser Glu Gly Pro Val Phe Ser Cys Trp Trp Leu Gln
465                 470                 475                 480

Phe Arg Asn Ser Lys Pro Cys Ser Asp Tyr Cys Leu Ser His Ile Val
                485                 490                 495

Asn Leu Leu Glu Asp Trp Gly Pro Cys Thr Glu His Gly Glu His His
            500                 505                 510

Ile Arg Ile Pro Arg Thr Pro Ala Arg Val Thr Gly Gly Val Phe Leu
        515                 520                 525

Val Asp Lys Asn Pro His Asn Thr Thr Glu Ser Arg Leu Val Val Asp
    530                 535                 540

Phe Ser Gln Phe Ser Arg Gly Asn Thr Arg Val Ser Trp Pro Lys Phe
545                 550                 555                 560

Ala Val Pro Asn Leu Gln Ser Leu Thr Asn Leu Leu Ser Ser Asn Leu
                565                 570                 575

Ser Trp Leu Ser Leu Asp Val Ser Ala Ala Phe Tyr His Leu Pro Leu
            580                 585                 590

His Pro Ala Ala Met Pro His Leu Leu Val Gly Ser Ser Gly Leu Ser
        595                 600                 605
```

```
Arg Tyr Val Ala Arg Leu Ser Ser Asn Ser Arg Ile Ile Asn His Gln
    610                 615                 620

His Gly Thr Met Gln Asn Leu His Asp Ser Cys Ser Arg Asn Leu Tyr
625                 630                 635                 640

Val Ser Leu Leu Leu Leu Tyr Lys Thr Phe Gly Arg Lys Leu His Leu
                645                 650                 655

Tyr Ser His Pro Ile Ile Leu Gly Phe Arg Lys Ile Pro Met Gly Val
            660                 665                 670

Gly Leu Ser Pro Phe Leu Leu Ala Gln Phe Thr Ser Ala Ile Cys Ser
            675                 680                 685

Val Val Arg Arg Ala Phe Pro His Cys Leu Ala Phe Ser Tyr Met Asn
690                 695                 700

Asn Val Val Leu Gly Ala Lys Ser Val Gln His Leu Glu Ser Leu Phe
705                 710                 715                 720

Thr Ala Val Thr Asn Phe Leu Leu Ser Leu Gly Ile His Leu Asn Pro
                725                 730                 735

Asn Lys Thr Lys Arg Trp Gly Tyr Ser Leu Asn Phe Met Gly Tyr Val
            740                 745                 750

Ile Gly Ser Trp Gly Thr Leu Pro Gln Glu His Ile Val Gln Lys Ile
            755                 760                 765

Lys Glu Cys Phe Arg Lys Leu Pro Val Asn Arg Pro Ile Asp Trp Lys
    770                 775                 780

Val Cys Gln Arg Ile Val Gly Leu Leu Gly Phe Ala Ala Pro Phe Thr
785                 790                 795                 800

Gln Cys Gly Tyr Pro Ala Leu Met Pro Leu Tyr Ala Cys Ile Gln Ser
                805                 810                 815

Lys Gln Ala Phe Thr Phe Ser Pro Thr Tyr Lys Ala Phe Leu Cys Lys
            820                 825                 830

Gln Tyr Leu Asn Leu Tyr Pro Val Ala Arg Gln Arg Pro Gly Leu Cys
            835                 840                 845

Gln Val Phe Ala Asn Ala Thr Pro Thr Gly Trp Gly Leu Ala Ile Gly
    850                 855                 860

His Gln Arg Met Arg Gly Thr Phe Val Ala Pro Leu Pro Ile His Thr
865                 870                 875                 880

Ala Gln Leu Leu Ala Ala Cys Phe Ala Arg Ser Arg Ser Gly Ala Lys
                885                 890                 895

Leu Ile Gly Thr Asp Asn Ser Val Val Leu Ser Arg Lys Tyr Thr Ser
            900                 905                 910

Phe Pro Trp Leu Leu Gly Cys Ala Ala Asn Trp Ile Leu Arg Gly Thr
            915                 920                 925

Ser Phe Val Tyr Val Pro Ser Ala Leu Asn Pro Ala Asp Asp Pro Ser
    930                 935                 940

Arg Gly Arg Leu Gly Leu Tyr Arg Pro Leu Leu Arg Leu Pro Phe Arg
945                 950                 955                 960

Pro Thr Thr Gly Arg Thr Ser Leu Tyr Ala Asp Ser Pro Ser Val Pro
                965                 970                 975

Ser His Leu Pro Asp Arg Val His Phe Ala Ser Pro Leu His Val Ala
            980                 985                 990

Trp Arg Pro Pro
        995
```

```
<210> SEQ ID NO 21
<211> LENGTH: 1023
<212> TYPE: PRT
<213> ORGANISM: Artificial Sequence
<220> FEATURE:
<223> OTHER INFORMATION: HBV core-pol fusion antigen sequence with Ig
      signal sequence

<400> SEQUENCE: 21
```

| | | | | | | | | | | | | | | |
|---|---|---|---|---|---|---|---|---|---|---|---|---|---|---|
| Met | Glu | Phe | Gly | Leu | Ser | Trp | Val | Phe | Leu | Val | Ala | Ile | Leu | Lys | Gly |
| 1 | | | | 5 | | | | | 10 | | | | | 15 | |

| | | | | | | | | | | | | | |
|---|---|---|---|---|---|---|---|---|---|---|---|---|---|
| Val | Gln | Cys | Glu | Val | Gln | Leu | Leu | Glu | Ser | Gly | Met | Asp | Ile | Asp | Pro |
| | | 20 | | | | | 25 | | | | | 30 | |

| Tyr | Lys | Glu | Phe | Gly | Ala | Ser | Val | Glu | Leu | Leu | Ser | Phe | Leu | Pro | Ser |
| | | | 35 | | | | | 40 | | | | | 45 | |

| Asp | Phe | Phe | Pro | Ser | Ile | Arg | Asp | Leu | Leu | Asp | Thr | Ala | Ser | Ala | Leu |
| | 50 | | | | | 55 | | | | | 60 | |

| Tyr | Arg | Glu | Ala | Leu | Glu | Ser | Pro | Glu | His | Cys | Ser | Pro | His | His | Thr |
| 65 | | | | | 70 | | | | | 75 | | | | | 80 |

| Ala | Leu | Arg | Gln | Ala | Ile | Leu | Cys | Trp | Gly | Glu | Leu | Met | Asn | Leu | Ala |
| | | | | 85 | | | | | 90 | | | | | 95 | |

| Thr | Trp | Val | Gly | Ser | Asn | Leu | Glu | Asp | Pro | Ala | Ser | Arg | Glu | Leu | Val |
| | | | | 100 | | | | | 105 | | | | | 110 | |

| Val | Ser | Tyr | Val | Asn | Val | Asn | Met | Gly | Leu | Lys | Ile | Arg | Gln | Leu | Leu |
| | | | 115 | | | | | 120 | | | | | 125 | | |

| Trp | Phe | His | Ile | Ser | Cys | Leu | Thr | Phe | Gly | Arg | Glu | Thr | Val | Leu | Glu |
| | 130 | | | | | 135 | | | | | 140 | | |

| Tyr | Leu | Val | Ser | Phe | Gly | Val | Trp | Ile | Arg | Thr | Pro | Pro | Ala | Tyr | Arg |
| 145 | | | | | 150 | | | | | 155 | | | | | 160 |

| Pro | Pro | Asn | Ala | Pro | Ile | Leu | Ser | Thr | Leu | Pro | Glu | Thr | Thr | Val | Val |
| | | | | 165 | | | | | 170 | | | | | 175 | |

| Ala | Gly | Ala | Gly | Met | Pro | Leu | Ser | Tyr | Gln | His | Phe | Arg | Lys | Leu | Leu |
| | | | | 180 | | | | | 185 | | | | | 190 | |

| Leu | Leu | Asp | Asp | Glu | Ala | Gly | Pro | Leu | Glu | Glu | Leu | Pro | Arg | Leu |
| | | | 195 | | | | | 200 | | | | | 205 | |

| Ala | Asp | Glu | Gly | Leu | Asn | Arg | Arg | Val | Ala | Glu | Asp | Leu | Asn | Leu | Gly |
| | 210 | | | | | 215 | | | | | 220 | |

| Asn | Leu | Asn | Val | Ser | Ile | Pro | Trp | Thr | His | Lys | Val | Gly | Asn | Phe | Thr |
| 225 | | | | | 230 | | | | | 235 | | | | | 240 |

| Gly | Leu | Tyr | Ser | Ser | Thr | Val | Pro | Val | Phe | Asn | Pro | Glu | Trp | Gln | Thr |
| | | | | 245 | | | | | 250 | | | | | 255 | |

| Pro | Ser | Phe | Pro | Asn | Ile | His | Leu | Gln | Glu | Asp | Ile | Ile | Asn | Arg | Cys |
| | | | 260 | | | | | 265 | | | | | 270 | | |

| Glu | Gln | Phe | Val | Gly | Pro | Leu | Thr | Val | Asn | Glu | Lys | Arg | Arg | Leu | Lys |
| | | 275 | | | | | 280 | | | | | 285 | | |

| Leu | Ile | Met | Pro | Ala | Arg | Phe | Tyr | Pro | Asn | Val | Thr | Lys | Tyr | Leu | Pro |
| | | 290 | | | | | 295 | | | | | 300 | | |

| Leu | Asp | Lys | Gly | Ile | Lys | Pro | Tyr | Tyr | Pro | Glu | His | Leu | Val | Asn | His |
| 305 | | | | | 310 | | | | | 315 | | | | | 320 |

| Tyr | Phe | Gln | Thr | Arg | His | Tyr | Leu | His | Thr | Leu | Trp | Lys | Ala | Gly | Ile |
| | | | 325 | | | | | 330 | | | | | 335 | | |

| Leu | Tyr | Lys | Arg | Glu | Thr | Thr | Arg | Ser | Ala | Ser | Phe | Cys | Gly | Ser | Pro |
| | | | 340 | | | | | 345 | | | | | 350 | | |

| Tyr | Ser | Trp | Glu | Gln | Glu | Leu | Gln | His | Gly | Arg | Leu | Val | Phe | Gln | Thr |
| | | | 355 | | | | | 360 | | | | | 365 | | |

```
Ser Thr Arg His Gly Asp Glu Ser Phe Cys Gln Gln Ser Ser Gly Ile
370                 375                 380

Leu Ser Arg Ser Pro Val Gly Pro Cys Leu Gln Ser Gln Leu Arg Lys
385                 390                 395                 400

Ser Arg Leu Gly Leu Gln Pro Gln Gln Gly His Leu Ala Arg Arg Gln
            405                 410                 415

Gln Gly Arg Ser Gly Ser Ile Arg Ala Arg Val His Pro Thr Thr Arg
            420                 425                 430

Arg Pro Phe Gly Val Glu Pro Ser Gly Ser Gly His Thr Thr Asn Thr
        435                 440                 445

Ala Ser Ser Ser Ser Cys Leu His Gln Ser Ala Val Arg Lys Ala
450                 455                 460

Ala Tyr Ser His Leu Ser Thr Ser Lys Arg His Ser Ser Ser Gly His
465                 470                 475                 480

Ala Val Glu Leu His Asn Ile Pro Pro Asn Ser Ala Arg Ser Gln Ser
                485                 490                 495

Glu Gly Pro Val Phe Ser Cys Trp Trp Leu Gln Phe Arg Asn Ser Lys
                500                 505                 510

Pro Cys Ser Asp Tyr Cys Leu Ser His Ile Val Asn Leu Leu Glu Asp
            515                 520                 525

Trp Gly Pro Cys Thr Glu His Gly Glu His His Ile Arg Ile Pro Arg
530                 535                 540

Thr Pro Ala Arg Val Thr Gly Gly Val Phe Leu Val Asp Lys Asn Pro
545                 550                 555                 560

His Asn Thr Thr Glu Ser Arg Leu Val Val Asp Phe Ser Gln Phe Ser
            565                 570                 575

Arg Gly Asn Thr Arg Val Ser Trp Pro Lys Phe Ala Val Pro Asn Leu
            580                 585                 590

Gln Ser Leu Thr Asn Leu Leu Ser Ser Asn Leu Ser Trp Leu Ser Leu
        595                 600                 605

Asp Val Ser Ala Ala Phe Tyr His Leu Pro Leu His Pro Ala Ala Met
610                 615                 620

Pro His Leu Leu Val Gly Ser Ser Gly Leu Ser Arg Tyr Val Ala Arg
625                 630                 635                 640

Leu Ser Ser Asn Ser Arg Ile Ile Asn His Gln His Gly Thr Met Gln
            645                 650                 655

Asn Leu His Asp Ser Cys Ser Arg Asn Leu Tyr Val Ser Leu Leu Leu
            660                 665                 670

Leu Tyr Lys Thr Phe Gly Arg Lys Leu His Leu Tyr Ser His Pro Ile
        675                 680                 685

Ile Leu Gly Phe Arg Lys Ile Pro Met Gly Val Gly Leu Ser Pro Phe
690                 695                 700

Leu Leu Ala Gln Phe Thr Ser Ala Ile Cys Ser Val Val Arg Arg Ala
705                 710                 715                 720

Phe Pro His Cys Leu Ala Phe Ser Tyr Met Asn Asn Val Val Leu Gly
            725                 730                 735

Ala Lys Ser Val Gln His Leu Glu Ser Leu Phe Thr Ala Val Thr Asn
            740                 745                 750

Phe Leu Leu Ser Leu Gly Ile His Leu Asn Pro Asn Lys Thr Lys Arg
        755                 760                 765

Trp Gly Tyr Ser Leu Asn Phe Met Gly Tyr Val Ile Gly Ser Trp Gly
770                 775                 780
```

```
Thr Leu Pro Gln Glu His Ile Val Gln Lys Ile Lys Glu Cys Phe Arg
785                 790                 795                 800

Lys Leu Pro Val Asn Arg Pro Ile Asp Trp Lys Val Cys Gln Arg Ile
            805                 810                 815

Val Gly Leu Leu Gly Phe Ala Ala Pro Phe Thr Gln Cys Gly Tyr Pro
        820                 825                 830

Ala Leu Met Pro Leu Tyr Ala Cys Ile Gln Ser Lys Gln Ala Phe Thr
    835                 840                 845

Phe Ser Pro Thr Tyr Lys Ala Phe Leu Cys Lys Gln Tyr Leu Asn Leu
850                 855                 860

Tyr Pro Val Ala Arg Gln Arg Pro Gly Leu Cys Gln Val Phe Ala Asn
865                 870                 875                 880

Ala Thr Pro Thr Gly Trp Gly Leu Ala Ile Gly His Gln Arg Met Arg
            885                 890                 895

Gly Thr Phe Val Ala Pro Leu Pro Ile His Thr Ala Gln Leu Leu Ala
        900                 905                 910

Ala Cys Phe Ala Arg Ser Arg Ser Gly Ala Lys Leu Ile Gly Thr Asp
    915                 920                 925

Asn Ser Val Val Leu Ser Arg Lys Tyr Thr Ser Phe Pro Trp Leu Leu
930                 935                 940

Gly Cys Ala Ala Asn Trp Ile Leu Arg Gly Thr Ser Phe Val Tyr Val
945                 950                 955                 960

Pro Ser Ala Leu Asn Pro Ala Asp Asp Pro Ser Arg Gly Arg Leu Gly
            965                 970                 975

Leu Tyr Arg Pro Leu Leu Arg Leu Pro Phe Arg Pro Thr Thr Gly Arg
        980                 985                 990

Thr Ser Leu Tyr Ala Asp Ser Pro  Ser Val Pro Ser His  Leu Pro Asp
    995                 1000                1005

Arg Val  His Phe Ala Ser Pro  Leu His Val Ala Trp  Arg Pro Pro
    1010                1015                1020

<210> SEQ ID NO 22
<211> LENGTH: 12
<212> TYPE: DNA
<213> ORGANISM: Artificial Sequence
<220> FEATURE:
<223> OTHER INFORMATION: linker coding sequence

<400> SEQUENCE: 22
gccggagctg gc                                                             12

<210> SEQ ID NO 23
<211> LENGTH: 248
<212> TYPE: DNA
<213> ORGANISM: Artificial Sequence
<220> FEATURE:
<223> OTHER INFORMATION: ApoAI gene fragment

<400> SEQUENCE: 23
ttggccgtgc tcttcctgac gggtaggtgt ccctaacct agggagccaa ccatcggggg        60
gccttctccc taaatccccg tgcccacccc tcctgggcag aggcagcagg tttctcactg      120
gccccctctc cccacctcc aagcttggcc tttcggctca gatctcagcc cacagctggc      180
ctgatctggg tctcccctcc cacctcagg gagccaggct cggcatttcg tcgacaagct      240
tagccacc                                                                248
```

```
<210> SEQ ID NO 24
<211> LENGTH: 130
<212> TYPE: DNA
<213> ORGANISM: Artificial Sequence
<220> FEATURE:
<223> OTHER INFORMATION: SV40 polyadenylation signal sequence

<400> SEQUENCE: 24
aacttgttta ttgcagctta taatggttac aaataaagca atagcatcac aaatttcaca      60
aataaagcat tttttcact  gcattctagt tgtggtttgt ccaaactcat caatgtatct     120
tatcatgtct                                                            130
```

HEPATITIS B VIRUS (HBV) VACCINES AND USES THEREOF

CROSS REFERENCE TO RELATED APPLICATIONS

This application is a continuation of U.S. application Ser. No. 16/223,251, filed Dec. 18, 2018, now allowed, which claims priority to U.S. Provisional Patent Application No. 62/607,426, filed Dec. 19, 2017, the disclosures of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "065814.1US3 SL" creation date of May 18, 2021, and having a size of 46.6 KB. The sequence listing submitted via EFS-Web is part of the specification and is herein incorporated by reference in its entirety.

BACKGROUND OF THE INVENTION

Hepatitis B virus (HBV) is a small 3.2-kb hepatotropic DNA virus that encodes four open reading frames and seven proteins. About two billion people are infected with HBV, and approximately 240 million people have chronic hepatitis B infection (chronic HBV), characterized by persistent virus and subvirus particles in the blood for more than 6 months (1). Persistent HBV infection leads to T-cell exhaustion in circulating and intrahepatic HBV-specific CD4+ and CD8+ T-cells through chronic stimulation of HBV-specific T-cell receptors with viral peptides and circulating antigens. As a result, T-cell polyfunctionality is decreased (i.e., decreased levels of IL-2, tumor necrosis factor (TNF)-α, IFN-γ, and lack of proliferation).

A safe and effective prophylactic vaccine against HBV infection has been available since the 1980s and is the mainstay of hepatitis B prevention (3). The World Health Organization recommends vaccination of all infants, and, in countries where there is low or intermediate hepatitis B endemicity, vaccination of all children and adolescents (<18 years of age), and of people of certain at risk population categories. Due to vaccination, worldwide infection rates have dropped dramatically. However, prophylactic vaccines do not cure established HBV infection.

Chronic HBV is currently treated with IFN-α and nucleoside or nucleotide analogs, but there is no ultimate cure due to the persistence in infected hepatocytes of an intracellular viral replication intermediate called covalently closed circular DNA (cccDNA), which plays a fundamental role as a template for viral RNAs, and thus new virions. It is thought that induced virus-specific T-cell and B-cell responses can effectively eliminate cccDNA-carrying hepatocytes. Current therapies targeting the HBV polymerase suppress viremia, but offer limited effect on cccDNA that resides in the nucleus and related production of circulating antigen. The most rigorous form of a cure may be elimination of HBV cccDNA from the organism, which has neither been observed as a naturally occurring outcome nor as a result of any therapeutic intervention. However, loss of HBV surface antigens (HBsAg) is a clinically credible equivalent of a cure, since disease relapse can occur only in cases of severe immunosuppression, which can then be prevented by prophylactic treatment. Thus, at least from a clinical standpoint, loss of HBsAg is associated with the most stringent form of immune reconstitution against HBV.

For example, immune modulation with pegylated interferon (pegIFN)-α has proven better in comparison to nucleoside or nucleotide therapy in terms of sustained off-treatment response with a finite treatment course. Besides a direct antiviral effect, IFN-α is reported to exert epigenetic suppression of cccDNA in cell culture and humanized mice, which leads to reduction of virion productivity and transcripts (4). However, this therapy is still fraught with side-effects and overall responses are rather low, in part because IFN-α has only poor modulatory influences on HBV-specific T-cells. In particular, cure rates are low (<10%) and toxicity is high. Likewise, direct acting HBV antivirals, namely the HBV polymerase inhibitors entecavir and tenofovir, are effective as monotherapy in inducing viral suppression with a high genetic barrier to emergence of drug resistant mutants and consecutive prevention of liver disease progression. However, cure of chronic hepatitis B, defined by HBsAg loss or seroconversion, is rarely achieved with such HBV polymerase inhibitors. Therefore, these antivirals in theory need to be administered indefinitely to prevent reoccurrence of liver disease, similar to antiretroviral therapy for human immunodeficiency virus (HIV).

Therapeutic vaccination has the potential to eliminate HBV from chronically infected patients (5). Many strategies have been explored, but to date therapeutic vaccination has not proven successful.

BRIEF SUMMARY OF THE INVENTION

Accordingly, there is an unmet medical need in the treatment of hepatitis B virus (HBV), particularly chronic HBV, for a finite well-tolerated treatment with a higher cure rate. The invention satisfies this need by providing immunogenic compositions and methods for inducing an immune response against hepatitis B virus (HBV) infection. The immunogenic compositions and methods of the invention can be used to provide therapeutic immunity to a subject, such as a subject having chronic HBV infection.

In a general aspect, the application relates to a non-naturally occurring nucleic acid molecule encoding an HBV antigen, such as a truncated HBV core antigen or a HBV polymerase antigen. An HBV antigen according to an embodiment of the application is a consensus antigen capable of inducing an immune response (humoral and cellular) in a mammal against at least two HBV genotypes, preferably inducing a T cell response in a mammal against at least HBV genotypes B, C and D, more preferably, a CD8 T cell response in a human subject against at least HBV genotypes A, B, C and D.

In an embodiment, a non-naturally occurring nucleic acid molecule of the application encodes a truncated HBV core antigen consisting of the amino acid sequence of SEQ ID NO: 2 or SEQ ID NO: 14, and the non-naturally occurring nucleic acid molecule comprises a polynucleotide sequence that is at least 90% identical to SEQ ID NO:1 or SEQ ID NO: 15. Preferably, the non-naturally occurring nucleic acid molecule comprises the polynucleotide sequence of SEQ ID NO: 1 or SEQ ID NO: 15.

In an embodiment, a non-naturally occurring nucleic acid molecule of the application encodes HBV polymerase antigen comprising an amino acid sequence that is at least 98% identical to SEQ ID NO: 4, wherein the HBV polymerase antigen does not have reverse transcriptase activity and RNase H activity. Preferably, an HBV polymerase antigen comprises the amino acid sequence of SEQ ID NO: 4. More preferably, a non-naturally occurring nucleic acid molecule comprises a polynucleotide sequence at least 90% identical to SEQ ID NO: 3 or SEQ ID NO: 16, most preferably 100% identical to SEQ ID NO: 3 or SEQ ID NO: 16.

In another general aspect, the application relates to a vector, preferably a DNA plasmid or a viral vector, comprising a non-naturally occurring nucleic acid molecule of the application.

In another general aspect, the application relates to a recombinant host cell comprising a non-naturally occurring nucleic acid molecule or a vector of the application.

In another general aspect, the application relates to a non-naturally occurring polypeptide encoded by a non-naturally occurring nucleic acid molecule of the application.

In yet another general aspect, the application relates to a composition comprising at least one of a non-naturally occurring nucleic acid molecule, vector, recombinant host cell, and non-naturally occurring polypeptide of the application, and a pharmaceutically acceptable carrier.

In another general aspect, the application relates to an immunogenic combination, particularly a kit, comprising:
 (a) a first non-naturally occurring nucleic acid molecule comprising a first polynucleotide encoding a HBV polymerase antigen having an amino acid sequence that is at least 98% identical to SEQ ID NO: 4, wherein the HBV polymerase antigen does not have reverse transcriptase activity and RNase H activity;
 (b) a second non-naturally occurring nucleic acid molecule comprising a second polynucleotide encoding a truncated HBV core antigen consisting of the amino acid sequence of SEQ ID NO: 2 or SEQ ID NO: 14; and
 (c) a pharmaceutically acceptable carrier,
wherein the first non-naturally occurring nucleic acid molecule and the second non-naturally occurring nucleic acid molecule are present in the same non-naturally occurring nucleic acid molecule or in two different non-naturally occurring nucleic acid molecules.

In some embodiments, an immunogenic combination, particularly a kit, of the application comprises the first polynucleotide present in a first vector and the second polynucleotide present in a second vector. Preferably, the first vector is different from the second vector. More preferably, the vector is a plasmid vector or viral vector. More preferably, each of the first vector and the second vector is a plasmid DNA vector.

In an embodiment, an immunogenic combination, particularly a kit, of the application comprises:
 a) a first plasmid DNA vector comprising a first polynucleotide sequence encoding a HBV polymerase antigen having the amino acid sequence of SEQ ID NO: 4;
 b) a second plasmid DNA vector comprising a second polynucleotide encoding a truncated HBV core antigen consisting of the amino acid sequence of SEQ ID NO: 2 or 14; and
 c) a pharmaceutically acceptable carrier,
wherein each of the first plasmid DNA vector and the second plasmid DNA vector further comprises an antibiotic resistance gene, and an original of replication, and
wherein the first plasmid DNA vector and the second plasmid DNA vector are present in the same composition or in two different compositions.

In a particular embodiment, an immunogenic combination, particularly a kit, of the application comprises:
 a) a first plasmid DNA vector comprising, from 3'-end to 5'-end, a promoter sequence comprising the polynucleotide sequence of SEQ ID NO: 7, an enhancer sequence comprising the polynucleotide sequence of SEQ ID NO: 8, a signal peptide coding sequence comprising the polynucleotide sequence of SEQ ID NO: 5, a first polynucleotide sequence comprising the polynucleotide sequence of SEQ ID NO: 3, and a polyadenylation signal sequence comprising the polynucleotide sequence of SEQ ID NO: 11;
 b) a second plasmid DNA vector comprising, from 3'-end to 5'-end, the promoter sequence comprising the polynucleotide sequence of SEQ ID NO: 7, the regulatory sequence comprising the polynucleotide sequence of SEQ ID NO: 8, the signal peptide coding sequence comprising the polynucleotide sequence of SEQ ID NO: 5, a second polynucleotide sequence comprising the polynucleotide sequence of SEQ ID NO: 1, and the polyadenylation signal sequence comprising the polynucleotide sequence of SEQ ID NO: 11; and
 c) a pharmaceutically acceptable carrier,
wherein each of the first plasmid DNA vector and the second plasmid DNA vector further comprises a kanamycin resistance gene having the polynucleotide sequence of SEQ ID NO: 12, and an original of replication having the polynucleotide sequence of SEQ ID NO: 10, and
wherein the first plasmid DNA vector and the second plasmid DNA vector are present in the same composition or in two different compositions.

In other embodiments, an immunogenic combination, particularly a kit, of the application comprises the first polynucleotide and the second polynucleotide present in the same vector. Preferably, the vector is a plasmid vector or a viral vector. More preferably, the vector is an adenoviral vector, such as an Ad26 or Ad35 vector.

In an embodiment, an immunogenic combination, particularly a kit, of the application comprises:
 a) a vector comprising a first polynucleotide sequence encoding a HBV polymerase antigen having the amino acid sequence of SEQ ID NO: 4, and a second polynucleotide encoding a truncated HBV core antigen consisting of the amino acid sequence of SEQ ID NO: 2 or SEQ ID NO: 14; and
 b) a pharmaceutically acceptable carrier.

In a particular embodiment, an immunogenic combination, particularly a kit, of the application comprises a viral vector, preferably an adenoviral vector, comprising, from 5' end to 3' end, a promoter sequence comprising the polynucleotide sequence of SEQ ID NO: 17, a regulatory sequence comprising the polynucleotide sequence of SEQ ID NO: 23, a signal peptide coding sequence comprising the polynucleotide sequence of SEQ ID NO: 18, a second polynucleotide sequence comprising the polynucleotide sequence of SEQ ID NO: 15, a linker coding sequence comprising the polynucleotide sequence of SEQ ID NO: 22, a first polynucleotide sequence comprising the polynucleotide sequence of SEQ ID NO: 16, and a polyadenylation signal sequence comprising the polynucleotide sequence of SEQ ID NO: 24, and a pharmaceutically acceptable carrier.

Other aspects of the application relate to methods of manufacturing polynucleotides, vectors, polypeptides, and compositions and immunogenic combinations or kits of the application.

And in yet another general aspect, the application relates to a method of inducing an immune response against hepatitis B virus (HBV) in a subject in need thereof, the method comprising administering to the subject an immunogenically effective amount of a composition or an immunogenic combination of the application. Preferably, the method induces an immune response, such as an antibody response and/or a T cell response, in the subject against at least two HBV genotypes. Preferably, the method induces a T cell response in the subject against at least HBV genotypes B, C and D. More preferably, the method induces a CD8 T cell response in a human subject against at least HBV genotypes A, B, C and D. In an embodiment, the method further comprises administering to the subject another immunogenic agent, preferably another HBV antigen.

In another aspect, the application relates to a method of treating a hepatitis B virus (HBV)-induced disease in a subject in need thereof, the method comprising administering to the subject a therapeutically effective amount of a composition or an immunogenic combination of the application. Preferably, the subject has chronic HBV infection, and the HBV-induced disease is selected from the group consisting of advanced fibrosis, cirrhosis and hepatocellular carcinoma (HCC). In an embodiment, the method further comprises administering to the subject another therapeutic agent, preferably another anti-HBV antigen.

The application also relates to a composition, an immunogenic combination or a kit of the application for use in inducing an immune response against hepatitis B virus (HBV); and use of a composition, an immunogenic combination or a kit of the application in the manufacture of a medicament for inducing an immune response against hepatitis B virus (HBV). The use can further comprise a combination with another immunogenic agent, preferably another HBV antigen. Preferably, the subject has chronic HBV infection.

The application further relates to a composition, an immunogenic combination or a kit of the application for use in treating a HBV-induced disease in a subject in need thereof; and use of a composition, an immunogenic combination or a kit of the application in the manufacture of a medicament for treating a HBV-induced disease in a subject in need thereof. The use can further comprise a combination with another therapeutic agent, preferably another anti-HBV antigen. Preferably, the subject has chronic HBV infection, and the HBV-induced disease is selected from the group consisting of advanced fibrosis, cirrhosis and hepatocellular carcinoma (HCC).

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A is a diagram of the genome of hepatitis B virus (HBV); in the native virus, the polymerase protein (Pol) contains the coding sequence for the envelope proteins in a different open reading frame; the envelope proteins (pre-S1, pre-S2, and S) are in the same open reading frame; FIG. 1B shows the viral life cycle of HBV;

FIGS. 2A-2H show the design and optimization of expression cassettes and DNA plasmids encoding HBV pol and core antigens as described in Example 1; FIG. 2A is a schematic representation of an expression strategy in which coding sequences of the HBV core and pol antigens are fused in frame; FIG. 2B is a schematic representation of an expression strategy in which coding sequences of both the core and pol antigens are expressed from a single plasmid by means of the ribosomal FA2 slippage site; FIG. 2C is a schematic representation of an expression strategy in which the core and pol antigens are expressed from two separate plasmids; FIG. 2D is a Western blot of core antigen expression in HEK293T cells transfected with a plasmid expressing core with and without the post-transcriptional regulatory element WPRE; expression was tested in cell lysate (left) and supernatant (sup; right) using an α-core antibody; FIG. 2E is a Western blot analysis showing a comparison of core expression in HEK293T cells transfected with a core expressing plasmid including the intron/exon sequence derived from human apolipoprotein A1 precursor ("AI intron"), untranslated R-U5 domain of the human T-cell leukemia virus type 1 (HTLV-1) long terminal repeat (LTR) ("HTLV R"), or triple enhancer composite sequence of the HTLV-1 LTR, synthetic rabbit β-globin intron, and a splicing enhancer ("triple"); the unlabeled lane is purified core protein as a size marker; expression was tested in both lysate (left) and supernatant (sup; right); core antigen expression was highest with the triple enhancer composite sequence; FIG. 2F is a Western blot analysis of core antigen secretion using different signal peptides fused to the N-terminus of the HBV core antigen; the most efficient protein secretion was observed with the Cystatin S signal peptide;

FIG. 2G is a schematic representation of optimized HBV core/pol antigen expression cassettes for each of the three expression strategies illustrated in FIGS. 2A-2C; CMVpr: human CMV-IE promoter; TRE: triple enhancer sequence; SP: cystatin S signal peptide; FA2: FMDV ribosomal slippage site; pA: BGH polyadenylation signal; FIG. 2H is a Western blot analysis of HBV core and pol antigen expression of pDK vectors containing each of the expression cassettes shown in FIG. 2G; lanes 1 and 2: pDK-core; lanes 3 and 4: pDK-pol; lanes 5 and 6: pDK-coreFA2Pol; lanes 7 and 8: pDK-core-pol fusion: the most consistent expression profile for cellular and secreted core and pol antigens was observed when the antigens were encoded by separate vectors;

FIG. 3A shows a DNA plasmid encoding an HBV core antigen according to an embodiment of the application; FIG. 3B shows a DNA plasmid encoding an HBV polymerase (pol) antigen according to an embodiment of the application; the HBV core and pol antigens are expressed under control of a CMV promoter with an N-terminal cystatin S signal peptide that is cleaved from the expressed antigen upon secretion from the cell; transcriptional regulatory elements of the plasmid include an enhancer sequence located between the CMV promoter and the polynucleotide sequence encoding the HBV antigen and a bGH polyadenylation sequence located downstream of the polynucleotide sequence encoding the HBV antigen; a second expression cassette is included in the plasmid in reverse orientation including a kanamycin resistance gene under control of an Amp$^r$ (bla) promoter; an origin of replication (pUC) is also included in reverse orientation;

FIG. 7A shows the IFN-γ cytokine response after immunization with DNA plasmids expressing HBV Core and Pol antigens; peptide pools used to stimulate PBMCs isolated from the vaccinated animal groups are indicated in gray scale; the number of responsive T-cells are indicated on the y-axis expressed as spot forming cells (SFC) per $10^6$ PBMC; FIG. 7B shows CD4 and CD8 T-cell memory immune response against Core, Pol-1, and Pol-2 peptide pools as measured by flow cytometry; the graph shows the results from Day 76 as % CD4 or CD8 T-cell response (IFN-γ, IL-2 and TNF-α) to the 3 pools after the DMSO media-only background was subtracted for each pool; CD4 response is shown on the left and CD8 response is shown on the right;

FIG. 8A shows the expression cassette for a truncated HBV core antigen, which contains a CMV promoter, an intron (a fragment derived from the human ApoAI gene-GenBank accession X01038 base pairs 295-523, harboring the ApoAI second intron), a human immunoglobulin secretion signal, followed by a coding sequence for a truncated HBV core antigen and a SV40 polyadenylation signal; FIG. 8B shows the expression cassette for a fusion protein of a truncated HBV core antigen operably linked to a HBV polymerase antigen, which is otherwise identical to the expression cassette for the truncated HBV core antigen except the HBV antigen.

DETAILED DESCRIPTION OF THE INVENTION

Figure 1A:
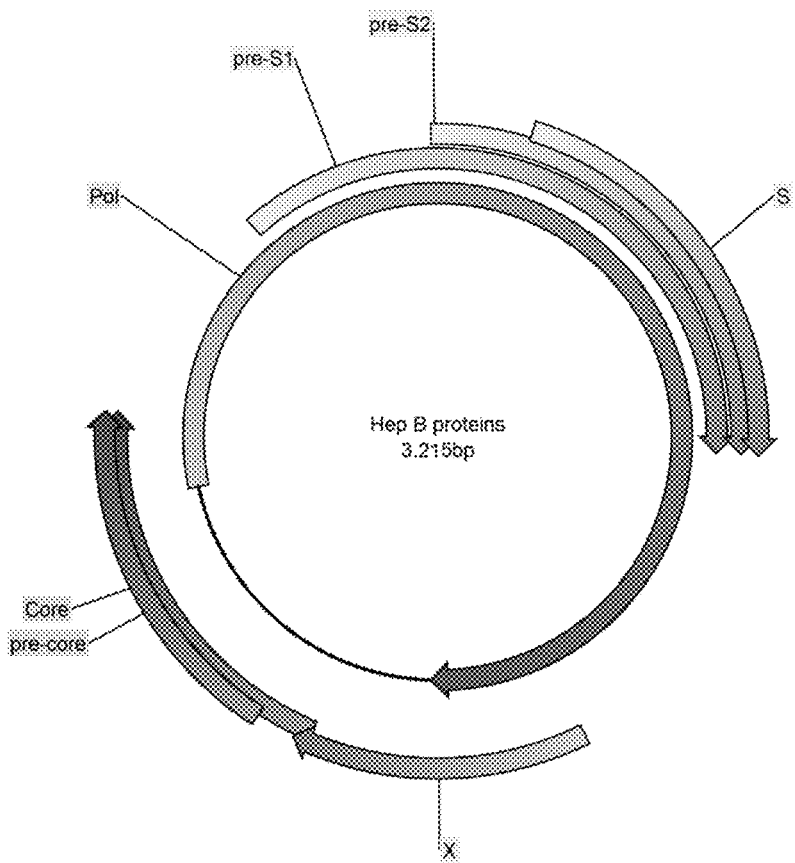
FIGS. 1A-1B depict the genome and viral life cycle of hepatitis B virus.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1 mg/mL to 10 mg/mL includes 0.9 mg/mL to 11 mg/mL. As used herein, the use of a numerical range expressly includes all possible subranges, and all individual numerical values within that range, including integers within such ranges and fractions of the values unless the context clearly indicates otherwise.

The phrases "percent (%) sequence identity" or "% identity" or "% identical to" when used with reference to an amino acid sequence describe the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 91%, 92%, 93%, 94%, 95%, 97%, 98%, 99%, or 100% identity over the full-length of the amino acid sequences) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g., using the NCBI BLAST algorithm (Altschul S F, et al (1997), Nucleic Acids Res. 25:3389-3402).

As used herein, the terms and phrases "in combination," "in combination with," "co-delivery," and "administered together with" in the context of the administration of two or more therapies or components to a subject refers to simultaneous administration of two or more therapies or components, such as two vectors, e.g., DNA plasmids, or an immunogenic combination and an adjuvant. "Simultaneous administration" can be administration of the two components at least within the same day. When two components are "administered together with" or "administered in combination with," they can be administered in separate compositions sequentially within a short time period, such as 24, 20, 16, 12, 8 or 4 hours, or within 1 hour, or they can be administered in a single composition at the same time. The use of the term "in combination with" does not restrict the order in which therapies or components are administered to a subject. For example, a first therapy or component (e.g. first DNA plasmid encoding an HBV antigen) can be administered prior to (e.g., 5 minutes to one hour before), concomitantly with or simultaneously with, or subsequent to (e.g., 5 minutes to one hour after) the administration of a second therapy or component (e.g., second DNA plasmid encoding an HBV antigen). In some embodiments, a first therapy or component (e.g. first DNA plasmid encoding an HBV antigen) and a second therapy or component (e.g., second DNA plasmid encoding an HBV antigen) are administered in the same composition. In other embodiments, a first therapy or component (e.g. first DNA plasmid encoding an HBV antigen) and a second therapy or component (e.g., second DNA plasmid encoding an HBV antigen) are administered in separate compositions.

As used herein, a "non-naturally occurring" nucleic acid or polypeptide, refers to a nucleic acid or polypeptide that does not occur in nature. A "non-naturally occurring" nucleic acid or polypeptide can be synthesized, treated, fabricated, and/or otherwise manipulated in a laboratory and/or manufacturing setting. In some cases, a non-naturally occurring nucleic acid or polypeptide can comprise a naturally-occurring nucleic acid or polypeptide that is treated, processed, or manipulated to exhibit properties that were not present in the naturally-occurring nucleic acid or polypeptide, prior to treatment. As used herein, a "non-naturally occurring" nucleic acid or polypeptide can be a nucleic acid or polypeptide isolated or separated from the natural source in which it was discovered, and it lacks covalent bonds to sequences with which it was associated in the natural source.

A "non-naturally occurring" nucleic acid or polypeptide can be made recombinantly or via other methods, such as chemical synthesis.

As used herein, "subject" means any animal, preferably a mammal, most preferably a human, to whom will be or has been treated by a method according to an embodiment of the application. The term "mammal" as used herein encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

As used herein, the term "operably linked" refers to a linkage or a juxtaposition wherein the components so described are in a relationship permitting them to function in their intended manner. For example, a regulatory sequence operably linked to a nucleic acid sequence of interest is capable of directing the transcription of the nucleic acid sequence of interest, or a signal sequence operably linked to an amino acid sequence of interest is capable of secreting or translocate the amino acid sequence of interest over a membrane.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. For example, while embodiments of HBV vectors of the application (e.g., plasmid DNA or viral vectors) described herein may contain particular components, including, but not limited to, certain promoter sequences, enhancer or regulatory sequences, signal peptides, coding sequence of an HBV antigen, polyadenylation signal sequences, etc. arranged in a particular order, those having ordinary skill in the art will appreciate that the concepts disclosed herein may equally apply to other components arranged in other orders that can be used in HBV vectors of the application. The application contemplates use of any of the applicable components in any combination having any sequence that can be used in HBV vectors of the application, whether or not a particular combination is expressly described.

Hepatitis B Virus (HBV)

As used herein "hepatitis B virus" or "HBV" refers to a virus of the hepadnaviridae family. HBV is a small (e.g., 3.2 kb) hepatotropic DNA virus that encodes four open reading frames and seven proteins. See FIG. 1A. The seven proteins encoded by HBV include small (S), medium (M), and large (L) surface antigen (HBsAg) or envelope (Env) proteins, pre-Core protein, core protein, viral polymerase (Pol), and HBx protein. HBV expresses three surface antigens, or envelope proteins, L, M, and S, with S being the smallest and L being the largest. The extra domains in the M and L proteins are named Pre-S2 and Pre-S1, respectively. Core protein is the subunit of the viral nucleocapsid. Pol is needed for synthesis of viral DNA (reverse transcriptase, RNaseH, and primer), which takes place in nucleocapsids localized to the cytoplasm of infected hepatocytes. PreCore is the core protein with an N-terminal signal peptide and is proteolytically processed at its N and C termini before secretion from infected cells, as the so-called hepatitis B e-antigen (HBeAg). HBx protein is required for efficient transcription of covalently closed circular DNA (cccDNA). HBx is not a viral structural protein. All viral proteins of HBV have their own mRNA except for core and polymerase, which share an mRNA. With the exception of the protein pre-Core, none of the HBV viral proteins are subject to post-translational proteolytic processing.

Figure 1B:
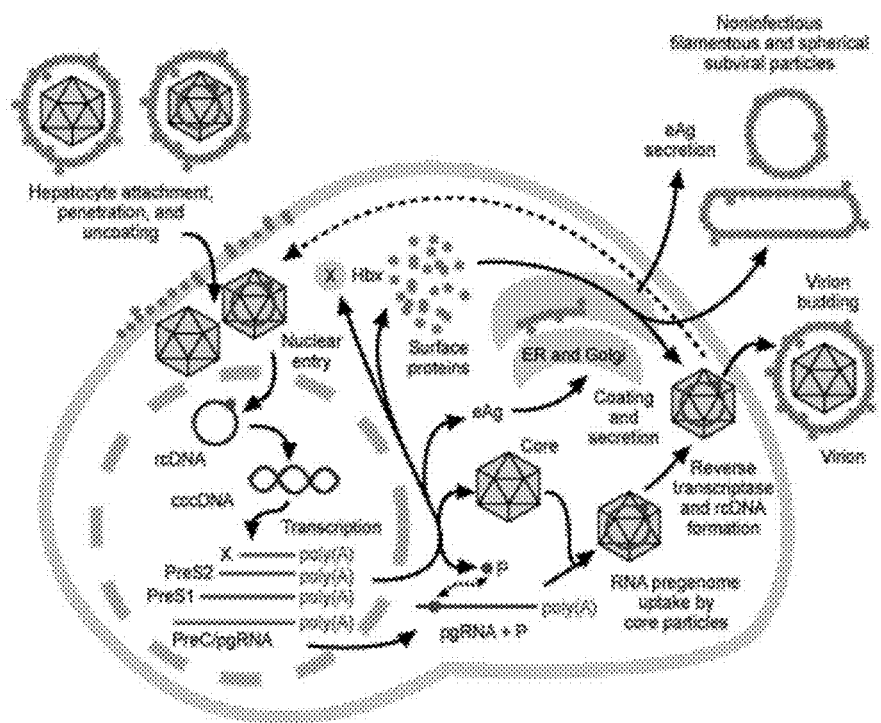

The HBV virion contains a viral envelope, nucleocapsid, and single copy of the partially double-stranded DNA genome. The nucleocapsid comprises 120 dimers of core protein and is covered by a capsid membrane embedded with the S, M, and L viral envelope or surface antigen proteins. After entry into the cell, the virus is uncoated and the capsid-containing relaxed circular DNA (rcDNA) with covalently bound viral polymerase migrates to the nucleus. During that process, phosphorylation of the core protein induces structural changes, exposing a nuclear localization signal enabling interaction of the capsid with so-called importins. These importins mediate binding of the core protein to nuclear pore complexes upon which the capsid disassembles and polymerase/rcDNA complex is released into the nucleus. Within the nucleus the rcDNA becomes deproteinized (removal of polymerase) and is converted by host DNA repair machinery to a covalently closed circular DNA (cccDNA) genome from which overlapping transcripts encode for HBeAg, HBsAg, Core protein, viral polymerase and HBx protein. Core protein, viral polymerase, and pre-genomic RNA (pgRNA) associate in the cytoplasm and self-assemble into immature pgRNA-containing capsid particles, which further convert into mature rcDNA-capsids and function as a common intermediate that is either enveloped and secreted as infectious virus particles or transported back to the nucleus to replenish and maintain a stable cccDNA pool. See FIG. 1B.

To date, HBV is divided into four serotypes (adr, adw, ayr, ayw) based on antigenic epitopes present on the envelope proteins, and into eight genotypes (A, B, C, D, E, F, G, and H) based on the sequence of the viral genome. The HBV genotypes are distributed over different geographic regions. For example, the most prevalent genotypes in Asia are genotypes B and C. Genotype D is dominant in Africa, the Middle East, and India, whereas genotype A is widespread in Northern Europe, sub-Saharan Africa, and West Africa.

HBV Antigens

As used herein, the terms "HBV antigen," "antigenic polypeptide of HBV," "HBV antigenic polypeptide," "HBV antigenic protein," "HBV immunogenic polypeptide," and "HBV immunogen" all refer to a polypeptide capable of inducing an immune response, e.g., a humoral and/or cellular mediated response, against an HBV in a subject. The HBV antigen can be a polypeptide of HBV, a fragment or epitope thereof, or a combination of multiple HBV polypeptides, portions or derivatives thereof. An HBV antigen is capable of raising in a host a protective immune response, e.g., inducing an immune response against a viral disease or infection, and/or producing an immunity (i.e., vaccinates) in a subject against a viral disease or infection, that protects the subject against the viral disease or infection. For example, an HBV antigen can comprise a polypeptide or immunogenic fragment(s) thereof from any HBV protein, such as HBeAg, pre-core protein, HBsAg (S, M, or L proteins), core protein, viral polymerase, or HBx protein derived from any HBV genotype, e.g., genotype A, B, C, D, E, F, G, and/or H, or combination thereof.

(1) HBV Core Antigen

As used herein, each of the terms "HBV core antigen," "HBcAg" and "core antigen" refers to an HBV antigen capable of inducing an immune response, e.g., a humoral and/or cellular mediated response, against an HBV core protein in a subject. Each of the terms "core," "core polypeptide," and "core protein" refers to the HBV viral core protein. Full-length core antigen is typically 183 amino acids in length and includes an assembly domain (amino acids 1 to 149) and a nucleic acid binding domain (amino acids 150 to 183). The 34-residue nucleic acid binding domain is required for pre-genomic RNA encapsidation. This domain also functions as a nuclear import signal. It comprises 17 arginine residues and is highly basic, consistent with its function. HBV core protein is dimeric in solution, with the dimers self-assembling into icosahedral capsids. Each dimer of core protein has four α-helix bundles flanked by an α-helix domain on either side. Truncated HBV core proteins lacking the nucleic acid binding domain are also capable of forming capsids.

In an embodiment of the application, an HBV antigen is a truncated HBV core antigen. As used herein, a "truncated HBV core antigen," refers to an HBV antigen that does not contain the entire length of an HBV core protein, but is capable of inducing an immune response against the HBV core protein in a subject. For example, an HBV core antigen can be modified to delete one or more amino acids of the highly positively charged (arginine rich) C-terminal nucleic acid binding domain of the core antigen, which typically contains seventeen arginine (R) residues. A truncated HBV core antigen of the application is preferably a C-terminally truncated HBV core protein which does not comprise the HBV core nuclear import signal and/or a truncated HBV core protein from which the C-terminal HBV core nuclear import signal has been deleted. In an embodiment, a truncated HBV core antigen comprises a deletion in the C-terminal nucleic acid binding domain, such as a deletion of 1 to 34 amino acid residues of the C-terminal nucleic acid binding domain, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acid residues, preferably a deletion of all 34 amino acid residues. In a preferred embodiment, a truncated HBV core antigen comprises a deletion in the C-terminal nucleic acid binding domain, preferably a deletion of all 34 amino acid residues.

An HBV core antigen of the application can be a consensus sequence derived from multiple HBV genotypes (e.g., genotypes A, B, C, D, E, F, G, and H). As used herein, "consensus sequence" means an artificial sequence of amino acids based on an alignment of amino acid sequences of homologous proteins, e.g., as determined by an alignment (e.g., using Clustal Omega) of amino acid sequences of homologous proteins. It can be the calculated order of most frequent amino acid residues, found at each position in a sequence alignment, based upon sequences of HBV antigens (e.g., core, pol, etc.) from at least 100 natural HBV isolates. A consensus sequence can be non-naturally occurring and different from the native viral sequences. Consensus sequences can be designed by aligning multiple HBV antigen sequences from different sources using a multiple sequence alignment tool, and at variable alignment positions, selecting the most frequent amino acid. Preferably, a consensus sequence of an HBV antigen is derived from HBV genotypes B, C, and D. The term "consensus antigen" is used to refer to an antigen having a consensus sequence.

An exemplary truncated HBV core antigen according to the application lacks the nucleic acid binding function, and is capable of inducing an immune response in a mammal against at least two HBV genotypes. Preferably a truncated HBV core antigen is capable of inducing a T cell response in a mammal against at least HBV genotypes B, C and D. More preferably, a truncated HBV core antigen is capable of inducing a CD8 T cell response in a human subject against at least HBV genotypes A, B, C and D.

Preferably, an HBV core antigen of the application is a consensus antigen, preferably a consensus antigen derived from HBV genotypes B, C, and D, more preferably a truncated consensus antigen derived from HBV genotypes B, C, and D. An exemplary truncated HBV core consensus antigen according to the application consists of an amino acid sequence that is at least 90% identical to SEQ ID NO: 2 or SEQ ID NO: 14, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2 or SEQ ID NO: 14. SEQ ID NO: 2 and SEQ ID NO: 14 are core consensus antigens derived from HBV genotypes B, C, and D. SEQ ID NO: 2 and SEQ ID NO:14 contain a 34-amino acid C-terminal deletion of the highly positively charged (arginine rich) nucleic acid binding domain of the native core antigen.

In a particular embodiment of the application, an HBV core antigen is a truncated HBV antigen consisting of the amino acid sequence of SEQ ID NO: 2. In another particular embodiment, an HBV core antigen is a truncated HBV antigen consisting of the amino acid sequence of SEQ ID NO: 14.

(2) HBV Polymerase Antigen

As used herein, the term "HBV polymerase antigen," "HBV Pol antigen" or "HBV pol antigen" refers to an HBV antigen capable of inducing an immune response, e.g., a humoral and/or cellular mediated response, against an HBV polymerase in a subject. Each of the terms "polymerase," "polymerase polypeptide," "Pol" and "pol" refers to the HBV viral DNA polymerase. The HBV viral DNA polymerase has four domains, including, from the N terminus to the C terminus, a terminal protein (TP) domain, which acts as a primer for minus-strand DNA synthesis; a spacer that is nonessential for the polymerase functions; a reverse transcriptase (RT) domain for transcription; and a RNase H domain.

In an embodiment of the application, an HBV antigen comprises an HBV Pol antigen, or any immunogenic fragment or combination thereof. An HBV Pol antigen can contain further modifications to improve immunogenicity of the antigen, such as by introducing mutations into the active sites of the polymerase and/or RNase domains to decrease or substantially eliminate certain enzymatic activities.

Preferably, an HBV Pol antigen of the application does not have reverse transcriptase activity and RNase H activity, and is capable of inducing an immune response in a mammal against at least two HBV genotypes. Preferably, an HBV Pol antigen is capable of inducing a T cell response in a mammal against at least HBV genotypes B, C and D. More preferably, a HBV Pol antigen is capable of inducing a CD8 T cell response in a human subject against at least HBV genotypes A, B, C and D.

Thus, in some embodiments, an HBV Pol antigen is an inactivated Pol antigen. In an embodiment, an inactivated HBV Pol antigen comprises one or more amino acid mutations in the active site of the polymerase domain. In another embodiment, an inactivated HBV Pol antigen comprises one or more amino acid mutations in the active site of the RNaseH domain. In a preferred embodiment, an inactivated HBV pol antigen comprises one or more amino acid mutations in the active site of both the polymerase domain and the RNaseH domain. For example, the "YXDD" motif in the polymerase domain of an HBV pol antigen that can be required for nucleotide/metal ion binding can be mutated, e.g., by replacing one or more of the aspartate residues (D) with asparagine residues (N), eliminating or reducing metal coordination function, thereby decreasing or substantially eliminating reverse transcriptase function. Alternatively, or in addition to mutation of the "YXDD" motif, the "DEDD" motif in the RNaseH domain of an HBV pol antigen required for $Mg^{2+}$ coordination can be mutated, e.g., by replacing one or more aspartate residues (D) with asparagine residues (N) and/or replacing the glutamate residue (E) with glutamine (Q), thereby decreasing or substantially eliminating RNaseH function. In a particular embodiment, an HBV pol antigen is modified by (1) mutating the aspartate residues (D) to asparagine residues (N) in the "YXDD" motif of the polymerase domain; and (2) mutating the first aspartate residue (D) to an asparagine residue (N) and the first glutamate residue (E) to a glutamine residue (N) in the "DEDD" motif of the RNaseH domain, thereby decreasing or substantially eliminating both the reverse transcriptase and RNaseH functions of the pol antigen.

In a preferred embodiment of the application, an HBV pol antigen is a consensus antigen, preferably a consensus antigen derived from HBV genotypes B, C, and D, more preferably an inactivated consensus antigen derived from HBV genotypes B, C, and D. An exemplary HBV pol consensus antigen according to the application comprises an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4. SEQ ID NO: 4 is a pol consensus antigen derived from HBV genotypes B, C, and D comprising four mutations located in the active sites of the polymerase and RNaseH domains. In particular, the four mutations include mutation of the aspartic acid residues (D) to asparagine residues (N) in the "YXDD" motif of the polymerase domain; and mutation of the first aspartate residue (D) to an asparagine residue (N) and mutation of the glutamate residue (E) to a glutamine residue (Q) in the "DEDD" motif of the RNaseH domain.

In a particular embodiment of the application, an HBV pol antigen comprises the amino acid sequence of SEQ ID NO: 4. In other embodiments of the application, an HBV pol antigen consists of the amino acid sequence of SEQ ID NO: 4.

(3) Fusion of HBV Core Antigen and HBV Polymerase Antigen

As used herein the term "fusion protein" or "fusion" refers to a single polypeptide chain having at least two polypeptide domains that are not normally present in a single, natural polypeptide.

In an embodiment of the application, an HBV antigen comprises a fusion protein comprising a truncated HBV core antigen operably linked to a HBV Pol antigen, or a HBV Pol antigen operably linked to a truncated HBV core antigen, preferably via a linker.

As used herein, the term "linker" refers to a compound or moiety that acts as a molecular bridge to operably link two different molecules, wherein one portion of the linker is operably linked to a first molecule, and wherein another portion of the linker is operably linked to a second molecule. For example, in a fusion protein containing a first polypeptide and a second heterologous polypeptide, a linker serves primarily as a spacer between the first and second polypeptides. In an embodiment, a linker is made up of amino acids linked together by peptide bonds, preferably from 1 to 20 amino acids linked by peptide bonds, wherein the amino acids are selected from the 20 naturally occurring amino acids. In an embodiment, the 1 to 20 amino acids are selected from glycine, alanine, proline, asparagine, glutamine, and lysine. Preferably, a linker is made up of a majority of amino acids that are sterically unhindered, such as glycine and alanine. Exemplary linkers are polyglycines, particularly (Gly)$_5$, (Gly)$_8$; poly(Gly-Ala), and polyalanines. One exemplary suitable linker as shown in the Examples below is (AlaGly)$_n$, wherein n is an integer of 2 to 5.

Preferably, a fusion protein of the application is capable of inducing an immune response in a mammal against HBV core and HBV Pol of at least two HBV genotypes. Preferably, a fusion protein is capable of inducing a T cell response in a mammal against at least HBV genotypes B, C and D. More preferably, the fusion protein is capable of inducing a CD8 T cell response in a human subject against at least HBV genotypes A, B, C and D.

In an embodiment of the application, a fusion protein comprises a truncated HBV core antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2 or SEQ ID NO: 14, a linker, and a HBV Pol antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100%, identical to SEQ ID NO: 4.

In a preferred embodiment of the application, a fusion protein comprises a truncated HBV core antigen consisting of the amino acid sequence of SEQ ID NO: 14, a linker comprising (AlaGly)$_n$, wherein n is an integer of 2 to 5, and a HBV Pol antigen having the amino acid sequence of SEQ ID NO: 4. More preferably, a fusion protein according to an embodiment of the application comprises the amino acid sequence of SEQ ID NO: 20.

In an embodiment of the application, a fusion protein further comprises a signal sequence. Preferably, the signal sequence has the amino acid sequence of SEQ ID NO: 6 or SEQ ID NO: 19. More preferably, a fusion protein comprises the amino acid sequence of SEQ ID NO: 21.

Polynucleotides and Vectors

In another general aspect, the application provides a non-naturally occurring nucleic acid molecule encoding an HBV antigen according to the application, and a vector comprising the non-naturally occurring nucleic acid. A non-naturally occurring nucleic acid molecule can comprise any polynucleotide sequence encoding an HBV antigen of the application, which can be made using methods known in the art in view of the present disclosure. Preferably, a polynucleotide encodes at least one of a truncated HBV core antigen and an HBV polymerase antigen of the application. A polynucleotide can be in the form of RNA or in the form of DNA obtained by recombinant techniques (e.g., cloning) or produced synthetically (e.g., chemical synthesis). The DNA can be single-stranded or double-stranded, or can contain portions of both double-stranded and single-stranded sequence. The DNA can, for example, comprise genomic DNA, cDNA, or combinations thereof. The polynucleotide can also be a DNA/RNA hybrid. The polynucleotides and vectors of the application can be used for recombinant protein production, expression of the protein in a host cell, or the production of viral particles. Preferably, a polynucleotide is DNA.

In an embodiment of the application, a non-naturally occurring nucleic acid molecule comprises a polynucleotide encoding a truncated HBV core antigen consisting of an amino acid sequence that is at least 90% identical to SEQ ID NO: 2 or SEQ ID NO: 14, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 2, preferably 98%, 99% or 100% identical to SEQ ID NO: 2 or SEQ ID NO: 14. In a particular embodiment of the application, a non-naturally occurring nucleic acid molecule encodes a truncated HBV core antigen consisting the amino acid sequence of SEQ ID NO: 2 or SEQ ID NO: 14.

Examples of polynucleotide sequences of the application encoding a truncated HBV core antigen consisting of the amino acid sequence of SEQ ID NO: 2 or SEQ ID NO: 14 include, but are not limited to, a polynucleotide sequence at least 90% identical to SEQ ID NO: 1 or SEQ ID NO: 15, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15, preferably 98%, 99% or 100% identical to SEQ ID NO: 1 or SEQ ID NO:15. Exemplary non-naturally occurring nucleic acid molecules encoding a truncated HBV core antigen have the polynucleotide sequence of SEQ ID NOs: 1 or 15.

In an embodiment of the application, a non-naturally occurring nucleic acid molecule encodes a HBV polymerase antigen comprising an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably 100% identical to SEQ ID NO: 4. In a particular embodiment of the application, a non-naturally occurring nucleic acid molecule encodes a HBV polymerase antigen consisting of the amino acid sequence of SEQ ID NO: 4.

Examples of polynucleotide sequences of the application encoding a HBV Pol antigen comprising the amino acid sequence of SEQ ID NO: 4 include, but are not limited to, a polynucleotide sequence at least 90% identical to SEQ ID NO: 3 or SEQ ID NO: 16, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3 or SEQ ID NO: 16, preferably 98%, 99% or 100% identical to SEQ ID NO: 3 or SEQ ID NO: 16. Exemplary non-naturally occurring nucleic acid molecules encoding a HBV pol antigen have the polynucleotide sequence of SEQ ID NOs: 3 or 16.

In another embodiment of the application, a non-naturally occurring nucleic acid molecule encodes a fusion protein comprising a truncated HBV core antigen operably linked to a HBV Pol antigen, or a HBV Pol antigen operably linked to a truncated HBV core antigen. In a particular embodiment, a non-naturally occurring nucleic acid molecule of the application encodes a truncated HBV core antigen consisting of an amino acid sequence that is at least 90% identical to SEQ ID NO: 2 or SEQ ID NO: 14, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 2 or SEQ ID NO: 14, preferably 100% identical to SEQ ID NO: 2 or SEQ ID NO: 14, more preferably 100% identical to SEQ ID NO: 14; a linker; and a HBV polymerase antigen comprising an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably 98%, 99% or 100% identical to SEQ ID NO: 4. In a particular embodiment of the application, a non-naturally occurring nucleic acid molecule encodes a fusion protein comprising a truncated HBV core antigen consisting of the amino acid sequence of SEQ ID NO: 14, a linker comprising (AlaGly)$_n$, wherein n is an integer of 2 to 5; and a HBV Pol antigen comprising the amino acid sequence of SEQ ID NO: 4. In a particular embodiment of the application, a non-naturally occurring nucleic acid molecule encodes a fusion protein comprising the amino acid sequence of SEQ ID NO: 20.

Examples of polynucleotide sequences of the application encoding a fusion protein include, but are not limited to, a polynucleotide sequence at least 90% identical to SEQ ID NO: 1 or SEQ ID NO: 15, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15, preferably 98%, 99% or 100% identical to SEQ ID NO: 1 or SEQ ID NO: 15, operably linked to a linker coding sequence at least 90% identical to SEQ ID NO: 22, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 22, preferably 98%, 99% or 100% identical to SEQ ID NO: 22, which is further operably linked to a polynucleotide sequence at least 90% identical to SEQ ID NO: 3 or SEQ ID NO: 16, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3 or SEQ ID NO: 16, preferably 98%, 99% or 100% identical to SEQ ID NO: 3 or SEQ ID NO: 16. In particular embodiments of the application, a non-naturally occurring nucleic acid molecule encoding a fusion protein comprises SEQ ID NO: 1 or SEQ ID NO: 15, operably linked to SEQ ID NO: 22, which is further operably linked to SEQ ID NO: 3 or SEQ ID NO: 16.

The application also relates to a vector comprising an isolated polynucleotide encoding an HBV antigen. As used herein, a "vector" is a nucleic acid molecule used to carry genetic material into another cell, where it can be replicated and/or expressed. Any vector known to those skilled in the art in view of the present disclosure can be used. Examples of vectors include, but are not limited to, plasmids, viral vectors (bacteriophage, animal viruses, and plant viruses), cosmids, and artificial chromosomes (e.g., YACs). Preferably, a vector is a DNA plasmid. A vector can be a DNA vector or an RNA vector. One of ordinary skill in the art can construct a vector of the application through standard recombinant techniques in view of the present disclosure.

A vector of the application can be an expression vector. As used herein, the term "expression vector" refers to any type of genetic construct comprising a nucleic acid coding for an RNA capable of being transcribed. Expression vectors include, but are not limited to, vectors for recombinant protein expression, such as a DNA plasmid or a viral vector, and vectors for delivery of nucleic acid into a subject for expression in a tissue of the subject, such as a DNA plasmid or a viral vector. It will be appreciated by those skilled in the art that the design of the expression vector can depend on such factors as the choice of the host cell to be transformed, the level of expression of protein desired, etc.

Vectors of the application can contain a variety of regulatory sequences. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. In the context of the disclosure, this term encompasses promoters, enhancers and other expression control elements (e.g., polyadenylation signals and elements that affect mRNA stability).

In some embodiments of the application, a vector is a non-viral vector. Examples of non-viral vectors include, but are not limited to, DNA plasmids, bacterial artificial chromosomes, yeast artificial chromosomes, bacteriophages, etc. Examples of non-viral vectors include, but are not limited to, RNA replicon, mRNA replicon, modified mRNA replicon or self-amplifying mRNA, closed linear deoxyribonucleic acid, e.g., a linear covalently closed DNA, e.g., a linear covalently closed double stranded DNA molecule. Preferably, a non-viral vector is a DNA plasmid. A "DNA plasmid", which is used interchangeably with "DNA plasmid vector," "plasmid DNA" or "plasmid DNA vector," refers to a double-stranded and generally circular DNA sequence that is capable of autonomous replication in a suitable host cell. DNA plasmids used for expression of an encoded polynucleotide typically comprise an origin of replication, a multiple cloning site, and a selectable marker, which for example, can be an antibiotic resistance gene. Examples of suitable DNA plasmids that can be used include, but are not limited to, commercially available expression vectors for use in well-known expression systems (including both prokaryotic and eukaryotic systems), such as pSE420 (Invitrogen, San Diego, Calif.), which can be used for production and/or expression of protein in *Escherichia coli*; pYES2 (Invitrogen, Thermo Fisher Scientific), which can be used for production and/or expression in *Saccharomyces cerevisiae* strains of yeast; MAXBAC® complete baculovirus expression system (Thermo Fisher Scientific), which can be used for production and/or expression in insect cells; pcDNA™ or pcDNA3™ (Life Technologies, Thermo Fisher Scientific), which can be used for high level constitutive protein expression in mammalian cells; and pVAX or pVAX-1 (Life Technologies, Thermo Fisher Scientific), which can be used for high-level transient expression of a protein of interest in most mammalian cells. The backbone of any commercially available DNA plasmid can be modified to optimize protein expression in the host cell, such as to reverse the orientation of certain elements (e.g., origin of replication and/or antibiotic resistance cassette), replace a promoter endogenous to the plasmid (e.g., the promoter in the antibiotic resistance cassette), and/or replace the polynucleotide sequence encoding transcribed proteins (e.g., the coding sequence of the antibiotic resistance gene), by using routine techniques and readily available starting materials. (See e.g., Sambrook et al., Molecular Cloning a Laboratory Manual, Second Ed. Cold Spring Harbor Press (1989)).

Preferably, a DNA plasmid is an expression vector suitable for protein expression in mammalian host cells. Expression vectors suitable for protein expression in mammalian host cells include, but are not limited to, pcDNA™, pcDNA3™, pVAX, pVAX-1, ADVAX, NTC8454, etc. Preferably, an expression vector is based on pVAX-1, which can be further modified to optimize protein expression in mammalian cells. pVAX-1 is a commonly used plasmid in DNA vaccines, and contains a strong human immediate early cytomegalovirus (CMV-IE) promoter followed by the bovine growth hormone (bGH)-derived polyadenylation sequence (pA). pVAX-1 further contains a pUC origin of replication and a kanamycin resistance gene driven by a small prokaryotic promoter that allows for bacterial plasmid propagation.

A vector of the application can also be a viral vector. In general, viral vectors are genetically engineered viruses carrying modified viral DNA or RNA that has been rendered non-infectious, but still contains viral promoters and transgenes, thus allowing for translation of the transgene through a viral promoter. Because viral vectors are frequently lacking infectious sequences, they require helper viruses or packaging lines for large-scale transfection. Examples of viral vectors that can be used include, but are not limited to, adenoviral vectors, adeno-associated virus vectors, pox virus vectors, enteric virus vectors, Venezuelan Equine Encephalitis virus vectors, Semliki Forest Virus vectors, Tobacco Mosaic Virus vectors, lentiviral vectors, arenavirus viral vectors, replication-deficient arenavirus viral vectors or replication-competent arenavirus viral vectors, bi-segmented or tri-segmented arenavirus, infectious arenavirus viral vectors, nucleic acids which comprise an arenavirus genomic segment wherein one open reading frame of the genomic segment is deleted or functionally inactivated (and replaced by a nucleic acid encoding a HBV antigen as described herein), arenavirus such as lymphocytic choriomeningitidis virus (LCMV), e.g., clone 13 strain or MP strain, and arenavirus such as Junin virus e.g., Candid #1 strain, etc. The vector can also be a non-viral vector.

Preferably, a viral vector is an adenovirus vector, e.g., a recombinant adenovirus vector. A recombinant adenovirus vector can for instance be derived from a human adenovirus (HAdV, or AdHu), or a simian adenovirus such as chimpanzee or gorilla adenovirus (ChAd, AdCh, or SAdV) or rhesus adenovirus (rhAd). Preferably, an adenovirus vector is a recombinant human adenovirus vector, for instance a recombinant human adenovirus serotype 26, or any one of recombinant human adenovirus serotype 5, 4, 35, 7, 48, etc. In other embodiments, an adenovirus vector is a rhAd vector, e.g. rhAd51, rhAd52 or rhAd53. A recombinant viral vector useful for the application can be prepared using methods known in the art in view of the present disclosure. For example, in view of the degeneracy of the genetic code, several nucleic acid sequences can be designed that encode the same polypeptide. A polynucleotide encoding an HBV antigen of the application can optionally be codon-optimized to ensure proper expression in the host cell (e.g., bacterial or mammalian cells). Codon-optimization is a technology widely applied in the art, and methods for obtaining codon-optimized polynucleotides will be well known to those skilled in the art in view of the present disclosure.

A vector of the application, e.g., a DNA plasmid or a viral vector (particularly an adenoviral vector), can comprise any regulatory elements to establish conventional function(s) of the vector, including but not limited to replication and expression of the HBV antigen(s) encoded by the polynucleotide sequence of the vector. Regulatory elements include, but are not limited to, a promoter, an enhancer, a polyadenylation signal, translation stop codon, a ribosome binding element, a transcription terminator, selection markers, origin of replication, etc. A vector can comprise one or more expression cassettes. An "expression cassette" is part of a vector that directs the cellular machinery to make RNA and protein. An expression cassette typically comprises three components: a promoter sequence, an open reading frame, and a 3'-untranslated region (UTR) optionally comprising a polyadenylation signal. An open reading frame (ORF) is a reading frame that contains a coding sequence of a protein of interest (e.g., HBV antigen) from a start codon to a stop codon. Regulatory elements of the expression cassette can be operably linked to a polynucleotide sequence encoding an HBV antigen of interest. As used herein, the term "operably linked" is to be taken in its broadest reasonable context, and refers to a linkage of polynucleotide elements in a functional relationship. A polynucleotide is "operably linked" when it is placed into a functional relationship with another polynucleotide. For instance, a promoter is operably linked to a coding sequence if it affects the transcription of the coding sequence. Any components suitable for use in an expression cassette described herein can be used in any combination and in any order to prepare vectors of the application.

A vector can comprise a promoter sequence, preferably within an expression cassette, to control expression of an HBV antigen of interest. The term "promoter" is used in its conventional sense, and refers to a nucleotide sequence that initiates the transcription of an operably linked nucleotide sequence. A promoter is located on the same strand near the nucleotide sequence it transcribes. Promoters can be a constitutive, inducible, or repressible. Promoters can be naturally occurring or synthetic. A promoter can be derived from sources including viral, bacterial, fungal, plants, insects, and animals. A promoter can be a homologous promoter (i.e., derived from the same genetic source as the vector) or a heterologous promoter (i.e., derived from a different vector or genetic source). For example, if the vector to be employed is a DNA plasmid, the promoter can be endogenous to the plasmid (homologous) or derived from other sources (heterologous). Preferably, the promoter is located upstream of the polynucleotide encoding an HBV antigen within an expression cassette.

Examples of promoters that can be used include, but are not limited to, a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter (CMV-IE), Epstein Barr virus (EBV) promoter, or a Rous sarcoma virus (RSV) promoter. A promoter can also be a promoter from a human gene such as human actin, human myosin, human hemoglobin, human muscle creatine, or human metalothionein. A promoter can also be a tissue specific promoter, such as a muscle or skin specific promoter, natural or synthetic.

Preferably, a promoter is a strong eukaryotic promoter, preferably a cytomegalovirus immediate early (CMV-IE) promoter. A nucleotide sequence of an exemplary CMV-IE promoter is shown in SEQ ID NO: 7 and SEQ ID NO: 17.

A vector can comprise additional polynucleotide sequences that stabilize the expressed transcript, enhance nuclear export of the RNA transcript, and/or improve transcriptional-translational coupling. Examples of such sequences include polyadenylation signals and enhancer sequences. A polyadenylation signal is typically located downstream of the coding sequence for a protein of interest (e.g., an HBV antigen) within an expression cassette of the vector. Enhancer sequences are regulatory DNA sequences that, when bound by transcription factors, enhance the transcription of an associated gene. An enhancer sequence is preferably located upstream of the polynucleotide sequence encoding an HBV antigen, but downstream of a promoter sequence within an expression cassette of the vector.

Any polyadenylation signal known to those skilled in the art in view of the present disclosure can be used. For example, the polyadenylation signal can be a SV40 polyadenylation signal (e.g., SEQ ID NO: 24), LTR polyadenylation signal, bovine growth hormone (bGH) polyadenylation signal, human growth hormone (hGH) polyadenylation signal, or human β-globin polyadenylation signal. Preferably, a polyadenylation signal is a bovine growth hormone (bGH) polyadenylation signal or a SV40 polyadenylation signal. A nucleotide sequence of an exemplary bGH polyadenylation signal is shown in SEQ ID NO: 11. A nucleotide sequence of an exemplary SV40 polyadenylation signal is shown in SEQ ID NO: 24.

Any enhancer sequence known to those skilled in the art in view of the present disclosure can be used. For example, an enhancer sequence can be a human actin, human myosin, human hemoglobin, human muscle creatine, or a viral enhancer, such as one from CMV, HA, RSV, or EBV. Examples of particular enhancers include, but are not limited to, Woodchuck HBV Post-transcriptional regulatory element (WPRE), intron/exon sequence derived from human apolipoprotein A1 precursor (ApoAI), untranslated R-U5 domain of the human T-cell leukemia virus type 1 (HTLV-1) long terminal repeat (LTR), a splicing enhancer, a synthetic rabbit β-globin intron, or any combination thereof. Preferably, an enhancer sequence is a composite sequence of three consecutive elements of the untranslated R-U5 domain of HTLV-1 LTR, rabbit β-globin intron, and a splicing enhancer, which is referred to herein as "a triple enhancer sequence." A nucleotide sequence of an exemplary triple enhancer sequence is shown in SEQ ID NO: 8. Another exemplary enhancer sequence is an ApoAI gene fragment shown in SEQ ID NO: 23.

A vector can comprise a polynucleotide sequence encoding a signal peptide sequence. Preferably, the polynucleotide sequence encoding the signal peptide sequence is located upstream of the polynucleotide sequence encoding an HBV antigen. Signal peptides typically direct localization of a protein, facilitate secretion of the protein from the cell in which it is produced, and/or improve antigen expression and cross-presentation to antigen-presenting cells. A signal peptide can be present at the N-terminus of an HBV antigen when expressed from the vector, but is cleaved off by signal peptidase, e.g., upon secretion from the cell. An expressed protein in which a signal peptide has been cleaved is often referred to as the "mature protein." Any signal peptide known in the art in view of the present disclosure can be used. For example, a signal peptide can be a cystatin S signal peptide; an immunoglobulin (Ig) secretion signal, such as the Ig heavy chain gamma signal peptide SPIgG or the Ig heavy chain epsilon signal peptide SPIgE.

Preferably, a signal peptide sequence is a cystatin S signal peptide. Exemplary nucleic acid and amino acid sequences of a cystatin S signal peptide are shown in SEQ ID NOs: 5 and 6, respectively. Exemplary nucleic acid and amino acid sequences of an immunoglobulin secretion signal are shown in SEQ ID NOs: 18 and 19, respectively.

A vector, such as a DNA plasmid, can also include a bacterial origin of replication and an antibiotic resistance expression cassette for selection and maintenance of the plasmid in bacterial cells, e.g., E. coli. Bacterial origins of replication and antibiotic resistance cassettes can be located in a vector in the same orientation as the expression cassette encoding an HBV antigen, or in the opposite (reverse) orientation. An origin of replication (ORI) is a sequence at which replication is initiated, enabling a plasmid to reproduce and survive within cells. Examples of ORIs suitable for use in the application include, but are not limited to ColE1, pMB1, pUC, pSC101, R6K, and 15A, preferably pUC. An exemplary nucleotide sequence of a pUC ORI is shown in SEQ ID NO: 10.

Expression cassettes for selection and maintenance in bacterial cells typically include a promoter sequence operably linked to an antibiotic resistance gene. Preferably, the promoter sequence operably linked to an antibiotic resistance gene differs from the promoter sequence operably linked to a polynucleotide sequence encoding a protein of interest, e.g., HBV antigen. The antibiotic resistance gene can be codon optimized, and the sequence composition of the antibiotic resistance gene is normally adjusted to bacterial, e.g., E. coli, codon usage. Any antibiotic resistance gene known to those skilled in the art in view of the present disclosure can be used, including, but not limited to, kanamycin resistance gene (Kan$^r$), ampicillin resistance gene (Amp$^r$), and tetracycline resistance gene (Tet$^r$), as well as genes conferring resistance to chloramphenicol, bleomycin, spectinomycin, carbenicillin, etc.

Preferably, an antibiotic resistance gene in the antibiotic expression cassette of a vector is a kanamycin resistance gene (Kan$^r$). The sequence of Kan$^r$ gene is shown in SEQ ID NO: 13. Preferably, the Kan$^r$ gene is codon optimized. An exemplary nucleic acid sequence of a codon optimized Kan$^r$ gene is shown in SEQ ID NO: 12. The Kan$^r$ can be operably linked to its native promoter, or the Kan$^r$ gene can be linked to a heterologous promoter. In a particular embodiment, the Kan$^r$ gene is operably linked to the ampicillin resistance gene (Amp') promoter, known as the bla promoter. An exemplary nucleotide sequence of a bla promoter is shown in SEQ ID NO: 9.

In a particular embodiment of the application, a vector is a DNA plasmid comprising an expression cassette including a polynucleotide encoding at least one of an HBV antigen selected from the group consisting of an HBV pol antigen comprising an amino acid sequence at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4, and a truncated HBV core antigen consisting of the amino acid sequence of SEQ ID NO: 2; an upstream sequence operably linked to the polynucleotide encoding the HBV antigen comprising, from 5' end to 3' end, a promoter sequence, preferably a CMV promoter sequence of SEQ ID NO: 7, an enhancer sequence, preferably a triple enhancer sequence of SEQ ID NO: 8, and a polynucleotide sequence encoding a signal peptide sequence, preferably a cystatin S signal peptide having the amino acid sequence of SEQ ID NO: 6; and a downstream sequence operably linked to the polynucleotide encoding the HBV antigen comprising a polyadenylation signal, preferably a bGH polyadenylation signal of SEQ ID NO: 11. Such vector further comprises an antibiotic resistance expression cassette including a polynucleotide encoding an antibiotic resistance gene, preferably a Kan$^r$ gene, more preferably a codon optimized Kan$^r$ gene that is at least 90% identical to SEQ ID NO: 12, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 12, preferably 100% identical to SEQ ID NO: 12, operably linked to an Amp$^r$ (bla) promoter of SEQ ID NO: 9, upstream of and operably linked to the polynucleotide encoding the antibiotic resistance gene; and an origin of replication, preferably a pUC ori of SEQ ID NO: 10.

Figure 2G:
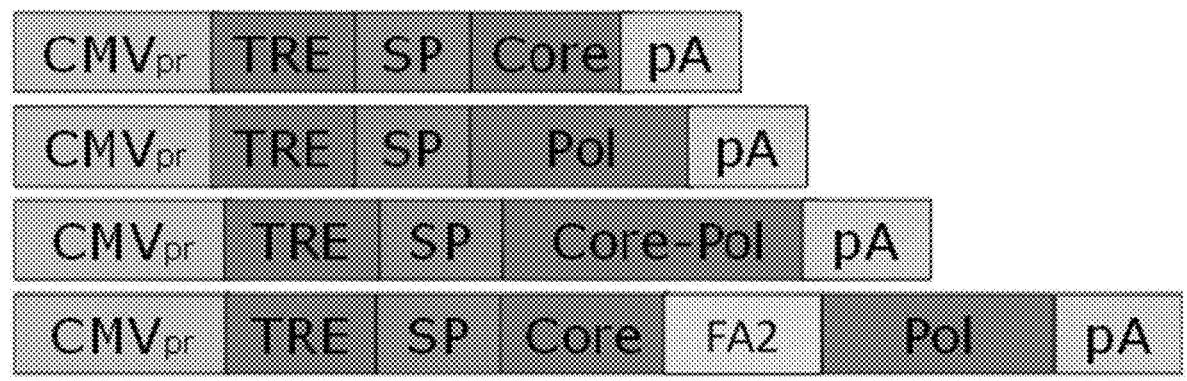
Figure 2H:
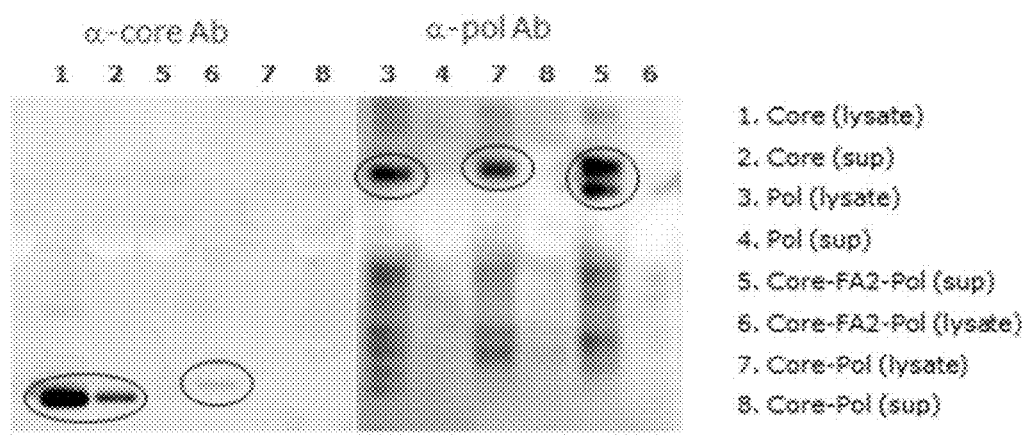

Preferably, the antibiotic resistance cassette and the origin of replication are present in the plasmid in the reverse orientation relative to the HBV antigen expression cassette. Exemplary DNA plasmids comprising the above mentioned features are shown in FIGS. 2A and 2B.

In another particular embodiment of the application, a vector is a viral vector, preferably an adenoviral vector, more preferably an Ad26 or Ad35 vector, comprising an expression cassette including a polynucleotide encoding at least one of an HBV antigen selected from the group consisting of an HBV pol antigen comprising an amino acid sequence at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4, and a truncated HBV core antigen consisting of the amino acid sequence of SEQ ID NO: 14; an upstream sequence operably linked to the polynucleotide encoding the HBV antigen comprising, from 5' end to 3' end, a promoter sequence, preferably a CMV promoter sequence of SEQ ID NO: 17, an enhancer sequence, preferably an ApoAI gene fragment sequence of SEQ ID NO: 23, and a polynucleotide sequence encoding a signal peptide sequence, preferably an immunoglobulin secretion signal having the amino acid sequence of SEQ ID NO: 19; and a downstream sequence operably linked to the polynucleotide encoding the HBV antigen comprising a polyadenylation signal, preferably a SV40 polyadenylation signal of SEQ ID NO: 24.

In an embodiment of the application, a vector, such as a plasmid DNA vector or a viral vector (preferably an adenoviral vector, more preferably an Ad26 or Ad35 vector), encodes an HBV Pol antigen having the amino acid sequence of SEQ ID NO: 4. Preferably, the vector comprises a coding sequence for the HBV Pol antigen that is at least 90% identical to the polynucleotide sequence of SEQ ID NO: 3, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3, preferably 100% identical to SEQ ID NO: 3.

In an embodiment of the application, a vector, such as a plasmid DNA vector or a viral vector (preferably an adenoviral vector, more preferably an Ad26 or Ad35 vector), encodes a truncated HBV core antigen consisting of the amino acid sequence of SEQ ID NO: 2 or SEQ ID NO: 14. Preferably, the vector comprises a coding sequence for the truncated HBV core antigen that is at least 90% identical to the polynucleotide sequence of SEQ ID NO: 1 or SEQ ID NO: 15, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15, preferably 100% identical to SEQ ID NO: 1 or SEQ ID NO: 15.

In yet another embodiment of the application, a vector, such as a plasmid DNA vector or a viral vector (preferably an adenoviral vector, more preferably an Ad26 or Ad35 vector), encodes a fusion protein comprising an HBV Pol antigen having the amino acid sequence of SEQ ID NO: 4 and a truncated HBV core antigen consisting of the amino acid sequence of SEQ ID NO: 2 or SEQ ID NO: 14. Preferably, the vector comprises a coding sequence for the fusion, which contains a coding sequence for the truncated HBV core antigen at least 90% identical to SEQ ID NO: 1 or SEQ ID NO: 15, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15, preferably 98%, 99% or 100% identical to SEQ ID NO: 1 or SEQ ID NO: 15, more preferably SEQ ID NO: 15, operably linked to a coding sequence for the HBV Pol antigen at least 90% identical to SEQ ID NO: 3 or SEQ ID NO: 16, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3 or SEQ ID NO: 16, preferably 98%, 99% or 100% identical to SEQ ID NO: 3 or SEQ ID NO: 16, more preferably SEQ ID NO: 16. Preferably, the coding sequence for the truncated HBV core antigen is operably linked to the coding sequence for the HBV Pol antigen via a coding sequence for a linker at least 90% identical to SEQ ID NO: 22, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 22, preferably 98%, 99% or 100% identical to SEQ ID NO: 22. In particular embodiments of the application, a vector comprises a coding sequence for the fusion having SEQ ID NO: 15 operably linked to SEQ ID NO: 22, which is further operably linked to SEQ ID NO: 16.

The polynucleotides and expression vectors encoding the HBV antigens of the application can be made by any method known in the art in view of the present disclosure. For example, a polynucleotide encoding an HBV antigen can be introduced or "cloned" into an expression vector using standard molecular biology techniques, e.g., polymerase chain reaction (PCR), etc., which are well known to those skilled in the art.

Cells, Polypeptides and Antibodies

The application also provides cells, preferably isolated cells, comprising any of the polynucleotides and vectors described herein. The cells can, for instance, be used for recombinant protein production, or for the production of viral particles.

Embodiments of the application thus also relate to a method of making an HBV antigen of the application. The method comprises transfecting a host cell with an expression vector comprising a polynucleotide encoding an HBV antigen of the application operably linked to a promoter, growing the transfected cell under conditions suitable for expression of the HBV antigen, and optionally purifying or isolating the HBV antigen expressed in the cell. The HBV antigen can be isolated or collected from the cell by any method known in the art including affinity chromatography, size exclusion chromatography, etc. Techniques used for recombinant protein expression will be well known to one of ordinary skill in the art in view of the present disclosure. The expressed HBV antigens can also be studied without purifying or isolating the expressed protein, e.g., by analyzing the supernatant of cells transfected with an expression vector encoding the HBV antigen and grown under conditions suitable for expression of the HBV antigen.

Thus, also provided are non-naturally occurring or recombinant polypeptides comprising an amino acid sequence that is at least 90% identical to the amino acid sequence of SEQ ID NO: 2, SEQ ID NO: 14, or SEQ ID NO: 4. As described above and below, isolated nucleic acid molecules encoding these sequences, vectors comprising these sequences operably linked to a promoter, and compositions comprising the polypeptide, polynucleotide, or vector are also contemplated by the application.

In an embodiment of the application, a recombinant polypeptide comprises an amino acid sequence that is at least 90% identical to the amino acid sequence of SEQ ID NO: 2, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 2. Preferably, a non-naturally occurring or recombinant polypeptide consists of SEQ ID NO: 2.

In another embodiment of the application, a non-naturally occurring or recombinant polypeptide comprises an amino acid sequence that is at least 90% identical to the amino acid sequence of SEQ ID NO: 4, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4. Preferably, a non-naturally occurring or recombinant polypeptide comprises SEQ ID NO: 4.

In another embodiment of the application, a non-naturally occurring or recombinant polypeptide comprises an amino acid sequence that is at least 90% identical to the amino acid sequence of SEQ ID NO: 14, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 14. Preferably, a non-naturally occurring or recombinant polypeptide consists of SEQ ID NO: 14.

Also provided are antibodies or antigen binding fragments thereof that specifically bind to a non-naturally occurring polypeptide of the application. In an embodiment of the application, an antibody specific to a non-naturally occurring HBV antigen of the application does not bind specifically to another HBV antigen. For example, an antibody of the application that binds specifically to an HBV Pol antigen having the amino acid sequence of SEQ ID NO: 4 will not bind specifically to an HBV Pol antigen not having the amino acid sequence of SEQ ID NO: 4.

As used herein, the term "antibody" includes polyclonal, monoclonal, chimeric, humanized, Fv, Fab and F(ab')2; bifunctional hybrid (e.g., Lanzavecchia et al., Eur. J. Immunol. 17:105, 1987), single-chain (Huston et al., Proc. Natl. Acad. Sci. USA 85:5879, 1988; Bird et al., Science 242:423, 1988); and antibodies with altered constant regions (e.g., U.S. Pat. No. 5,624,821).

As used herein, an antibody that "specifically binds to" an antigen refers to an antibody that binds to the antigen with a KD of $1\times10^{-7}$ M or less. Preferably, an antibody that "specifically binds to" an antigen binds to the antigen with a KD of $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods known in the art in view of the present disclosure. For example, the KD of an antibody can be determined by using surface plasmon resonance, such as by using a biosensor system, e.g., a Biacore® system, or by using bio-layer interferometry technology, such as a Octet RED96 system.

The smaller the value of the KD of an antibody, the higher affinity that the antibody binds to a target antigen.

Compositions, Immunogenic Combinations, and Vaccines

The application also relates to compositions, immunogenic combinations, more particularly kits, and vaccines comprising one or more HBV antigens, polynucleotides, and/or vectors encoding one more HBV antigens according to the application. Any of the HBV antigens, polynucleotides (including RNA and DNA), and/or vectors of the application described herein can be used in the compositions, immunogenic combinations or kits, and vaccines of the application.

The application provides a composition comprising an isolated or non-naturally occurring nucleic acid molecule (DNA or RNA) encoding a truncated HBV core antigen consisting of an amino acid sequence that is at least 90% identical to SEQ ID NO: 2 or SEQ ID NO: 14, or a HBV polymerase antigen comprising an amino acid sequence that is at least 90% identical to SEQ ID NO: 4, a vector comprising the isolated or non-naturally occurring nucleic acid molecule, and/or an isolated or non-naturally occurring polypeptide encoded by the isolated or non-naturally occurring nucleic acid molecule.

In an embodiment of the application, a composition comprises an isolated or non-naturally occurring nucleic acid molecule (DNA or RNA) encoding a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14.

In an embodiment of the application, a composition comprises an isolated or non-naturally occurring nucleic acid molecule (DNA or RNA) encoding a HBV Pol antigen comprising an amino acid sequence that is at least 90% identical to SEQ ID NO: 4, preferably 100% identical to SEQ ID NO: 4.

In an embodiment of the application, a composition comprises an isolated or non-naturally occurring nucleic acid molecule (DNA or RNA) comprising a polynucleotide sequence encoding a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14; and an isolated or non-naturally occurring nucleic acid molecule (DNA or RNA) comprising a polynucleotide sequence encoding a HBV Pol antigen comprising an amino acid sequence that is at least 90% identical to SEQ ID NO: 4, preferably 100% identical to SEQ ID NO: 4. The coding sequences for the truncated HBV core antigen and the HBV Pol antigen can be present in the same isolated or non-naturally occurring nucleic acid molecule (DNA or RNA), or in two different isolated or non-naturally occurring nucleic acid molecules (DNA or RNA).

In an embodiment of the application, a composition comprises a vector, preferably a DNA plasmid or a viral vector (such as an adenoviral vector) comprising a polynucleotide encoding a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14.

In an embodiment of the application, a composition comprises a vector, preferably a DNA plasmid or a viral vector (such as an adenoviral vector), comprising a polynucleotide encoding a HBV Pol antigen comprising an amino acid sequence that is at least 90% identical to SEQ ID NO: 4, preferably 100% identical to SEQ ID NO: 4.

In an embodiment of the application, a composition comprises a vector, preferably a DNA plasmid or a viral vector (such as an adenoviral vector), comprising a polynucleotide encoding a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14; and a vector, preferably a DNA plasmid or a viral vector (such as an adenoviral vector), comprising a polynucleotide encoding a HBV Pol antigen comprising an amino acid sequence that is at least 90% identical to SEQ ID NO: 4, preferably 100% identical to SEQ ID NO: 4. The vector comprising the coding sequence for the truncated HBV core antigen and the vector comprising the coding sequence for the HBV Pol antigen can be the same vector, or two different vectors.

In an embodiment of the application, a composition comprises a vector, preferably a DNA plasmid or a viral vector (such as an adenoviral vector), comprising a polynucleotide encoding a fusion protein comprising a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14, operably linked to a HBV Pol antigen comprising an amino acid sequence that is at least 90% identical to SEQ ID NO: 4, preferably 100% identical to SEQ ID NO: 4, or vice versa. Preferably, the fusion protein further comprises a linker that operably links the truncated HBV core antigen to the HBV Pol antigen, or vice versa. Preferably, the linker has the amino acid sequence of (AlaGly)$_n$, wherein n is an integer of 2 to 5.

In an embodiment of the application, a composition comprises an isolated or non-naturally occurring truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14.

In an embodiment of the application, a composition comprises an isolated or non-naturally occurring HBV Pol antigen comprising an amino acid sequence that is at least 90% identical to SEQ ID NO: 4, preferably 100% identical to SEQ ID NO: 4.

In an embodiment of the application, a composition comprises an isolated or non-naturally occurring truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14; and an isolated or non-naturally occurring HBV Pol antigen comprising an amino acid sequence that is at least 90% identical to SEQ ID NO: 4, preferably 100% identical to SEQ ID NO: 4.

In an embodiment of the application, a composition comprises an isolated or non-naturally occurring fusion protein comprising a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14, operably linked to a HBV Pol antigen comprising an amino acid sequence that is at least 90% identical to SEQ ID NO: 4, preferably 100% identical to SEQ ID NO: 4, or vice versa. Preferably, the fusion protein further comprises a linker that operably links the truncated HBV core antigen to the HBV Pol antigen, or vice versa. Preferably, the linker has the amino acid sequence of (AlaGly)$_n$, wherein n is an integer of 2 to 5.

The application also relates to an immunogenic combination or a kit comprising polynucleotides expressing a truncated HBV core antigen and an HBV pol antigen according to embodiments of the application. Any polynucleotides and/or vectors encoding HBV core and pol antigens of the application described herein can be used in the immunogenic combinations or kits of the application.

According to embodiments of the application, a vaccine combination or kit comprises:
(a) a first non-naturally occurring nucleic acid molecule comprising a first polynucleotide encoding a HBV polymerase antigen having an amino acid sequence that is at least 98% identical to SEQ ID NO: 4, wherein the HBV polymerase antigen does not have reverse transcriptase activity and RNase H activity;
(b) a second non-naturally occurring nucleic acid molecule comprising a second polynucleotide encoding a truncated HBV core antigen consisting of the amino acid sequence of SEQ ID NO: 2 or SEQ ID NO: 14; and
(c) a pharmaceutically acceptable carrier, wherein the first non-naturally occurring nucleic acid molecule and the second non-naturally occurring nucleic acid molecule are present in the same non-naturally occurring nucleic acid molecule or in two different non-naturally occurring nucleic acid molecules.

According to embodiments of the application, the polynucleotides in a vaccine combination or kit can be linked or separate, such that the HBV antigens expressed from such polynucleotides are fused together or produced as separate proteins, whether expressed from the same or different polynucleotides. In an embodiment, the first and second polynucleotides are present in separate vectors, e.g., DNA plasmids or viral vectors, used in combination either in the same or separate compositions, such that the expressed proteins are also separate proteins, but used in combination. In another embodiment, the HBV antigens encoded by the first and second polynucleotides can be expressed from the same vector, such that an HBV core-pol fusion antigen is produced. Optionally, the core and pol antigens can be joined or fused together by a short linker. Alternatively, the HBV antigens encoded by the first and second polynucleotides can be expressed independently from a single vector using a using a ribosomal slippage site (also known as cis-hydrolase site) between the core and pol antigen coding sequences. This strategy results in a bicistronic expression vector in which individual core and pol antigens are produced from a single mRNA transcript. The core and pol antigens produced from such a bicistronic expression vector can have additional N or C-terminal residues, depending upon the ordering of the coding sequences on the mRNA transcript. Examples of ribosomal slippage sites that can be used for this purpose include, but are not limited to, the FA2 slippage site from foot-and-mouth disease virus (FMDV). Another possibility is that the HBV antigens encoded by the first and second polynucleotides can be expressed independently from two separate vectors, one encoding the HBV core antigen and one encoding the HBV pol antigen.

In a preferred embodiment, the first and second polynucleotides are present in separate vectors, e.g., DNA plasmids or viral vectors. Preferably, the separate vectors are present in the same composition.

According to preferred embodiments of the application, an immunogenic combination or kit comprises a first polynucleotide present in a first vector and a second polynucleotide present in a second vector. The first and second vectors can be the same or different. Preferably the vectors are DNA plasmids.

In a particular embodiment of the application, an immunogenic combination or kit comprises: a first vector comprising a polynucleotide encoding a truncated HBV core antigen consisting of an amino acid sequence that is at least 90% identical to SEQ ID NO: 2, preferably 100% identical to SEQ ID NO: 2; and a second vector comprising a polynucleotide encoding a HBV polymerase antigen comprising an amino acid sequence that is at least 98% identical to SEQ ID NO: 4, preferably 100% identical to SEQ ID NO: 4.

In a particular embodiment of the application, the first vector is a first DNA plasmid and the second vector is a second DNA plasmid. Each of the first and second DNA plasmids comprises an origin of replication, preferably pUC ORI of SEQ ID NO: 10, and an antibiotic resistance cassette, preferably comprising a codon optimized Kan$^r$ gene having a polynucleotide sequence that is at least 90% identical to SEQ ID NO: 12, preferably under control of a bla promoter, for instance the bla promoter shown in SEQ ID NO: 9. Each of the first and second DNA plasmids independently further comprises at least one of a promoter sequence, enhancer sequence, and a polynucleotide sequence encoding a signal peptide sequence operably linked to the first polynucleotide sequence or the second polynucleotide sequence. Preferably, each of the first and second DNA plasmids comprises an upstream sequence operably linked to the first polynucleotide or the second polynucleotide, wherein the upstream sequence comprises, from 5' end to 3' end, a promoter sequence of SEQ ID NO: 7, an enhancer sequence of SEQ ID NO: 8, and a polynucleotide sequence encoding a signal peptide sequence having the amino acid sequence of SEQ ID NO: 6. Each of the first and second DNA plasmids can also comprise a polyadenylation signal located downstream of the coding sequence of the HBV antigen, such as the bGH polyadenylation signal of SEQ ID NO: 11.

In one particular embodiment of the application, the first vector is a first viral vector and the second vector is a second viral vector. Preferably, each of the first and second viral vector is an adenoviral vector, more preferably an Ad26 or Ad35 vector, comprising an expression cassette including the polynucleotide encoding an HBV pol antigen or a truncated HBV core antigen of the application; an upstream sequence operably linked to the polynucleotide encoding the HBV antigen comprising, from 5' end to 3' end, a promoter sequence, preferably a CMV promoter sequence of SEQ ID NO: 17, an enhancer sequence, preferably an ApoAI gene fragment sequence of SEQ ID NO: 23, and a polynucleotide sequence encoding a signal peptide sequence, preferably an immunoglobulin secretion signal having the amino acid sequence of SEQ ID NO: 19; and a downstream sequence operably linked to the polynucleotide encoding the HBV antigen comprising a polyadenylation signal, preferably a SV40 polyadenylation signal of SEQ ID NO: 24.

In another preferred embodiment, the first and second polynucleotides are present in a single vector, e.g., DNA plasmid or viral vector. Preferably, the single vector is an adenoviral vector, more preferably an Ad26 vector, comprising an expression cassette including a polynucleotide encoding an HBV pol antigen and a truncated HBV core antigen of the application, preferably encoding an HBV pol antigen and a truncated HBV core antigen of the application as a fusion protein; an upstream sequence operably linked to the polynucleotide encoding the HBV pol and truncated core antigens comprising, from 5' end to 3' end, a promoter sequence, preferably a CMV promoter sequence of SEQ ID NO: 17, an enhancer sequence, preferably an ApoAI gene fragment sequence of SEQ ID NO: 23, and a polynucleotide sequence encoding a signal peptide sequence, preferably an immunoglobulin secretion signal having the amino acid sequence of SEQ ID NO: 19; and a downstream sequence operably linked to the polynucleotide encoding the HBV antigen comprising a polyadenylation signal, preferably a SV40 polyadenylation signal of SEQ ID NO: 24

When an immunogenic combination of the application comprises a first vector, such as a DNA plasmid or viral vector, and a second vector, such as a DNA plasmid or viral vector, the amount of each of the first and second vectors is not particularly limited. For example, the first DNA plasmid and the second DNA plasmid can be present in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second DNA plasmids are present in a ratio of 1:1, by weight.

Compositions and immunogenic combinations of the application can comprise additional polynucleotides or vectors encoding additional HBV antigens and/or additional HBV antigens or immunogenic fragments thereof. However, in particular embodiments, the compositions and immunogenic combinations of the application do not comprise certain antigens.

In a particular embodiment, a composition or immunogenic combination or kit of the application does not comprise a HBsAg or a polynucleotide sequence encoding the HBsAg.

In another particular embodiment, a composition or immunogenic combination or kit of the application does not comprise a HBV L protein or a polynucleotide sequence encoding the HBV L protein.

In yet another particular embodiment of the application, a composition or immunogenic combination of the application does not comprise a HBV envelope protein or a polynucleotide sequence encoding the HBV envelope protein.

Compositions and immunogenic combinations of the application can also comprise a pharmaceutically acceptable carrier. A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. Pharmaceutically acceptable carriers can include vehicles, such as lipid (nano)particles. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions and immunogenic combinations of the application can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the application can also be formulated for other routes of administration including transmucosal, ocular, rectal, long acting implantation, sublingual administration, under the tongue, from oral mucosa bypassing the portal circulation, inhalation, or intranasal.

In a preferred embodiment of the application, compositions and immunogenic combinations of the application are formulated for parental injection, preferably subcutaneous, intradermal injection, or intramuscular injection, more preferably intramuscular injection.

According to embodiments of the application, compositions and immunogenic combinations for administration will typically comprise a buffered solution in a pharmaceutically acceptable carrier, e.g., an aqueous carrier such as buffered saline and the like, e.g., phosphate buffered saline (PBS). The compositions and immunogenic combinations can also contain pharmaceutically acceptable substances as required to approximate physiological conditions such as pH adjusting and buffering agents. For example, a composition or immunogenic combination of the application comprising plasmid DNA can contain phosphate buffered saline (PBS) as the pharmaceutically acceptable carrier. The plasmid DNA can be present in a concentration of, e.g., 0.5 mg/mL to 5 mg/mL, such as 0.5 mg/mL 1, mg/mL, 2 mg/mL, 3 mg/mL, 4 mg/mL, or 5 mg/mL, preferably at 1 mg/mL.

Compositions and immunogenic combinations of the application can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

In a particular embodiment of the application, a composition or immunogenic combination is a DNA vaccine. DNA vaccines typically comprise bacterial plasmids containing a polynucleotide encoding an antigen of interest under control of a strong eukaryotic promoter. Once the plasmids are delivered to the cell cytoplasm of the host, the encoded antigen is produced and processed endogenously. The resulting antigen typically induces both humoral and cell-medicated immune responses. DNA vaccines are advantageous at least because they offer improved safety, are temperature stable, can be easily adapted to express antigenic variants, and are simple to produce. Any of the DNA plasmids of the application can be used to prepare such a DNA vaccine.

In other particular embodiments of the application, a composition or immunogenic combination is an RNA vaccine. RNA vaccines typically comprise at least one single-stranded RNA molecule encoding an antigen of interest, e.g., HBV antigen. Once the RNA is delivered to the cell cytoplasm of the host, the encoded antigen is produced and processed endogenously, inducing both humoral and cell-mediated immune responses, similar to a DNA vaccine. The RNA sequence can be codon optimized to improve translation efficiency. The RNA molecule can be modified by any method known in the art in view of the present disclosure to enhance stability and/or translation, such by adding a polyA tail, e.g., of at least 30 adenosine residues; and/or capping the 5-end with a modified ribonucleotide, e.g., 7-methyl-guanosine cap, which can be incorporated during RNA synthesis or enzymatically engineered after RNA transcription. An RNA vaccine can also be a self-replicating RNA vaccine developed from an alphavirus expression vector. Self-replicating RNA vaccines comprise a replicase RNA molecule derived from a virus belonging to the alphavirus family with a subgenomic promoter that controls replication of the HBV antigen RNA followed by an artificial poly A tail located downstream of the replicase.

In certain embodiments, an adjuvant is included in a composition or immunogenic combination of the application, or co-administered with a composition or immunogenic combination of the application. Use of an adjuvant is optional, and can further enhance immune responses when the composition is used for vaccination purposes. Adjuvants suitable for co-administration or inclusion in compositions in accordance with the application should preferably be ones that are potentially safe, well tolerated and effective in humans. An adjuvant can be a small molecule or antibody including, but not limited to, immune checkpoint inhibitors (e.g., anti-PD1, anti-TIM-3, etc.), toll-like receptor agonists (e.g., TLR7 agonists and/or TLR8 agonists), RIG-1 agonists, IL-15 superagonists (Altor Bioscience), mutant IRF3 and IRF7 genetic adjuvants, STING agonists (Aduro), FLT3L genetic adjuvant, IL-12 genetic adjuvant, and IL-7-hyFc. Adjuvants can also e.g., be chosen from among the following anti-HBV agents: HBV DNA polymerase inhibitors; immunomodulators; toll-like receptor 7 modulators; toll-like receptor 8 modulators; toll-like receptor 3 modulators; interferon alpha receptor ligands; hyaluronidase inhibitors; modulators of IL-10; HBsAg inhibitors; toll-like receptor 9 modulators; cyclophilin inhibitors; HBV prophylactic vaccines; HBV therapeutic vaccines; HBV viral entry inhibitors; antisense oligonucleotides targeting viral mRNA, more particularly anti-HBV antisense oligonucleotides; short interfering RNAs (siRNA), more particularly anti-HBV siRNA; endonuclease modulators; inhibitors of ribonucleotide reductase; hepatitis B virus E antigen inhibitors; HBV antibodies targeting the surface antigens of the hepatitis B virus; HBV antibodies; CCR2 chemokine antagonists; thymosin agonists; cytokines, such as IL12; capsid assembly modulators, nucleoprotein inhibitors (HBV core or capsid protein inhibitors); nucleic acid polymers (NAPs); stimulators of retinoic acid-inducible gene 1; stimulators of NOD2; recombinant thymosin alpha-1; hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, and CTLA-4 inhibitors; agonists of co-stimulatory receptors that are expressed on immune cells (more particularly T cells), such as CD27, CD28, etc.; BTK inhibitors; other drugs for treating HBV; IDO inhibitors; arginase inhibitors; and KDM5 inhibitors.

The application also provides methods of making compositions and immunogenic combinations of the application. A method of producing a composition or immunogenic combination comprises mixing an isolated polynucleotide encoding an HBV antigen, vector, and/or polypeptide of the application with one or more pharmaceutically acceptable carriers. One of ordinary skill in the art will be familiar with conventional techniques used to prepare such compositions.

Methods of Inducing an Immune Response

The application also provides methods of inducing an immune response against hepatitis B virus (HBV) in a subject in need thereof, comprising administering to the subject an immunogenically effective amount of a composition or immunogenic composition of the application. Any of the compositions and immunogenic combinations of the application described herein can be used in the methods of the application.

As used herein, the term "infection" refers to the invasion of a host by a disease causing agent. A disease causing agent is considered to be "infectious" when it is capable of invading a host, and replicating or propagating within the host. Examples of infectious agents include viruses, e.g., HBV and certain species of adenovirus, prions, bacteria, fungi, protozoa and the like. "HBV infection" specifically refers to invasion of a host organism, such as cells and tissues of the host organism, by HBV.

The phrase "inducing an immune response" when used with reference to the methods described herein encompasses causing a desired immune response or effect in a subject in need thereof against an infection, e.g., an HBV infection. "Inducing an immune response" also encompasses providing a therapeutic immunity for treating against a pathogenic agent, e.g., HBV. As used herein, the term "therapeutic immunity" or "therapeutic immune response" means that the vaccinated subject is able to control an infection with the pathogenic agent against which the vaccination was done, for instance immunity against HBV infection conferred by vaccination with HBV vaccine. In an embodiment, "inducing an immune response" means producing an immunity in a subject in need thereof, e.g., to provide a therapeutic effect against a disease, such as HBV infection. In certain embodiments, "inducing an immune response" refers to causing or improving cellular immunity, e.g., T cell response, against HBV infection. In certain embodiments, "inducing an immune response" refers to causing or improving a humoral immune response against HBV infection. In certain embodiments, "inducing an immune response" refers to causing or improving a cellular and a humoral immune response against HBV infection.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

Typically, the administration of compositions and immunogenic combinations of the application will have a therapeutic aim to generate an immune response against HBV after HBV infection or development of symptoms characteristic of HBV infection, e.g., for therapeutic vaccination.

As used herein, "an immunogenically effective amount" or "immunologically effective amount" means an amount of a composition, polynucleotide, vector, or antigen sufficient to induce a desired immune effect or immune response in a subject in need thereof. An immunogenically effective amount can be an amount sufficient to induce an immune response in a subject in need thereof. An immunogenically effective amount can be an amount sufficient to produce immunity in a subject in need thereof, e.g., provide a therapeutic effect against a disease such as HBV infection. An immunogenically effective amount can vary depending upon a variety of factors, such as the physical condition of the subject, age, weight, health, etc.; the particular application, e.g., providing protective immunity or therapeutic immunity; and the particular disease, e.g., viral infection, for which immunity is desired. An immunogenically effective amount can readily be determined by one of ordinary skill in the art in view of the present disclosure.

In particular embodiments of the application, an immunogenically effective amount refers to the amount of a composition or immunogenic combination which is sufficient to achieve one, two, three, four, or more of the following effects: (i) reduce or ameliorate the severity of an HBV infection or a symptom associated therewith; (ii) reduce the duration of an HBV infection or symptom associated therewith; (iii) prevent the progression of an HBV infection or symptom associated therewith; (iv) cause regression of an HBV infection or symptom associated therewith; (v) prevent the development or onset of an HBV infection, or symptom associated therewith; (vi) prevent the recurrence of an HBV infection or symptom associated therewith; (vii) reduce hospitalization of a subject having an HBV infection; (viii) reduce hospitalization length of a subject having an HBV infection; (ix) increase the survival of a subject with an HBV infection; (x) eliminate an HBV infection in a subject; (xi) inhibit or reduce HBV replication in a subject; and/or (xii) enhance or improve the prophylactic or therapeutic effect(s) of another therapy.

An immunogenically effective amount can also be an amount sufficient to reduce HBsAg levels consistent with evolution to clinical seroconversion; achieve sustained HBsAg clearance associated with reduction of infected hepatocytes by a subject's immune system; induce HBV-antigen specific activated T-cell populations; and/or achieve persistent loss of HBsAg within 12 months. Examples of a target index include lower HBsAg below a threshold of 500 copies of HBsAg international units (IU) and/or higher CD8 counts.

As general guidance, an immunogenically effective amount when used with reference to a DNA plasmid can range from about 0.1 mg/mL to 10 mg/mL of DNA plasmid total, such as 0.1 mg/mL, 0.25 mg/mL, 0.5 mg/mL. 0.75 mg/mL 1 mg/mL, 1.5 mg/mL, 2 mg/mL, 3 mg/mL, 4 mg/mL, 5 mg/mL, 6 mg/mL, 7 mg/mL, 8 mg/mL, 9 mg/mL, or 10 mg/mL. Preferably, an immunogenically effective amount of DNA plasmid is less than 8 mg/mL, more preferably less than 6 mg/mL, even more preferably 3-4 mg/mL. An immunogenically effective amount can be from one vector or plasmid, or from multiple vectors or plasmids. An immunogenically effective amount can be administered in a single composition, or in multiple compositions, such as 1, 2, 3, 4, 5, 6, 7, 8, 9, or 10 compositions (e.g., tablets, capsules or injectables, or any composition adapted to intradermal delivery, e.g., to intradermal delivery using an intradermal delivery patch), wherein the administration of the multiple capsules or injections collectively provides a subject with an immunogenically effective amount. For example, when two DNA plasmids are used, an immunogenically effective amount can be 3-4 mg/mL, with 1.5-2 mg/mL of each plasmid. It is also possible to administer an immunogenically effective amount to a subject, and subsequently administer another dose of an immunogenically effective amount to the same subject, in a so-called prime-boost regimen. This general concept of a prime-boost regimen is well known to the skilled person in the vaccine field. Further booster administrations can optionally be added to the regimen, as needed.

An immunogenic combination comprising two DNA plasmids, e.g., a first DNA plasmid encoding an HBV core antigen and second DNA plasmid encoding an HBV pol antigen can be administered to a subject by mixing both plasmids and delivering the mixture to a single anatomic site. Alternatively, two separate immunizations each delivering a single expression plasmid can be performed. In such embodiments, whether both plasmids are administered in a single immunization as a mixture or in two separate immunizations, the first DNA plasmid and the second DNA plasmid can be administered in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second DNA plasmids are administered in a ratio of 1:1, by weight.

Preferably, a subject to be treated according to the methods of the application is an HBV-infected subject, particular a subject having chronic HBV infection. Acute HBV infection is characterized by an efficient activation of the innate immune system complemented with a subsequent broad adaptive response (e.g., HBV-specific T-cells, neutralizing antibodies), which usually results in successful suppression of replication or removal of infected hepatocytes. In contrast, such responses are impaired or diminished due to high viral and antigen load, e.g., HBV envelope proteins are produced in abundance and can be released in sub-viral particles in 1,000-fold excess to infectious virus.

Chronic HBV infection is described in phases characterized by viral load, liver enzyme levels (necroinflammatory activity), HBeAg, or HBsAg load or presence of antibodies to these antigens. cccDNA levels stay relatively constant at approximately 10 to 50 copies per cell, even though viremia can vary considerably. The persistence of the cccDNA species leads to chronicity. More specifically, the phases of chronic HBV infection include: (i) the immune-tolerant phase characterized by high viral load and normal or minimally elevated liver enzymes; (ii) the immune activation HBeAg-positive phase in which lower or declining levels of viral replication with significantly elevated liver enzymes are observed; (iii) the inactive HBsAg carrier phase, which is a low replicative state with low viral loads and normal liver enzyme levels in the serum that may follow HBeAg seroconversion; and (iv) the HBeAg-negative phase in which viral replication occurs periodically (reactivation) with concomitant fluctuations in liver enzyme levels, mutations in the pre-core and/or basal core promoter are common, such that HBeAg is not produced by the infected cell.

As used herein, "chronic HBV infection" refers to a subject having the detectable presence of HBV for more than 6 months. A subject having a chronic HBV infection can be in any phase of chronic HBV infection. Chronic HBV infection is understood in accordance with its ordinary meaning in the field. Chronic HBV infection can for example be characterized by the persistence of HBsAg for 6 months or more after acute HBV infection. For example, a chronic HBV infection referred to herein follows the definition published by the Centers for Disease Control and Prevention (CDC), according to which a chronic HBV infection can be characterized by laboratory criteria such as: (i) negative for IgM antibodies to hepatitis B core antigen (IgM anti-HBc) and positive for hepatitis B surface antigen (HBsAg), hepatitis B e antigen (HBeAg), or nucleic acid test for hepatitis B virus DNA, or (ii) positive for HBsAg or nucleic acid test for HBV DNA, or positive for HBeAg two times at least 6 months apart.

Preferably, an immunogenically effective amount refers to the amount of a composition or immunogenic combination of the application which is sufficient to treat chronic HBV infection.

In some embodiments, a subject having chronic HBV infection is undergoing nucleoside analog (NUC) treatment, and is NUC-suppressed. As used herein, "NUC-suppressed" refers to a subject having an undetectable viral level of HBV and stable alanine aminotransferase (ALT) levels for at least six months. Examples of nucleoside/nucleotide analog treatment include HBV polymerase inhibitors, such as entecavir and tenofovir. Preferably, a subject having chronic HBV infection does not have advanced hepatic fibrosis or cirrhosis. Such subject would typically have a METAVIR score of less than 3 for fibrosis and a fibroscan result of less than 9 kPa. The METAVIR score is a scoring system that is commonly used to assess the extent of inflammation and fibrosis by histopathological evaluation in a liver biopsy of patients with hepatitis B. The scoring system assigns two standardized numbers: one reflecting the degree of inflammation and one reflecting the degree of fibrosis.

It is believed that elimination or reduction of chronic HBV may allow early disease interception of severe liver disease, including virus-induced cirrhosis and hepatocellular carcinoma. Thus, the methods of the application can also be used as therapy to treat HBV-induced diseases. Examples of HBV-induced diseases include, but are not limited to cirrhosis, cancer (e.g., hepatocellular carcinoma), and fibrosis, particularly advanced fibrosis characterized by a METAVIR score of 3 or higher for fibrosis. In such embodiments, an immunogenically effective amount is an amount sufficient to achieve persistent loss of HBsAg within 12 months and significant decrease in clinical disease (e.g., cirrhosis, hepatocellular carcinoma, etc.).

Methods according to embodiments of the application further comprise administering to the subject in need thereof another immunogenic agent (such as another HBV antigen or other antigen) or another anti-HBV agent (such as a nucleoside analog or other anti-HBV agent) in combination with a composition of the application. For example, another anti-HBV agent or immunogenic agent can be a small molecule or antibody including, but not limited to, immune checkpoint inhibitors (e.g., anti-PD1, anti-TIM-3, etc.), toll-like receptor agonists (e.g., TLR7 agonists and/or TLR8 agonists), RIG-1 agonists, IL-15 superagonists (Altor Bioscience), mutant IRF3 and IRF7 genetic adjuvants, STING agonists (Aduro), FLT3L genetic adjuvant, IL-12 genetic adjuvant, IL-7-hyFc; CAR-T which bind HBV env (S-CAR cells); capsid assembly modulators; cccDNA inhibitors, HBV polymerase inhibitors (e.g., entecavir and tenofovir). The one or more other anti-HBV active agents can be, for example, a small molecule, an antibody or antigen binding fragment thereof, a polypeptide, protein, or nucleic acid. The one or more other anti-HBV agents can e.g., be chosen from among HBV DNA polymerase inhibitors; immunomodulators; toll-like receptor 7 modulators; toll-like receptor 8 modulators; toll-like receptor 3 modulators; interferon alpha receptor ligands; hyaluronidase inhibitors; modulators of IL-10; HBsAg inhibitors; toll-like receptor 9 modulators; cyclophilin inhibitors; HBV prophylactic vaccines; HBV therapeutic vaccines; HBV viral entry inhibitors; antisense oligonucleotides targeting viral mRNA, more particularly anti-HBV antisense oligonucleotides; short interfering RNAs (siRNA), more particularly anti-HBV siRNA; endonuclease modulators; inhibitors of ribonucleotide reductase; hepatitis B virus E antigen inhibitors; HBV antibodies targeting the surface antigens of the hepatitis B virus; HBV antibodies; CCR2 chemokine antagonists; thymosin agonists; cytokines, such as IL12; capsid assembly modulators, nucleoprotein inhibitors (HBV core or capsid protein inhibitors); nucleic acid polymers (NAPs); stimulators of retinoic acid-inducible gene 1; stimulators of NOD2; recombinant thymosin alpha-1; hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, and CTLA-4 inhibitors; agonists of co-stimulatory receptors that are expressed on immune cells (more particularly T cells), such as CD27, CD28, etc.; BTK inhibitors; other drugs for treating HBV; IDO inhibitors; arginase inhibitors; and KDM5 inhibitors.

Methods of Delivery

Compositions and immunogenic combinations of the application can be administered to a subject by any method known in the art in view of the present disclosure, including, but not limited to, parenteral administration (e.g., intramuscular, subcutaneous, intravenous, or intradermal injection), oral administration, transdermal administration, and nasal administration. Preferably, compositions and immunogenic combinations are administered parenterally (e.g., by intramuscular injection or intradermal injection) or transdermally.

In some embodiments of the application in which a composition or immunogenic combination comprises one or more DNA plasmids, administration can be by injection through the skin, e.g., intramuscular or intradermal injection, preferably intramuscular injection. Intramuscular injection can be combined with electroporation, i.e., application of an electric field to facilitate delivery of the DNA plasmids to cells. As used herein, the term "electroporation" refers to the use of a transmembrane electric field pulse to induce microscopic pathways (pores) in a bio-membrane. During in vivo electroporation, electrical fields of appropriate magnitude and duration are applied to cells, inducing a transient state of enhanced cell membrane permeability, thus enabling the cellular uptake of molecules unable to cross cell membranes on their own. Creation of such pores by electroporation facilitates passage of biomolecules, such as plasmids, oligonucleotides, siRNAs, drugs, etc., from one side of a cellular membrane to the other. In vivo electroporation for the delivery of DNA vaccines has been shown to significantly increase plasmid uptake by host cells, while also leading to mild-to-moderate inflammation at the injection site. As a result, transfection efficiency and immune response are significantly improved (e.g., up to 1,000 fold and 100 fold respectively) with intradermal or intramuscular electroporation, in comparison to conventional injection.

In a typical embodiment, electroporation is combined with intramuscular injection. However, it is also possible to combine electroporation with other forms of parenteral administration, e.g., intradermal injection, subcutaneous injection, etc.

Administration of a composition, immunogenic combination or vaccine of the application via electroporation can be accomplished using electroporation devices that can be configured to deliver to a desired tissue of a mammal a pulse of energy effective to cause reversible pores to form in cell membranes. The electroporation device can include an electroporation component and an electrode assembly or handle assembly. The electroporation component can include one or more of the following components of electroporation devices: controller, current waveform generator, impedance tester, waveform logger, input element, status reporting element, communication port, memory component, power source, and power switch. Electroporation can be accomplished using an in vivo electroporation device. Examples of electroporation devices and electroporation methods that can facilitate delivery of compositions and immunogenic combinations of the application, particularly those comprising DNA plasmids, include CELLECTRA® (Inovio Pharmaceuticals, Blue Bell, Pa.), Elgen electroporator (Inovio Pharmaceuticals, Inc.) Tri-Grid™ delivery system (Ichor Medical Systems, Inc., San Diego, Calif. 92121) and those described in U.S. Pat. Nos. 7,664,545, 8,209,006, 9,452,285, 5,273,525, 6,110,161, 6,261,281, 6,958,060, and U.S. Pat. Nos. 6,939,862, 7,328,064, 6,041,252, 5,873,849, 6,278,895, 6,319,901, 6,912,417, 8,187,249, 9,364,664, 9,802,035, 6,117,660, and International Patent Application Publication WO2017172838, all of which are herein incorporated by reference in their entireties. Other examples of in vivo electroporation devices are described in International Patent Application Publication WO2019126120, entitled "Method and Apparatus for the Delivery of Hepatitis B Virus (HBV) Vaccines," filed on the same day as this application, the contents of which are hereby incorporated by reference in their entireties. Also contemplated by the application for delivery of the compositions and immunogenic combinations of the application are use of a pulsed electric field, for instance as described in, e.g., U.S. Pat. No. 6,697,669, which is herein incorporated by reference in its entirety.

In other embodiments of the application in which a composition or immunogenic combination comprises one or more DNA plasmids, the method of administration is transdermal. Transdermal administration can be combined with epidermal skin abrasion to facilitate delivery of the DNA plasmids to cells. For example, a dermatological patch can be used for epidermal skin abrasion. Upon removal of the dermatological patch, the composition or immunogenic combination can be deposited on the abraised skin.

Methods of delivery are not limited to the above described embodiments, and any means for intracellular delivery can be used. Other methods of intracellular delivery contemplated by the methods of the application include, but are not limited to, liposome encapsulation, nanoparticles, etc.

Adjuvants

In some embodiments of the application, a method of inducing an immune response against HBV further comprises administering an adjuvant. The terms "adjuvant" and "immune stimulant" are used interchangeably herein, and are defined as one or more substances that cause stimulation of the immune system. In this context, an adjuvant is used to enhance an immune response to HBV antigens and antigenic HBV polypeptides of the application.

According to embodiments of the application, an adjuvant can be present in an immunogenic combination or composition of the application, or administered in a separate composition. An adjuvant can be, e.g., a small molecule or an antibody. Examples of adjuvants suitable for use in the application include, but are not limited to, immune checkpoint inhibitors (e.g., anti-PD1, anti-TIM-3, etc.), toll-like receptor agonists (e.g., TLR7 and/or TLR8 agonists), RIG-1 agonists, IL-15 superagonists (Altor Bioscience), mutant IRF3 and IRF7 genetic adjuvants, STING agonists (Aduro), FLT3L genetic adjuvant, IL-12 genetic adjuvant, and IL-7-hyFc. Examples of adjuvants can e.g., be chosen from among the following anti-HBV agents: HBV DNA polymerase inhibitors; immunomodulators; toll-like receptor 7 modulators; toll-like receptor 8 modulators; toll-like receptor 3 modulators; interferon alpha receptor ligands; hyaluronidase inhibitors; modulators of IL-10; HBsAg inhibitors; toll-like receptor 9 modulators; cyclophilin inhibitors; HBV prophylactic vaccines; HBV therapeutic vaccines; HBV viral entry inhibitors; antisense oligonucleotides targeting viral mRNA, more particularly anti-HBV antisense oligonucleotides; short interfering RNAs (siRNA), more particularly anti-HBV siRNA; endonuclease modulators; inhibitors of ribonucleotide reductase; hepatitis B virus E antigen inhibitors; HBV antibodies targeting the surface antigens of the hepatitis B virus; HBV antibodies; CCR2 chemokine antagonists; thymosin agonists; cytokines, such as IL12; capsid assembly modulators, nucleoprotein inhibitors (HBV core or capsid protein inhibitors); nucleic acid polymers (NAPs); stimulators of retinoic acid-inducible gene 1; stimulators of NOD2; recombinant thymosin alpha-1; hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, and CTLA-4 inhibitors; agonists of co-stimulatory receptors that are expressed on immune cells (more particularly T cells), such as CD27, CD28, etc.; BTK inhibitors; other drugs for treating HBV; IDO inhibitors; arginase inhibitors; and KDM5 inhibitors.

Compositions and immunogenic combinations of the application can also be administered in combination with at least one other anti-HBV agent. Examples of anti-HBV agents suitable for use with the application include, but are not limited to small molecules, antibodies, and/or CAR-T therapies which bind HBV env (S-CAR cells), capsid assembly modulators, TLR agonists (e.g., TLR7 and/or TLR8 agonists), cccDNA inhibitors, HBV polymerase inhibitors (e.g., entecavir and tenofovir), and/or immune checkpoint inhibitors, etc. The at least one anti-HBV agent can e.g., be chosen from among HBV DNA polymerase inhibitors; immunomodulators; toll-like receptor 7 modulators; toll-like receptor 8 modulators; toll-like receptor 3 modulators; interferon alpha receptor ligands; hyaluronidase inhibitors; modulators of IL-10; HBsAg inhibitors; toll-like receptor 9 modulators; cyclophilin inhibitors; HBV prophylactic vaccines; HBV therapeutic vaccines; HBV viral entry inhibitors; antisense oligonucleotides targeting viral mRNA, more particularly anti-HBV antisense oligonucleotides; short interfering RNAs (siRNA), more particularly anti-HBV siRNA; endonuclease modulators; inhibitors of ribonucleotide reductase; hepatitis B virus E antigen inhibitors; HBV antibodies targeting the surface antigens of the hepatitis B virus; HBV antibodies; CCR2 chemokine antagonists; thymosin agonists; cytokines, such as IL12; capsid assembly modulators, nucleoprotein inhibitors (HBV core or capsid protein inhibitors); nucleic acid polymers (NAPs); stimulators of retinoic acid-inducible gene 1; stimulators of NOD2; recombinant thymosin alpha-1; hepatitis B virus replication inhibitors; PI3K inhibitors; cccDNA inhibitors; immune checkpoint inhibitors, such as PD-L1 inhibitors, PD-1 inhibitors, TIM-3 inhibitors, TIGIT inhibitors, Lag3 inhibitors, and CTLA-4 inhibitors; agonists of co-stimulatory receptors that are expressed on immune cells (more particularly T cells), such as CD27, CD28, etc.; BTK inhibitors; other drugs for treating HBV; IDO inhibitors; arginase inhibitors; and KDM5 inhibitors. Such anti-HBV agents can be administered with the compositions and immunogenic combinations of the application simultaneously or sequentially.

Methods of Prime/Boost Immunization

Embodiments of the application also contemplate administering an immunogenically effective amount of a composition or immunogenic combination to a subject, and subsequently administering another dose of an immunogenically effective amount of a composition or immunogenic combination to the same subject, in a so-called prime-boost regimen Thus, in an embodiment, a composition or immunogenic combination of the application is a primer vaccine used for priming an immune response. In another embodiment, a composition or immunogenic combination of the application is a booster vaccine used for boosting an immune response. The priming and boosting vaccines of the application can be used in the methods of the application described herein. This general concept of a prime-boost regimen is well known to the skilled person in the vaccine field. Any of the compositions and immunogenic combinations of the application described herein can be used as priming and/or boosting vaccines for priming and/or boosting an immune response against HBV.

In some embodiments of the application, a composition or immunogenic combination of the application can be administered for priming immunization. The composition or immunogenic combination can be re-administered for boosting immunization. Further booster administrations of the composition or vaccine combination can optionally be added to the regimen, as needed. An adjuvant can be present in a composition of the application used for boosting immunization, present in a separate composition to be administered together with the composition or immunogenic combination of the application for the boosting immunization, or administered on its own as the boosting immunization. In those embodiments in which an adjuvant is included in the regimen, the adjuvant is preferably used for boosting immunization.

An illustrative and non-limiting example of a prime-boost regimen includes administering a single dose of an immunogenically effective amount of a composition or immunogenic combination of the application to a subject to prime the immune response; and subsequently administering another dose of an immunogenically effective amount of a composition or immunogenic combination of the application to boost the immune response, wherein the boosting immunization is first administered about two to six weeks, preferably four weeks after the priming immunization is initially administered. Optionally, about 10 to 14 weeks, preferably 12 weeks, after the priming immunization is initially administered, a further boosting immunization of the composition or immunogenic combination, or other adjuvant, is administered.

Kits

Also provided herein is a kit comprising an immunogenic combination of the application. A kit can comprise the first polynucleotide and the second polynucleotide in separate compositions, or a kit can comprise the first polynucleotide and the second polynucleotide in a single composition. A kit can further comprise one or more adjuvants or immune stimulants, and/or other anti-HBV agents.

The ability to induce or stimulate an anti-HBV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed. J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISPOT), by determination of the activation status of immune effector cells (e.g. T cell proliferation assays by a classical [$^3$H] thymidine uptake or flow cytometry-based assays), by assaying for antigen-specific T lymphocytes in a sensitized subject (e.g. peptide-specific lysis in a cytotoxicity assay, etc.).

The ability to stimulate a cellular and/or a humoral response can be determined by antibody binding and/or competition in binding (see for example Harlow, 1989, Antibodies, Cold Spring Harbor Press). For example, titers of antibodies produced in response to administration of a composition providing an immunogen can be measured by enzyme-linked immunosorbent assay (ELISA). The immune responses can also be measured by neutralizing antibody assay, where a neutralization of a virus is defined as the loss of infectivity through reaction/inhibition/neutralization of the virus with specific antibody. The immune response can further be measured by Antibody-Dependent Cellular Phagocytosis (ADCP) Assay.

EMBODIMENTS

Embodiments Section 1

Embodiment 1 comprises an isolated or non-naturally occurring nucleic acid molecule comprising a polynucleotide sequence encoding a truncated HBV core antigen consisting of an amino acid sequence that is at least 90% identical to SEQ ID NO: 2 or SEQ ID NO: 14, preferably 100% identical to SEQ ID NO: 2 or SEQ ID NO: 14; preferably the truncated HBV core antigen is capable of inducing an immune response in a mammal against at least two HBV genotypes; more preferably the truncated HBV core antigen is capable of inducing a T cell response in a mammal against at least HBV genotypes B, C and D; furthermore preferably the truncated HBV core antigen is capable of inducing a CD8 T cell response in a human subject against at least HBV genotypes A, B, C and D; and most preferably, the truncated HBV core antigen coding sequence comprises a polynucleotide that is at least 90%, such as 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15.

Embodiment 2 comprises the non-naturally occurring nucleic acid molecule of embodiment 1, wherein the truncated HBV core antigen consists of the amino acid sequence of SEQ ID NO: 2 or SEQ ID NO: 14.

Embodiment 3 comprises the non-naturally occurring nucleic acid molecule of embodiment 1 or embodiment 2, further comprising a polynucleotide sequence encoding a signal sequence operably linked to the HBV polymerase antigen.

Embodiment 4 comprises the non-naturally occurring nucleic acid molecule of embodiment 3, wherein the signal sequence comprises the amino acid sequence of SEQ ID NO: 6 or SEQ ID NO: 19, preferably the signal sequence is encoded by the polynucleotide sequence of SEQ ID NO: 5 or SEQ ID NO: 18.

Embodiment 5 comprises the non-naturally occurring nucleic acid molecule of any one of embodiments 1 to 4, wherein the polynucleotide sequence encoding the truncated core HBV antigen is at least 90% identical to SEQ ID NO: 1 or SEQ ID NO: 15.

Embodiment 6 comprises the non-naturally occurring nucleic acid molecule of embodiment 5, wherein the polynucleotide sequence encoding the truncated core HBV antigen comprises the polynucleotide sequence of SEQ ID NO: 1 or SEQ ID NO: 15.

Embodiment 7 comprises a non-naturally occurring nucleic acid molecule comprising a first polynucleotide sequence encoding an HBV polymerase antigen comprising an amino acid sequence that is at least 98% identical to SEQ ID NO: 4, wherein the HBV polymerase antigen does not have reverse transcriptase activity and RNase H activity.

Embodiment 8 comprises the non-naturally occurring nucleic acid molecule of embodiment 7, wherein the HBV polymerase antigen is capable of inducing an immune response in a mammal against at least two HBV genotypes, preferably the HBV polymerase antigen is capable of inducing a T cell response in a mammal against at least HBV genotypes B, C and D, and more preferably the HBV polymerase antigen is capable of inducing a CD8 T cell response in a human subject against at least HBV genotypes A, B, C and D.

Embodiment 9 comprises the non-naturally occurring nucleic acid molecule of embodiment 7, wherein the HBV polymerase antigen comprises the amino acid sequence of SEQ ID NO: 4.

Embodiment 10 comprises the non-naturally occurring nucleic acid molecule of any one of embodiments 7-9, further comprising a polynucleotide sequence encoding a signal sequence operably linked to the HBV polymerase antigen.

Embodiment 11 comprises the non-naturally occurring nucleic acid molecule of embodiment 10, wherein the signal sequence comprises the amino acid sequence of SEQ ID NO: 6 or SEQ ID NO: 19, preferably the signal sequence is encoded by the polynucleotide sequence of SEQ ID NO: 5 or SEQ ID NO: 18.

Embodiment 12 comprises the non-naturally occurring nucleic acid molecule of any one of embodiments 7 to 11, wherein the first polynucleotide sequence is at least 90% identical to SEQ ID NO: 3 or SEQ ID NO: 16.

Embodiment 13 comprises the non-naturally occurring nucleic acid molecule of embodiment 12, wherein the first polynucleotide sequence comprises the polynucleotide sequence of SEQ ID NO: 3 or SEQ ID NO: 16.

Embodiment 14 comprises the non-naturally occurring nucleic acid molecule of any one of embodiments 7 to 13, further comprising a second polynucleotide sequence encoding a truncated HBV core antigen consisting of the amino acid sequence of SEQ ID NO: 2 or SEQ ID NO: 14.

Embodiment 15 comprises the non-naturally occurring nucleic acid molecule of embodiment 14, wherein the second polynucleotide sequence is at least 90% identical to SEQ ID NO: 1 or SEQ ID NO: 15.

Embodiment 16 comprises the non-naturally occurring nucleic acid molecule of embodiment 15, wherein the second polynucleotide sequence comprises the polynucleotide sequence of SEQ ID NO: 1 or SEQ ID NO: 15.

Embodiment 17 comprises the non-naturally occurring nucleic acid molecule of any one of embodiments 14 to 16, encoding a fusion protein comprising the truncated HBV core antigen operably linked to the HBV polymerase antigen.

Embodiment 18 comprises the non-naturally occurring nucleic acid molecule of embodiment 17, wherein the fusion protein comprises the truncated HBV core antigen operably linked to the HBV polymerase antigen via a linker.

Embodiment 19 comprises the non-naturally occurring nucleic acid molecule of embodiment 18, wherein the linker comprises the amino acid sequence of $(AlaGly)_n$, and n is an integer of 2 to 5, preferably the linker is encoded by a polynucleotide sequence comprising SEQ ID NO: 22.

Embodiment 20 comprises the non-naturally occurring nucleic acid molecule of embodiment 19, wherein the fusion protein comprises the amino acid sequence of SEQ ID NO: 20.

Embodiment 21 comprises the non-naturally occurring nucleic acid molecule of any one of embodiments 17 to 20, wherein the fusion protein further comprises a signal sequence, preferably the signal sequence comprises the amino acid sequence of SEQ ID NO: 6 or SEQ ID NO: 19, more preferably the signal sequence is encoded by the polynucleotide sequence of SEQ ID NO: 5 or SEQ ID NO: 18.

Embodiment 22 comprises the non-naturally occurring nucleic acid molecule of any one of embodiments 7 to 21 further comprising a promoter sequence, optionally one or more additional regulatory sequences, preferably the promoter sequence comprises the polynucleotide sequence of SEQ ID NO: 7 or SEQ ID NO: 17, and the additional regulatory sequence is selected from the group consisting of an enhancer sequences of SEQ ID NO: 8 or SEQ ID NO: 23, and a polyadenylation signal sequence of SEQ ID NO: 11 or SEQ ID NO: 24.

Embodiment 23 comprises the non-naturally occurring nucleic acid molecule of any one of embodiments 7 to 22, wherein the non-naturally occurring nucleic acid molecule does not encode a HBV antigen selected from the group consisting of a Hepatitis B surface antigen (HBsAg), a HBV envelope (Env) antigen, and a HBV L protein antigen.

Embodiment 24 comprises a vector comprising the non-naturally occurring nucleic acid molecule of any one of embodiments 1 to 24.

Embodiment 25 comprises a vector of embodiment 24, wherein the non-naturally occurring nucleic acid molecule comprises, from 5' end to 3' end, a promoter sequence, an enhancer sequence, a signal peptide coding sequence, the first polynucleotide sequence, and a polyadenylation signal sequence, optionally, the non-naturally occurring nucleic acid molecule further comprises the second polynucleotide sequence.

Embodiment 26 comprises the vector of embodiment 24 or 25, wherein the vector is a plasmid DNA vector, and the plasmid DNA vector further comprises an origin of replication and an antibiotic resistance gene.

Embodiment 27 comprises the vector of embodiment 26, wherein the plasmid DNA vector contains the origin of replication comprising the polynucleotide sequence of SEQ ID NO: 10, the antibiotic resistance gene comprising the polynucleotide sequence of SEQ ID NO: 12, the promoter sequence comprising the polynucleotide sequence of SEQ ID NO: 7, the enhancer sequence comprising the polynucleotide sequence of SEQ ID NO: 8, the signal peptide coding sequence comprising the polynucleotide sequence of SEQ ID NO: 5, the first polynucleotide sequence comprising the polynucleotide sequence of SEQ ID NO: 3, and the polyadenylation signal sequence comprising the polynucleotide sequence of SEQ ID NO: 11, and optionally the second polynucleotide sequence comprising the polynucleotide sequence of SEQ ID NO: 1.

Embodiment 28 comprises the vector of embodiment 24 or 25, wherein the vector is an adenoviral vector, preferably an Ad26 or Ad35 vector.

Embodiment 29 comprises the vector of embodiment 28, wherein the vector is an Ad26 vector comprising the non-naturally occurring nucleic acid encoding the truncated core HBV antigen of any one of embodiments 1 to 6.

Embodiment 30 comprises the vector of embodiment 28, wherein the vector is an Ad26 vector comprising the non-naturally occurring nucleic acid encoding the HBV polymerase antigen of any one of embodiments 7 to 13.

Embodiment 31 comprises the vector of embodiment 28, wherein the vector is an Ad26 vector comprising the non-naturally occurring nucleic acid encoding the fusion protein of any one of embodiments 17-21.

Embodiment 31a comprises the vector of any one of embodiments 28 to 31, wherein the adenoviral vector contains the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 18, the second polynucleotide sequence comprising the polynucleotide sequence of SEQ ID NO: 15, the linker coding sequence comprising the polynucleotide sequence of SEQ ID NO: 22, the first polynucleotide sequence comprising the polynucleotide sequence of SEQ ID NO: 16, and the polyadenylation signal sequence comprising the polynucleotide sequence of SEQ ID NO: 24.

Embodiment 32 comprises the non-naturally occurring polypeptide encoded by the non-naturally occurring nucleic acid molecule of any embodiments 1 to 32.

Embodiment 33 comprises a host cell comprising the non-naturally occurring nucleic acid molecule of any one of embodiments 1 to 23 or the vector of any one of embodiments 24 to 32.

Embodiment 34 comprises a composition comprising the non-naturally occurring nucleic acid molecule of any one of embodiments 1 to 23, the vector of any one of embodiments 24 to 32, or the non-naturally occurring polypeptide of embodiment 33, and a pharmaceutically acceptable carrier.

Embodiment 35 comprises the composition of embodiment 34, comprising the first polynucleotide of any one of embodiments 7 to 13, the second polynucleotide of any one of embodiments 14-16, and a pharmaceutically acceptable carrier, wherein the first and second polynucleotides are not comprised in the same nucleic acid molecule or in the same nucleic acid vector.

Embodiment 36 comprises the composition of embodiment 35, wherein the first and second polynucleotides are comprised in two separate vectors, preferably adenovirus vectors, more preferably Ad26 vectors.

Embodiment 37 comprises a kit comprising:
(a) a first non-naturally occurring nucleic acid molecule comprising a first polynucleotide encoding a HBV polymerase antigen having an amino acid sequence that is at least 98% identical to SEQ ID NO: 4, wherein the HBV polymerase antigen does not have reverse transcriptase activity and RNase H activity;
(b) a second non-naturally occurring nucleic acid molecule comprising a second polynucleotide encoding a truncated HBV core antigen consisting of the amino acid sequence of SEQ ID NO: 2 or SEQ ID NO: 14; and
(c) a pharmaceutically acceptable carrier,
wherein the first non-naturally occurring nucleic acid molecule and the second non-naturally occurring nucleic acid molecule are present in the same non-naturally occurring nucleic acid molecule or in two different non-naturally occurring nucleic acid molecules.

Embodiment 38 comprises the kit of embodiment 37, wherein the HBV polymerase antigen is capable of inducing an immune response in a mammal against at least two HBV genotypes, preferably the HBV polymerase antigen is capable of inducing a T cell response in a mammal against at least HBV genotypes B, C and D, and more preferably the HBV polymerase antigen is capable of inducing a CD8 T cell response in a human subject against at least HBV genotypes A, B, C and D.

Embodiment 39 comprises the kit of embodiment 37, wherein the HBV polymerase antigen comprises the amino acid sequence of SEQ ID NO: 4.

Embodiment 40 comprises the kit of any one of embodiments 37 to 39, wherein at least one of the first non-naturally occurring nucleic acid molecule and the second non-naturally nucleic acid molecule further comprises a polynucleotide sequence encoding a signal sequence operably linked to at least one of the HBV polymerase antigen and the truncated HBV core antigen.

Embodiment 41 comprises the kit of embodiment 40, wherein the signal sequence independently comprises the amino acid sequence of SEQ ID NO: 6 or SEQ ID NO: 19, preferably the signal sequence is independently encoded by the polynucleotide sequence of SEQ ID NO: 5 or SEQ ID NO: 18.

Embodiment 42 comprises the kit of any one of embodiments 37 to 41, wherein the first polynucleotide sequence is at least 90% identical to SEQ ID NO: 3 or SEQ ID NO: 16.

Embodiment 43 comprises the kit of embodiment 42, wherein the first polynucleotide sequence comprises the polynucleotide sequence of SEQ ID NO: 3 or SEQ ID NO: 16.

Embodiment 44 comprises the kit of any one of embodiments 37 to 43, wherein the second polynucleotide sequence is at least 90% identical to SEQ ID NO: 1 or SEQ ID NO: 15.

Embodiment 45 comprises the kit of embodiment 44, wherein the second polynucleotide sequence comprises the polynucleotide sequence of SEQ ID NO: 1 or SEQ ID NO: 15.

Embodiment 46 comprises the kit of any one of embodiments 37 to 45, wherein at least one of the first non-naturally occurring nucleic acid molecule and the second non-naturally nucleic acid molecule further comprises a promoter sequence, optionally an enhancer sequence, and further optionally a polyadenylation signal sequence, preferably the promoter sequence has the polynucleotide sequence of SEQ ID NO: 7 or SEQ ID NO: 17, the enhancer sequence independently has the polynucleotide sequence of SEQ ID NO: 8 or SEQ ID NO: 23, and the polyadenylation signal sequence independently has the polynucleotide sequence of SEQ ID NO: 11 or SEQ ID NO: 24.

Embodiment 47 comprises the kit of any one of embodiments 37 to 46, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 48 comprises the kit of any one of embodiments 37 to 47, wherein the first non-naturally occurring nucleic acid molecule and the second non-naturally occurring nucleic acid molecule are present in the same vector.

Embodiment 49 comprises the kit of embodiment 48, wherein the vector encodes the HBV polymerase antigen and the truncated HBV core antigen as two separate proteins.

Embodiment 50 comprises the kit of embodiment 49, wherein the vector encodes a fusion protein comprising the truncated HBV core antigen operably linked to the HBV polymerase antigen.

Embodiment 51 comprises the kit of embodiment 50, wherein the fusion protein comprises the truncated HBV core antigen operably linked to the HBV polymerase antigen via a linker.

Embodiment 52 comprises the kit of embodiment 51, wherein the linker comprises the amino acid sequence of (AlaGly)n, and n is an integer of 2 to 5, preferably the linker is encoded by a polynucleotide sequence comprising SEQ ID NO: 22.

Embodiment 53 comprises the kit of embodiment 52, wherein the fusion protein comprises the amino acid sequence of SEQ ID NO: 20.

Embodiment 54 comprises the kit of embodiment 53, wherein the fusion protein further comprises a signal sequence, preferably the signal sequence has the amino acid sequence of SEQ ID NO: 6 or SEQ ID NO: 19, more preferably the signal sequence is encoded by the polynucleotide sequence of SEQ ID NO: 5 or SEQ ID NO: 18.

Embodiment 55 comprises the kit of embodiment 54, wherein the fusion protein comprises the amino acid sequence of SEQ ID NO: 21.

Embodiment 56 comprises the kit of any one of embodiments 48 to 55, wherein the vector contains, from 5' end to 3' end, a promoter sequence, an enhancer sequence, a signal peptide coding sequence, the second polynucleotide sequence, a linker coding sequence, the first polynucleotide sequence, and a polyadenylation signal sequence.

Embodiment 57 comprises the kit of embodiment 56, wherein the vector is an adenoviral vector, preferably an Ad26 or Ad35 vector.

Embodiment 58 comprises the kit of embodiment 57, wherein the adenoviral vector contains the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 18, the second polynucleotide sequence comprising the polynucleotide sequence of SEQ ID NO: 15, the linker coding sequence comprising the polynucleotide sequence of SEQ ID NO: 22, the first polynucleotide sequence comprising the polynucleotide sequence of SEQ ID NO: 16, and the polyadenylation signal sequence comprising the polynucleotide sequence of SEQ ID NO: 24.

Embodiment 59 comprises the kit of embodiment 58, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 60 comprises the kit of any one of embodiments 37 to 59, wherein the first non-naturally occurring nucleic acid molecule and the second non-naturally occurring nucleic acid molecule are present in two different vectors.

Embodiment 61 comprises the kit of embodiment 60, wherein the first non-naturally occurring nucleic acid molecule is present in a first plasmid DNA vector, and the second non-naturally occurring nucleic acid molecule is present in a second plasmid DNA vector.

Embodiment 62 comprises the kit of embodiment 61, wherein each of the first and second plasmid DNA vectors comprises an origin of replication, an antibiotic resistance gene, and from 5' end to 3' end, a promoter sequence, a regulatory sequence, a signal peptide coding sequence, the first polynucleotide sequence or the second polynucleotide sequence, and a polyadenylation signal sequence.

Embodiment 63 comprises the kit of embodiment 62, wherein the antibiotic resistance gene is a kanamycin resistance gene having a polynucleotide sequence at least 90% identical to SEQ ID NO: 12, preferably 100% identical to SEQ ID NO: 12.

Embodiment 64 comprises the kit of embodiment 63, comprising,
  (a) a first plasmid DNA vector comprising, from 3'-end to 5'-end, the promoter sequence comprising the polynucleotide sequence of SEQ ID NO: 7, the regulatory sequence comprising the polynucleotide sequence of SEQ ID NO: 8, the signal peptide coding sequence comprising the polynucleotide sequence of SEQ ID NO: 5, the first polynucleotide sequence comprising the polynucleotide sequence of SEQ ID NO: 3, and the polyadenylation signal sequence comprising the polynucleotide sequence of SEQ ID NO: 11;
  (b) a second plasmid DNA vector comprising, from 3'-end to 5'-end, the promoter sequence comprising the polynucleotide sequence of SEQ ID NO: 7, the regulatory sequence comprising the polynucleotide sequence of SEQ ID NO: 8, the signal peptide coding sequence comprising the polynucleotide sequence of SEQ ID NO: 5, the second polynucleotide sequence comprising the polynucleotide sequence of SEQ ID NO: 1, and the polyadenylation signal sequence comprising the polynucleotide sequence of SEQ ID NO: 11; and
  (c) a pharmaceutically acceptable carrier,
wherein each of the first plasmid DNA vector and the second plasmid DNA vector further comprises a kanamycin resistance gene having the polynucleotide sequence of SEQ ID NO: 12, and an origin of replication having the polynucleotide sequence of SEQ ID NO: 10, and wherein the first plasmid DNA vector and the second plasmid DNA vector are in the same composition or two different compositions.

Embodiment 65 comprises the kit of embodiment 60, wherein the first non-naturally occurring nucleic acid molecule is present in a first adenovirus vector, preferably Ad26 vector, and the second non-naturally occurring nucleic acid molecule is present in a second adenovirus vector, preferably Ad26 vector.

Embodiment 66 comprises the kit of embodiment 65, wherein each of the first and second adenovirus vectors comprises from 5' end to 3' end, a promoter sequence, a regulatory sequence, a signal peptide coding sequence, the first polynucleotide sequence or the second polynucleotide sequence, and a polyadenylation signal sequence.

Embodiment 67 comprises the kit of embodiment 66, comprising,
  (a) a first Ad26 vector comprising, from 3'-end to 5'-end, the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 17, the first polynucleotide sequence comprising the polynucleotide sequence of SEQ ID NO: 15, and the polyadenylation signal sequence comprising the polynucleotide sequence of SEQ ID NO: 24;
  (b) a second Ad26 vector comprising, from 3'-end to 5'-end, the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 17, the second polynucleotide sequence comprising the polynucleotide sequence of SEQ ID NO: 16, and the polyadenylation signal sequence comprising the polynucleotide sequence of SEQ ID NO: 24; and
  (c) a pharmaceutically acceptable carrier,
wherein each of the first Ad26 vector and the second Ad26 vector are in the same composition or two different compositions.

Embodiment 68 comprises the kit of any one of embodiments 64 to 67, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 69 comprises the composition of any one of embodiments 34 to 36 or the kit of any one of embodiments 37 to 68 for use in inducing an immune response against a hepatitis B virus (HBV) in a subject in need thereof, preferably the subject has chronic HBV infection.

Embodiment 70 comprises a combination of another immunogenic agent, preferably another HBV antigen, with the composition of any one of embodiments 34 to 36 or the kit of any one of embodiments 37 to 68 for use in inducing an immune response against a hepatitis B virus (HBV) in a subject in need thereof, preferably the subject has chronic HBV infection.

Embodiment 71 comprises the composition of any one of embodiments 34 to 36 or the kit of any one of embodiments 37 to 68 for use in treating a hepatitis B virus (HBV)-induced disease in a subject in need thereof, preferably the subject has chronic HBV infection, and the HBV-induced disease is selected from the group consisting of advanced fibrosis, cirrhosis and hepatocellular carcinoma (HCC).

Embodiment 72 comprises a combination of another therapeutic agent, preferably another anti-HBV agent, with the composition of any one of embodiments 34 to 36 or the kit of any one of embodiments 37 to 68 for use in treating a hepatitis B virus (HBV)-induced disease in a subject in need thereof, preferably the subject has chronic HBV infection, and the HBV-induced disease is selected from the group consisting of advanced fibrosis, cirrhosis and hepatocellular carcinoma (HCC).

Embodiments Section 2

Embodiment 1 comprises a non-naturally occurring nucleic acid molecule comprising a first polynucleotide sequence encoding an HBV polymerase antigen comprising an amino acid sequence that is at least 98% identical to SEQ ID NO: 4, wherein the HBV polymerase antigen does not have reverse transcriptase activity and RNase H activity.

Embodiment 2 comprises the non-naturally occurring nucleic acid molecule of embodiment 1, wherein the HBV polymerase antigen is capable of inducing an immune response in a mammal against at least two HBV genotypes, preferably the HBV polymerase antigen is capable of inducing a T cell response in a mammal against at least HBV genotypes B, C and D, and more preferably the HBV polymerase antigen is capable of inducing a CD8 T cell response in a human subject against at least HBV genotypes A, B, C and D.

Embodiment 3 comprises the non-naturally occurring nucleic acid molecule of embodiment 1, wherein the HBV polymerase antigen comprises the amino acid sequence of SEQ ID NO: 4.

Embodiment 4 comprises the non-naturally occurring nucleic acid molecule of any one of embodiments 1-3, further comprising a polynucleotide sequence encoding a signal sequence operably linked to the HBV polymerase antigen.

Embodiment 5 comprises the non-naturally occurring nucleic acid molecule of embodiment 4, wherein the signal sequence comprises the amino acid sequence of SEQ ID NO: 6 or SEQ ID NO: 19, preferably the signal sequence is encoded by the polynucleotide sequence of SEQ ID NO: 5 or SEQ ID NO: 18.

Embodiment 6 comprises the non-naturally occurring nucleic acid molecule of any one of embodiments 1 to 5, wherein the first polynucleotide sequence is at least 90% identical to SEQ ID NO: 3 or SEQ ID NO: 16.

Embodiment 7 comprises the non-naturally occurring nucleic acid molecule of embodiment 6, wherein the first polynucleotide sequence comprises the polynucleotide sequence of SEQ ID NO: 3 or SEQ ID NO: 16.

Embodiment 8 comprises the non-naturally occurring nucleic acid molecule of any one of embodiments 1 to 7, further comprising a second polynucleotide sequence encoding a truncated HBV core antigen consisting of the amino acid sequence of SEQ ID NO: 2 or SEQ ID NO: 14.

Embodiment 9 comprises the non-naturally occurring nucleic acid molecule of embodiment 8, wherein the second polynucleotide sequence is at least 90% identical to SEQ ID NO: 1 or SEQ ID NO: 15.

Embodiment 10 comprises the non-naturally occurring nucleic acid molecule of embodiment 9, wherein the second polynucleotide sequence comprises the polynucleotide sequence of SEQ ID NO: 1 or SEQ ID NO: 15.

Embodiment 11 comprises the non-naturally occurring nucleic acid molecule of any one of embodiments 8 to 10, encoding a fusion protein comprising the truncated HBV core antigen operably linked to the HBV polymerase antigen.

Embodiment 12 comprises the non-naturally occurring nucleic acid molecule of embodiment 11, wherein the fusion protein comprises the truncated HBV core antigen operably linked to the HBV polymerase antigen via a linker.

Embodiment 13 comprises the non-naturally occurring nucleic acid molecule of embodiment 12, wherein the linker comprises the amino acid sequence of (AlaGly)$_n$, and n is an integer of 2 to 5, preferably the linker is encoded by a polynucleotide sequence comprising SEQ ID NO: 22.

Embodiment 14 comprises the non-naturally occurring nucleic acid molecule of embodiment 13, wherein the fusion protein comprises the amino acid sequence of SEQ ID NO: 20.

Embodiment 15 comprises the non-naturally occurring nucleic acid molecule of any one of embodiments 11 to 14, wherein the fusion protein further comprises a signal sequence, preferably the signal sequence comprises the amino acid sequence of SEQ ID NO: 6 or SEQ ID NO: 19, more preferably the signal sequence is encoded by the polynucleotide sequence of SEQ ID NO: 5 or SEQ ID NO: 18.

Embodiment 16 comprises the non-naturally occurring nucleic acid molecule of any one of embodiments 1 to 15 further comprising a promoter sequence, optionally one or more additional regulatory sequences, preferably the promoter sequence comprises the polynucleotide sequence of SEQ ID NO: 7 or SEQ ID NO: 17, and the additional regulatory sequence is selected from the group consisting of SEQ ID NO: 8 or SEQ ID NO: 23, and a polyadenylation signal sequence of SEQ ID NO: 11 or SEQ ID NO: 24.

Embodiment 17 comprises the non-naturally occurring nucleic acid molecule of any one of embodiments 1 to 16, wherein the non-naturally occurring nucleic acid molecule does not encode a HBV antigen selected from the group consisting of a Hepatitis B surface antigen (HBsAg), a HBV envelope (Env) antigen, and a HBV L protein antigen.

Embodiment 18 comprises a vector comprising the non-naturally occurring nucleic acid molecule of any one of embodiments 1 to 17.

Embodiment 19 comprises the vector of embodiment 18, wherein the non-naturally occurring nucleic acid molecule comprises, from 5' end to 3' end, a promoter sequence, an enhancer sequence, a signal peptide coding sequence, the first polynucleotide sequence, and a polyadenylation signal sequence, optionally, the non-naturally occurring nucleic acid molecule further comprises the second polynucleotide sequence.

Embodiment 20 comprises the vector of embodiment 18 or 19, wherein the vector is a plasmid DNA vector, and the plasmid DNA vector further comprises an origin of replication and an antibiotic resistance gene.

Embodiment 21 comprises the vector of embodiment 20, wherein the plasmid DNA vector contains the origin of replication comprising the polynucleotide sequence of SEQ ID NO: 10, the antibiotic resistance gene comprising the polynucleotide sequence of SEQ ID NO: 12, the promoter sequence comprising the polynucleotide sequence of SEQ ID NO: 7, the enhancer sequence comprising the polynucleotide sequence of SEQ ID NO: 8, the signal peptide coding sequence comprising the polynucleotide sequence of SEQ ID NO: 5, the first polynucleotide sequence comprising the polynucleotide sequence of SEQ ID NO: 3, and the polyadenylation signal sequence comprising the polynucleotide sequence of SEQ ID NO: 11, and optionally the second polynucleotide sequence comprising the polynucleotide sequence of SEQ ID NO: 1.

Embodiment 22 comprises the vector of embodiment 18 or 19, wherein the vector is an adenoviral vector, preferably an Ad26 or Ad35 vector.

Embodiment 23 comprises the vector of embodiment 22, wherein the adenoviral vector contains the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 18, the second polynucleotide sequence comprising the polynucleotide sequence of SEQ ID NO: 15, the linker coding sequence comprising the polynucleotide sequence of SEQ ID NO: 22, the first polynucleotide sequence comprising the polynucleotide sequence of SEQ ID NO: 16, and the polyadenylation signal sequence comprising the polynucleotide sequence of SEQ ID NO: 24.

Embodiment 24 comprises a non-naturally occurring polypeptide encoded by the non-naturally occurring nucleic acid molecule of any one of embodiments 1 to 17.

Embodiment 25 comprises a host cell comprising the non-naturally occurring nucleic acid molecule of any one of embodiments 1 to 17 or the vector of any one of embodiments 18 to 23.

Embodiment 26 comprises a composition comprising the non-naturally occurring nucleic acid molecule of any one of embodiments 1 to 17, the vector of any one of embodiments 18 to 23, or the non-naturally occurring polypeptide of embodiment 24, and a pharmaceutically acceptable carrier.

Embodiment 27 comprises the composition of embodiment 26, comprising the first polynucleotide of any one of embodiments 1-7, the second polynucleotide of any one of embodiments 8-10, and a pharmaceutically acceptable carrier, wherein the first and second polynucleotides are not comprised in the same nucleic acid molecule or in the same nucleic acid vector.

Embodiment 28 comprises a kit comprising:
(a) a first non-naturally occurring nucleic acid molecule comprising a first polynucleotide encoding a HBV polymerase antigen having an amino acid sequence that is at least 98% identical to SEQ ID NO: 4, wherein the HBV polymerase antigen does not have reverse transcriptase activity and RNase H activity;
(b) a second non-naturally occurring nucleic acid molecule comprising a second polynucleotide encoding a truncated HBV core antigen consisting of the amino acid sequence of SEQ ID NO: 2 or SEQ ID NO: 14; and
(c) a pharmaceutically acceptable carrier,
wherein the first non-naturally occurring nucleic acid molecule and the second non-naturally occurring nucleic acid molecule are present in the same non-naturally occurring nucleic acid molecule or in two different non-naturally occurring nucleic acid molecules.

Embodiment 29 comprises the kit of embodiment 28, wherein the HBV polymerase antigen is capable of inducing an immune response in a mammal against at least two HBV genotypes, preferably the HBV polymerase antigen is capable of inducing a T cell response in a mammal against at least HBV genotypes B, C and D, and more preferably the HBV polymerase antigen is capable of inducing a CD8 T cell response in a human subject against at least HBV genotypes A, B, C and D.

Embodiment 30 comprises the kit of embodiment 29, wherein the HBV polymerase antigen comprises the amino acid sequence of SEQ ID NO: 4.

Embodiment 31 comprises the kit of any one of embodiments 28 to 30, wherein at least one of the first non-naturally occurring nucleic acid molecule and the second non-naturally nucleic acid molecule further comprises a polynucleotide sequence encoding a signal sequence operably linked to the at least one of the HBV polymerase antigen and the truncated HBV core antigen.

Embodiment 32 comprises the kit of embodiment 31, wherein the signal sequence independently comprises the amino acid sequence of SEQ ID NO: 6 or SEQ ID NO: 19, preferably the signal sequence is independently encoded by the polynucleotide sequence of SEQ ID NO: 5 or SEQ ID NO: 18.

Embodiment 33 comprises the kit of any one of embodiments 28 to 32, wherein the first polynucleotide sequence is at least 90% identical to SEQ ID NO: 3 or SEQ ID NO: 16.

Embodiment 34 comprises the kit of embodiment 33, wherein the first polynucleotide sequence comprises the polynucleotide sequence of SEQ ID NO: 3 or SEQ ID NO: 16.

Embodiment 35 comprises the kit of any one of embodiments 28 to 34, wherein the second polynucleotide sequence is at least 90% identical to SEQ ID NO: 1 or SEQ ID NO: 15.

Embodiment 36 comprises the kit of embodiment 35, wherein the second polynucleotide sequence comprises the polynucleotide sequence of SEQ ID NO: 1 or SEQ ID NO: 15.

Embodiment 37 comprises the kit of any one of embodiments 28 to 36, wherein at least one of the first non-naturally occurring nucleic acid molecule and the second non-naturally nucleic acid molecule further comprises a promoter sequence, optionally an enhancer sequence, and further optionally a polyadenylation signal sequence, preferably the promoter sequence has the polynucleotide sequence of SEQ ID NO: 7 or SEQ ID NO: 17, the enhancer sequence independently has the polynucleotide sequence of SEQ ID NO: 8 or SEQ ID NO: 23, and the polyadenylation signal sequence independently has the polynucleotide sequence of SEQ ID NO: 11 or SEQ ID NO: 24.

Embodiment 38 comprises the kit of any one of embodiments 28 to 37, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 39 comprises the kit of any one of embodiment 28 to 38, wherein the first non-naturally occurring nucleic acid molecule and the second non-naturally occurring nucleic acid molecule are present in the same vector.

Embodiment 40 comprises the kit of embodiment 39, wherein the vector encodes the HBV polymerase antigen and the truncated HBV core antigen as two separate proteins.

Embodiment 41 comprises the kit of embodiment 39, wherein the vector encodes a fusion protein comprising the truncated HBV core antigen operably linked to the HBV polymerase antigen.

Embodiment 42 comprises the kit of embodiment 41, wherein the fusion protein comprises the truncated HBV core antigen operably linked to the HBV polymerase antigen via a linker.

Embodiment 43 comprises the kit of embodiment 42, wherein the linker comprises the amino acid sequence of $(AlaGly)_n$, and n is an integer of 2 to 5, preferably the linker is encoded by a polynucleotide sequence comprising SEQ ID NO: 22.

Embodiment 44 comprises the kit of embodiment 43, wherein the fusion protein comprises the amino acid sequence of SEQ ID NO: 20.

Embodiment 45 comprises the kit of embodiment 44, wherein the fusion protein further comprises a signal sequence, preferably the signal sequence has the amino acid sequence of SEQ ID NO: 6 or SEQ ID NO: 19, more preferably the signal sequence is encoded by the polynucleotide sequence of SEQ ID NO: 5 or SEQ ID NO: 18.

Embodiment 46 comprises the kit of embodiment 45, wherein the fusion protein comprises the amino acid sequence of SEQ ID NO: 21.

Embodiment 47 comprises the kit of any one of embodiments 41 to 46, wherein the vector contains, from 5' end to 3' end, a promoter sequence, an enhancer sequence, a signal peptide coding sequence, the second polynucleotide sequence, a linker coding sequence, the first polynucleotide sequence, and a polyadenylation signal sequence.

Embodiment 48 comprises the kit of embodiment 47, wherein the vector is an adenoviral vector, preferably an Ad26 or Ad35 vector.

Embodiment 49 comprises the kit of embodiment 48, wherein the adenoviral vector contains the promoter sequence comprising the polynucleotide sequence of SEQ ID NO: 17, the regulatory sequence comprising the polynucleotide sequence of SEQ ID NO: 23, the signal peptide coding sequence comprising the polynucleotide sequence of SEQ ID NO: 18, the second polynucleotide sequence comprising the polynucleotide sequence of SEQ ID NO: 15, the linker coding sequence comprising the polynucleotide sequence of SEQ ID NO: 22, the first polynucleotide sequence comprising the polynucleotide sequence of SEQ ID NO: 16, and the polyadenylation signal sequence comprising the polynucleotide sequence of SEQ ID NO: 24.

Embodiment 50 comprises the kit of embodiment 49, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 51 comprises the kit of any one of embodiments 28 to 38, wherein the first non-naturally occurring nucleic acid molecule and the second non-naturally occurring nucleic acid molecule are present in two different vectors.

Embodiment 52 comprises the kit of embodiment 51, wherein the first non-naturally occurring nucleic acid molecule is present in a first plasmid DNA vector, and the second non-naturally occurring nucleic acid molecule is present in a second plasmid DNA vector.

Embodiment 53 comprises the kit of embodiment 52, wherein each of the first and second plasmid DNA vectors comprises an origin of replication, an antibiotic resistance gene, and from 5' end to 3' end, a promoter sequence, a regulatory sequence, a signal peptide coding sequence, the first polynucleotide sequence or the second polynucleotide sequence, and a polyadenylation signal sequence.

Embodiment 54 comprises the kit of embodiment 53, wherein the antibiotic resistance gene is a kanamycin resistance gene having a polynucleotide sequence at least 90% identical to SEQ ID NO: 12, preferably 100% identical to SEQ ID NO: 12.

Embodiment 55 comprises the kit of embodiment 54, comprising,
(a) a first plasmid DNA vector comprising, from 3'-end to 5'-end, the promoter sequence comprising the polynucleotide sequence of SEQ ID NO: 7, the regulatory sequence comprising the polynucleotide sequence of SEQ ID NO: 8, the signal peptide coding sequence comprising the polynucleotide sequence of SEQ ID NO: 5, the first polynucleotide sequence comprising the polynucleotide sequence of SEQ ID NO: 3, and the polyadenylation signal sequence comprising the polynucleotide sequence of SEQ ID NO: 11;
(b) a second plasmid DNA vector comprising, from 3'-end to 5'-end, the promoter sequence comprising the polynucleotide sequence of SEQ ID NO: 7, the regulatory sequence comprising the polynucleotide sequence of SEQ ID NO: 8, the signal peptide coding sequence comprising the polynucleotide sequence of SEQ ID NO: 5, the second polynucleotide sequence comprising the polynucleotide sequence of SEQ ID NO: 1, and the polyadenylation signal sequence comprising the polynucleotide sequence of SEQ ID NO: 11; and
(c) a pharmaceutically acceptable carrier,
wherein each of the first plasmid DNA vector and the second plasmid DNA vector further comprises a kanamycin resistance gene having the polynucleotide sequence of SEQ ID NO: 12, and an original of replication having the polynucleotide sequence of SEQ ID NO: 10, and
wherein the first plasmid DNA vector and the second plasmid DNA vector are in the same composition or two different compositions.

Embodiment 56 comprises the kit of embodiment 55, wherein the kit does not contain a nucleic acid molecule encoding a HBV antigen selected from the group consisting of a Hepatitis B surface antigen (HBsAg), a HBV envelope (Env) antigen, and a HBV L protein antigen, nor a HBV antigen selected from the group consisting of a Hepatitis B surface antigen (HBsAg), a HBV envelope (Env) antigen, and a HBV L protein antigen.

Embodiment 57 comprises the composition of embodiment 26 or the kit of any one of embodiments 27 to 55 for use in inducing an immune response against a hepatitis B virus (HBV) in a subject in need thereof, preferably the subject has chronic HBV infection.

Embodiment 58 comprises a combination of another immunogenic agent, preferably another HBV antigen, with the composition of embodiment 26 or the kit of any one of embodiments 27 to 55 for use in inducing an immune response against a hepatitis B virus (HBV) in a subject in need thereof, preferably the subject has chronic HBV infection.

Embodiment 59 comprises the composition of embodiment 26 or 27 or the kit of any one of embodiments 28 to 56 for use in treating a hepatitis B virus (HBV)-induced disease in a subject in need thereof, preferably the subject has chronic HBV infection, and the HBV-induced disease is selected from the group consisting of advanced fibrosis, cirrhosis and hepatocellular carcinoma (HCC).

Embodiment 60 comprises a combination of another therapeutic agent, preferably another anti-HBV agent, with the composition of embodiment 26 or 27 or the kit of any one of embodiments 28 to 56 for use in treating a hepatitis B virus (HBV)-induced disease in a subject in need thereof, preferably the subject has chronic HBV infection, and the HBV-induced disease is selected from the group consisting of advanced fibrosis, cirrhosis and hepatocellular carcinoma (HCC).

EXAMPLES

The following examples of the application are to further illustrate the nature of the application. It should be understood that the following examples do not limit the application and the scope of the application is to be determined by the appended claims.

Example 1: Generation of HBV Core and Pol Antigen Sequences and Plasmid Optimization T-cell epitopes on the hepatitis core protein are considered important for elimination of hepatitis B infection and hepatitis B viral proteins, such as polymerase, may serve to improve the breadth of the response. Thus, hepatitis B core and polymerase proteins were selected as antigens for the design of a therapeutic hepatitis B virus (HBV) vaccine.

Derivation of HBV Core and Polymerase Antigen Consensus Sequences

HBV pol and core antigen consensus sequences were generated based on HBV genotypes B, C, and D. Different HBV sequences were obtained from different sources and aligned separately for core and polymerase proteins. Original sequence alignments for all subtypes (A to H) were subsequently limited to HBV genotypes, B, C, and D. Consensus sequences were defined for each protein alignment in each subtype separately and in all joint BCD sequences. In variable alignment positions, the most frequent amino acid was used in the consensus sequence.

Optimization of HBV Core Antigen

The HBV core antigen consensus sequence was optimized by a deletion in the native viral protein. In particular, a deletion of thirty-four amino acids corresponding to the C-terminal highly positively charged segment was made, which is required for pre-genomic RNA encapsidation.

Optimization of the HBV Pol Antigen

The HBV pol antigen consensus sequence was optimized by changing four residues to remove reverse transcriptase and RNAseH enzymatic activities. In particular, the asparate residues (D) were changed to asparagine residues (N) in the "YXDD" motif of the reverse transcriptase domain to eliminate any coordination function, and thus nucleotide/metal ion binding. Additionally, the first aspartate residue (D) was changed to an asparagine residue (N) and the first glutamate residue (E) was changed to a glutamine residue (A) in the "DEDD" motif of the RNAseH domain to eliminate Mg' coordination. Additionally, the sequence of the HBV pol antigen was codon optimized to scramble the internal open reading frames for the envelope proteins, including the S protein and versions of the S protein with the N-terminal extensions pre-S1 and pre-S2. As a result, open reading frames for the envelope proteins (pre-S1, pre-S2, and S protein) and the X protein were removed.

Optimization of HBV Core and Pol Antigen Expression Strategies

Three different strategies were tested to obtain maximum and equal expression of both core and pol antigens from plasmid vectors: (1) fusion of HBV core and pol antigens in frame with a small AGAG inserted between the coding sequences to produce a single Core-Pol fusion protein (FIG. 2A); (2) expression of both core and pol antigens from one plasmid by means of a ribosomal slippage site, particularly the FA2 slippage site from foot-and-mouth disease (FMDV) to produce a biscistronic expression vector expressing individual core and pol proteins from a single mRNA (FIG. 2B); and (3) two separate plasmids encoding for HBV core and pol antigens, respectively (FIG. 2C).

In vitro Expression Analysis

The coding sequences of consensus HBV core and pol antigens according to each of the above three expression strategies were cloned into the commercially available expression plasmid pcDNA3.1. HEK-293T cells were transfected with the vectors and protein expression was evaluated by Western blot using a HBV core-specific antigen.

Optimization of Post-Transcriptional Regulatory Elements

Four different post-transcriptional regulatory elements were evaluated for enhancement of protein expression by stabilizing the primary transcript, facilitating its nuclear export, and/or improving transcriptional-translational coupling: (1) Woodchuck HBV post-transcriptional regulatory element (WPRE) (GenBank: J04514.1); (2) intron/exon sequence derived from human apolipoprotein A1 precursor (GenBank: X01038.1); (3) untranslated R-U5 domain of the human T-cell leukemia virus type 1 (HTLV-1) long terminal repeat (LTR) (GenBank: KM023768.1); and (4) composite sequence of the HTLV-1 LTR, synthetic rabbit β-globin intron (GenBank: V00882.1), and a splicing enhancer (triple composite sequence). The enhancer sequences were introduced between a CMV promoter and the HBV antigen coding sequences in the plasmids. No significant difference was observed by Western blot in the expression of the core antigen when expressed from a plasmid in the presence and absence of the WPRE element (FIG. 2D). However, when core antigen expression in HEK293T transfected cells from plasmids having the other three post-transcriptional regulatory sequences was evaluated by Western blot, the triple enhancer sequence resulted in the strongest core antigen expression (FIG. 2E).

Selection of Signal Peptide for Efficient Protein Secretion

Three different signal peptides introduced in frame at the N-terminus of the HBV core antigen were evaluated: (1) Ig heavy chain gamma signal peptide SPIgG (BAA75024.1); (2) the Ig heavy chain epsilon signal peptide SPIgE (AAB59424.1); and (3) the Cystatin S precursor signal peptide SPCS (NP_0018901.1). Signal peptide cleavage sites were optimized in silico for core fusion using the Signal P prediction program. Secretion efficiency was determined by analyzing core protein levels in the supernatant. Western blot analysis of core antigen secretion using the three different signal peptides fused at the N-terminus demonstrated that the Cystatin S signal peptide resulted in the most efficient protein secretion (FIG. 2F).

DNA Vaccine Vector Optimization

The optimized expression cassettes containing the triple composite enhancer sequence upstream of the HBV antigen coding sequence with an N-terminal Cystatin S signal peptide sequence were cloned in the DNA vaccine vector pVax-1 (Life Technologies, Thermo Fisher Scientific, Waltham, Mass.). The expression cassette in pVax-1 contains a human CMV-IE promoter followed by the bovine growth hormone (BGH)-derived polyadenylation sequence (pA). Bacterial propagation is driven by the pUC ori replicon and kanamycin resistance gene (Kan R) driven by a small eukaryotic promoter. The pUC ori replication, KanR expression cassette, and expression cassette driven by the CMV-IE promoter are all in the same orientation within the plasmid backbone. However, a marked reduction in core antigen expression was observed in the pVax-1 vector as compared to the expression level observed in the pcDNA3.1 vector.

Several strategies were employed to improve protein expression: (1) reversal of the entire pUCori-KanR cassette into counterclockwise orientation (pVD-core); and (2) changing the codon usage of the KanR gene along with replacement of the Kan promoter with the Amp promoter from the pcDNA3.1 vector (pDK-core). Both strategies restore core antigen expression, but core antigen expression was highest with the pDK vector, which contained the codon-adjusted Kan R gene, AmpR promotor (instead of KanR promoter), and inverse orientation of the pUCori-KanR cassette.

The four different HBV core/pol antigen optimized expression cassettes as shown in FIG. 2G were introduced into the pDK plasmid backbone to test each of the three expression strategies illustrated in FIGS. 2A-2C. The plasmids were tested in vitro for core and pol antigen expression by Western blot analysis using core and pol specific antibodies. The most consistent expression profile for cellular and secreted core and pol antigens was achieved when the core and pol antigens were encoded by separate vectors, namely the individual DNA vectors pDK-core and pDK-pol (FIG. 21I). A schematic representation of the pDK-pol and pDK-core vectors is shown in FIGS. 3A and 3B, respectively.

Example 2: Generation of Adenoviral Vectors Expressing a Fusion of Truncated HBV Core Antigen with HBV Pol Antigen The creation of an adenovirus vector has been designed as a fusion protein expressed from a single open reading frame. Additional configurations for the expression of the two proteins, e.g. using two separate expression cassettes, or using a 2A-like sequence to separate the two sequences, can also be envisaged.

Design of Expression Cassettes for Adenoviral Vectors

The expression cassettes (diagrammed in FIG. 8 A and FIG. 8B) are comprised of the CMV promoter (SEQ ID NO: 17), an intron (SEQ ID NO: 23) (a fragment derived from the human ApoAI gene-GenBank accession X01038 base pairs 295-523, harboring the ApoAI second intron), followed by the optimized coding sequence—either core alone or the core and polymerase fusion protein preceded by a human immunoglobulin secretion signal coding sequence (SEQ ID NO: 18), and followed by the SV40 polyadenylation signal (SEQ ID NO: 24).

A secretion signal was included because of past experience showing improvement in the manufacturability of some adenoviral vectors harboring secreted transgenes, without influencing the elicited T-cell response (mouse experiments).

The last two residues of the Core protein (VV) and the first two residues of the Polymerase protein (MP) if fused results in a junction sequence (VVMP) that is present on the human dopamine receptor protein (D3 isoform), along with flanking homologies.

The interjection of an AGAG linker between the core and the polymerase sequences eliminates this homology and returned no further hits in a Blast of the human proteome.

Example 3: In Vivo Immunogenicity Study of DNA Vaccine in Mice

An immunotherapeutic DNA vaccine containing DNA plasmids encoding an HBV core antigen or HBV polymerase antigen was tested in mice. The purpose of the study was designed to detect T-cell responses induced by the vaccine after intramuscular delivery via electroporation into BALB/c mice. Initial immunogenicity studies focused on determining the cellular immune responses that would be elicited by the introduced HBV antigens.

Figure 3A:
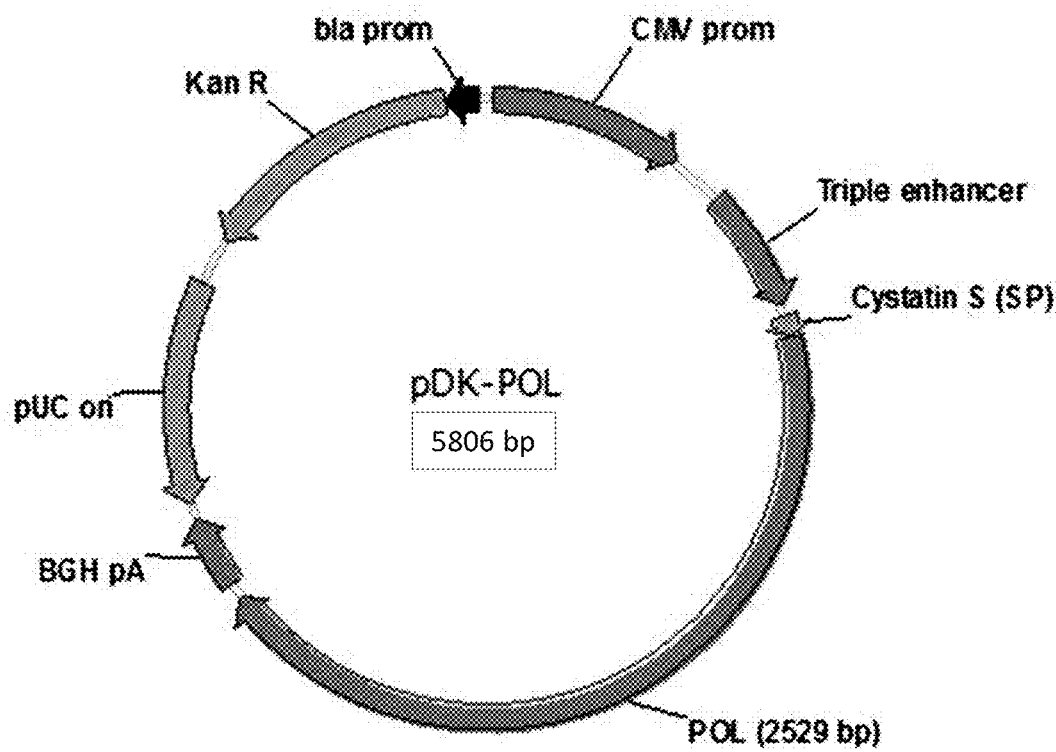
FIGS. 3A-3B show schematic representations of DNA plasmids according to embodiments of the application.
Figure 3B:
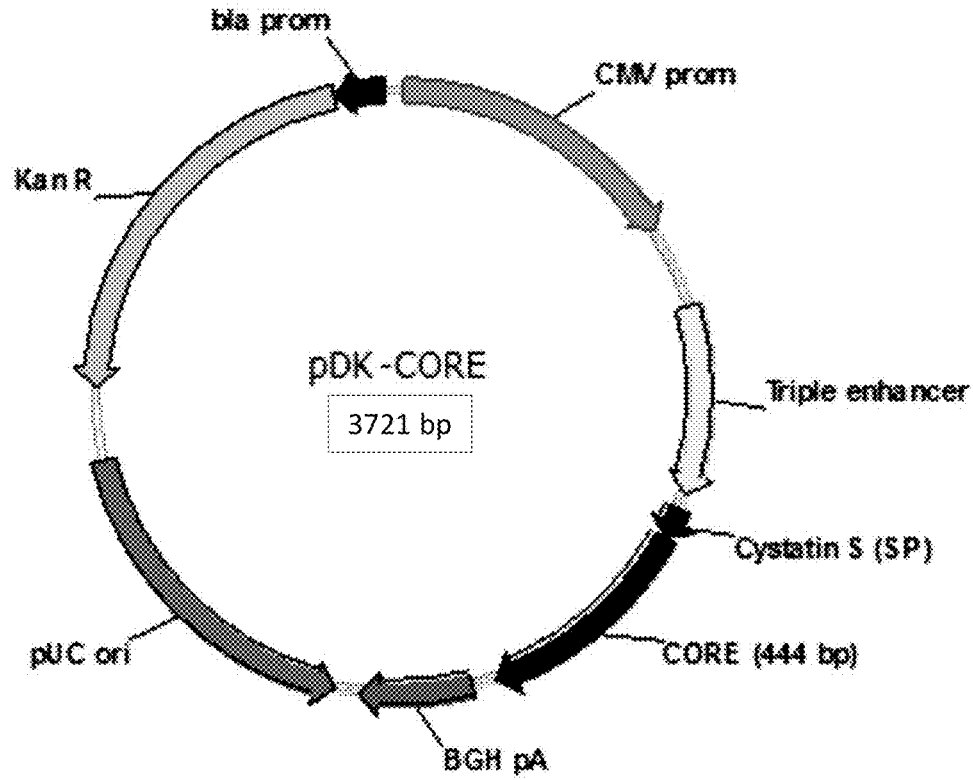

In particular, the plasmids tested included a pDK-Pol plasmid and pDK-Core plasmid, as shown in FIGS. 3A and 3B, respectively, and as described above in Example 1. The pDK-Pol plasmid encoded a polymerase antigen having the amino acid sequence of SEQ ID NO: 4, and the pDK-Core plasmid encoding a Core antigen having the amino acid sequence of SEQ ID NO: 2. First, T-cell responses induced by each plasmid individually were tested. The DNA plasmid (pDNA) vaccine was intramuscularly delivered via electroporation to Balb/c mice using a commercially available TriGrid™ delivery system-intramuscular (TDS-IM) adapted for application in the mouse model in cranialis tibialis. See International Patent Application Publication WO2017172838, and U.S. Patent Application Publication US20190184010 entitled "Method and Apparatus for the Delivery of Hepatitis B Virus (HBV) Vaccines," filed on the same day as this application for additional description on methods and devices for intramuscular delivery of DNA to mice by electroporation, the disclosures of which are hereby incorporated by reference in their entireties. In particular, the TDS-IM array of a TDS-IM v1.0 device having an electrode array with a 2.5 mm spacing between the electrodes and an electrode diameter of 0.030 inch was inserted percutaneously into the selected muscle, with a conductive length of 3.2 mm and an effective penetration depth of 3.2 mm, and with the major axis of the diamond configuration of the electrodes oriented in parallel with the muscle fibers. Following electrode insertion, the injection was initiated to distribute DNA (e.g., 0.020 ml) in the muscle. Following completion of the IM injection, a 250 V/cm electrical field (applied voltage of 59.4-65.6 V, applied current limits of less than 4 A, 0.16 A/sec) was locally applied for a total duration of about 400 ms at a 10% duty cycle (i.e., voltage is actively applied for a total of about 40 ms of the about 400 ms duration) with 6 total pulses. Once the electroporation procedure was completed, the TriGrid™ array was removed and the animals were recovered. High-dose (20 μg) administration to BALB/c mice was performed as summarized in Table 1. Six mice were administered plasmid DNA encoding the HBV core antigen (pDK-core; Group 1), six mice were administered plasmid DNA encoding the HBV pol antigen (pDK-pol; Group 2), and two mice received empty vector as the negative control. Animals received two DNA immunizations two weeks apart and splenocytes were collected one week after the last immunization.

TABLE 1

Mouse immunization experimental design of the pilot study.

| Group | N | pDNA | Unilateral Admin Site (alternate sides) | Dose | Vol | Admin Days | Endpoint (spleen harvest) Day |
|---|---|---|---|---|---|---|---|
| 1 | 6 | Core | CT + EP | 20 μg | 20 μL | 0, 14 | 21 |
| 2 | 6 | Pol | CT + EP | 20 μg | 20 μL | 0, 14 | 21 |
| 3 | 2 | Empty Vector (neg control) | CT + EP | 20 μg | 20 μL | 0, 14 | 21 |

CT, cranialis tibialis muscle; EP, electroporation.

Antigen-specific responses were analyzed and quantified by IFN-γ enzyme-linked immunospot (ELISPOT). In this assay, isolated splenocytes of immunized animals were incubated overnight with peptide pools covering the Core protein, the Pol protein, or the small peptide leader and junction sequence (2 μg/ml of each peptide). These pools consisted of 15 mer peptides that overlap by 11 residues matching the Genotypes BCD consensus sequence of the Core and Pol vaccine vectors. The large 94 kDa HBV Pol protein was split in the middle into two peptide pools. Antigen-specific T cells were stimulated with the homologous peptide pools and IFN-γ-positive T cells were assessed using the ELISPOT assay. IFN-γ release by a single antigen-specific T cell was visualized by appropriate antibodies and subsequent chromogenic detection as a colored spot on the microplate referred to as spot-forming cell (SFC).

Figure 4:
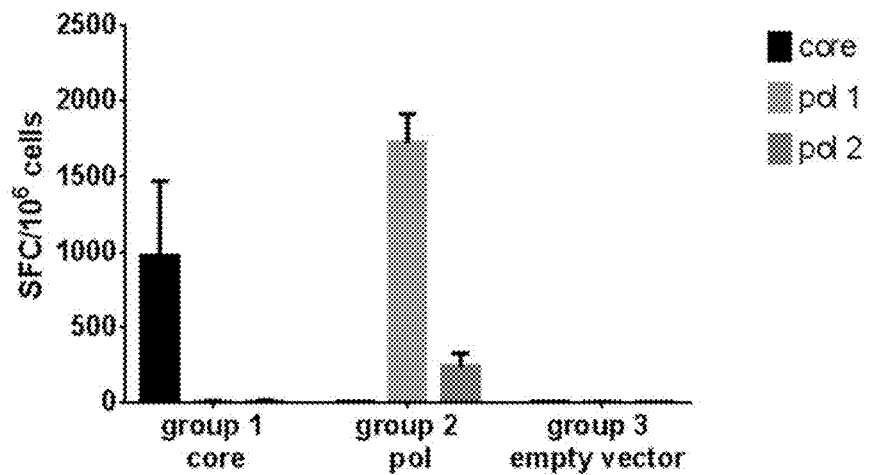
FIG. 4 shows ELISPOT responses of Balb/c mice immunized with different DNA plasmids expressing HBV core antigen or HBV pol antigen, as described in Example 2; peptide pools used to stimulate splenocytes isolated from the various vaccinated animal groups are indicated in gray scale; the number of responsive T-cells are indicated on the y-axis expressed as spot forming cells (SFC) per $10^6$ splenocytes.

Substantial T-cell responses against HBV Core were achieved in mice immunized with the DNA vaccine plasmid pDK-Core (Group 1) reaching 1,000 SFCs per $10^6$ cells (FIG. 4). Pol T-cell responses towards the Pol 1 peptide pool were strong (1,000 SFCs per $10^6$ cells). The weak Pol-2-directed anti-Pol cellular responses were likely due to the limited MHC diversity in mice, a phenomenon called T-cell immunodominance defined as unequal recognition of different epitopes from one antigen. A confirmatory study was performed confirming the results obtained in this study (data not shown).

The above results demonstrate that vaccination with a DNA plasmid vaccine encoding HBV antigens induces cellular immune responses against the administered HBV antigens.

Example 4: Dose-Finding Study of Combined pDK-Core/pDK-Pol Plasmids in Mice

The purpose of this dose-finding study with combined plasmids was to evaluate the immune responses in mice of a mixture of DNA plasmid (pDNA) vectors encoding HBV core and pol antigens applied in one site using different DNA doses. In this study, an immunotherapeutic DNA vaccine containing a 1:1 (w/v) mixture of two plasmids, the pDK-pol and pDK-core plasmids described in Example 1, was tested in mice. The DNA vaccine was delivered to Balb/c mice in one anatomic site intramuscularly via electroporation as described above in Example 3. Vaccination of the combined Core- and Pot-expressing plasmids at 10 μg, 1 μg, and 0.1 μg DNA of each plasmid per site was performed as summarized in Table 2. Eight mice were tested in each group, and two mice were administered empty vector as the negative control. Animals received two DNA immunizations three weeks apart and splenocytes were collected one week after the last immunization.

TABLE 2

Mouse immunization experimental design of the dose-finding study with combined plasmids.

| Group | N | pDNA | Unilateral admin site (alternate sides) | Dose of each pDNA per site | Dose total pDNA per site | Admin days | Endpoint (spleen harvest) Day |
|---|---|---|---|---|---|---|---|
| 1 | 8 | Core and Pol | CT + EP | 10 μg | 20 μg | 0, 21 | 28 |
| 2 | 8 | Core and Pol | CT + EP | 1 μg | 2 μg | 0, 21 | 28 |
| 3 | 8 | Core and Pol | CT + EP | 0.1 μg | 0.2 μg | 0, 21 | 28 |
| 4 | 2 | Empty Vector (neg. control) | CT + EP | 20 μg | 20 μg | 0, 21 | 28 | pDNA, plasmid DNA; CT, cranialis tibialis muscle; EP, electroporation.

Figure 5:
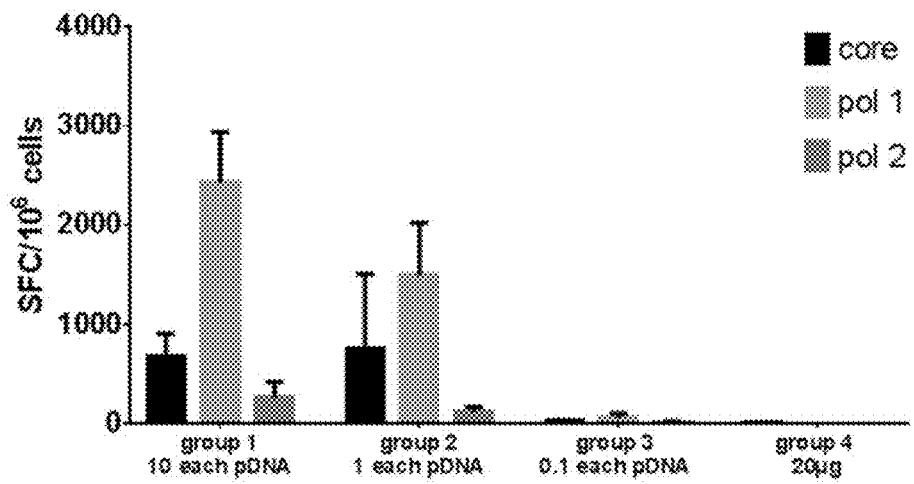
FIG. 5 shows ELISPOT responses of Balb/C mice immunized with a combination of DNA plasmids expressing HBV core antigen and HBV pol antigen according to the dose-finding study described in Example 3; peptide pools used to stimulate splenocytes isolated from the various vaccinated animal groups are indicated in gray scale; the number of responsive T-cells are indicated on the y-axis expressed as spot forming cells (SFC) per $10^6$ splenocytes.

Antigen-specific responses were analyzed and quantified by IFN-γ enzyme-linked immunospot (ELISPOT) as described in Example 1. Considerable T-cell responses against Core and Pol were achieved in BALB/c mice immunized with the combined DNA vaccine consisting of plasmid pDK-Core and pDK-Pol (FIG. 5). There was no statistical difference in terms of the magnitude of immune responses between Group 1, immunized with 10 µg of each plasmid, and Group 2, immunized with only 1 µg of each plasmid. This result suggested that T-cell responses reached a maximum level at around 1 µg Core- and Pol-antigen-expressing plasmids. However, at 10-fold lower DNA exposure, i.e., at 0.1 µg of each plasmid, a significant decrease in SFCs was observed. Pol T-cell responses towards the Pol 1 peptide pool were dominant. The weak Pol-2-directed anti-Pol cellular responses were likely due to the limited MHC diversity in inbred mice, a phenomenon called T-cell immunodominance defined as unequal recognition of different epitopes from one antigen.

The above results demonstrate that in mice immunized with a combination of DNA plasmids expressing HBV core and pol antigens, considerable T-cell responses were found at doses of 1 µg of each plasmid, and some immune response was still observed at a dose 0.1 per plasmid.

Example 5: Immune Interference Study in Mice

For practical reasons, it would be desirable to develop the combination HBV core and pol antigen DNA vaccine as a combined (mixed) vector formulation. However, immunodominance might occur with multivalent vaccines and immune responses against subdominant antigens could be blunted. Therefore, immune interference, i.e., decreased Core- and/or Pol-specific cellular responses from administration of a combination of the two antigen-expression plasmids mixed together when compared to immunization of either vector in different anatomic sites, was assessed.

Balb/c mice were vaccinated with the pDK-core and/or pDK-pol DNA plasmids intramuscularly via electroporation as described in Example 3. The DNA plasmids (pDNA) were administered at a dose of 5 µg per site applied either individually, combined (mixed) at one site, or combined in separate sites, as summarized in Table 3. Animals received two DNA immunizations three weeks apart and splenocytes were collected one week after the last immunization.

TABLE 3

Mouse immunization experimental design of the immune interference study.

| Group | N | pDNA | Unilateral admin site (alternate sides) | Dose each pDNA per site | Dose total pDNA per site | Admin days | Endpoint (spleen harvest) Day |
|---|---|---|---|---|---|---|---|
| 1 | 6 | Core | Bilateral CT | 5 µg | 10 µg | 0, 21 | 28 |
| 2 | 6 | Pol | Bilateral CT | 5 µg | 10 µg | 0, 21 | 28 |
| 3 | 6 | Core and Pol mixed | Bilateral CT | 10 µg | 20 µg | 0, 21 | 28 |
| 4 | 6 | Core and Pol individual | Core in left CT Pol in right CT | 10 µg | 20 µg | 0, 21 | 28 |
| 5 | 2 | Empty Vector (neg. control) | Bilateral CT | 10 µg | 20 µg | 0, 21 | 28 |

CT, cranialis tibialis muscle.

Figure 6:
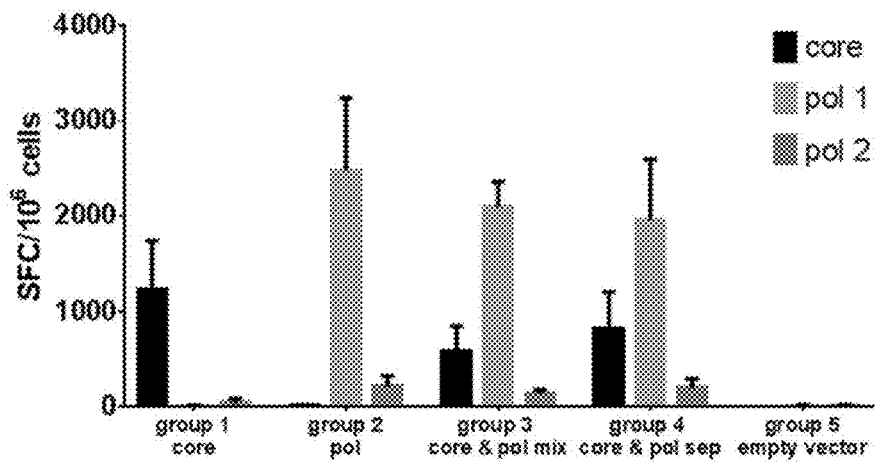
FIG. 6 shows ELISPOT responses of Balb/c mice immunized with DNA plasmids (pDNA) expressing HBV core antigen and HBV pol antigen according to the immune interference study as described in Example 4; Group 1, single Core pDNA; Group 2, single Pol pDNA; Group 3, mixed Core and Pol pDNA; Group 4, Core and Pol pDNA applied separately at different sites; peptide pools used to stimulate splenocytes isolated from the various vaccinated animal groups are indicated in gray scale; the number of responsive T-cells are indicated on the y-axis expressed as spot forming cells (SFC) per $10^6$ splenocytes.

Antigen-specific responses were analyzed and quantified by IFN-γ enzyme-linked immunospot (ELISPOT) as described in Example 1. Strong Core- and Pol-specific antigen responses were confirmed in BALB/c mice in this experiment (FIG. 6). No significant immune interference was observed based on the substantially identical T-cell responses obtained for Group 3, in which both plasmids were mixed and applied in the same site, and Group 4, in which pDNA expressing core and pol antigens were individually electroporated in two different sites. One animal in Group 1 showed a low abnormal Pol-2-pool-directed response. The same experiment was repeated in C57/Bl6 mice with comparable results.

The above results demonstrate that substantially no immune interference was observed when combining the two HBV antigen-expression plasmids pDK-Core and pDK-Pol.

Example 6: Evaluation of the Efficacy of a DNA Vaccine in Non-Human Primates

The purpose of this study was to evaluate the efficacy of a therapeutic HBV DNA vaccine delivered intramuscularly with electroporation, and to induce and measure a HBV-specific T cell response/cell activation in Cynomolgus monkeys (*Macaca fascicularis*).

Vaccine

The vaccine used in this study was a combination of two separate DNA plasmids encoding an HBV core antigen and HBV polymerase antigen, respectively. In particular, the DNA plasmids were pDK-Pol plasmid (encoding an HBV polymerase antigen having the amino acid sequence of SEQ ID NO: 4) and pDK-Core plasmid (encoding an HBV core antigen having the amino acid sequence of SEQ ID NO: 2), as shown in FIGS. 3A and 3B, respectively, and described in Example 1.

The DNA plasmids were administered in a 1:1 (w/w) mixture of both plasmids delivered in one anatomic site. Non-human Primates (NHP) were electroporated with a TriGrid™ delivery system-intramuscular (TDS-IM) adapted for application in the NHP model. See International Patent Application Publication WO2017172838, and U.S. Patent Application Publication US20190184010 entitled "Method and Apparatus for the Delivery of Hepatitis B Virus (HBV) Vaccines," filed on the same day as this application for additional description on methods and devices for intramuscular delivery of DNA to NHP by electroporation, the disclosures of which are hereby incorporated by reference in their entireties. In particular, the TDS-IM array of a TDS-IM v1.0 or TDS-IM v2.0 having an electrode array with a 6.0 mm spacing between the electrodes and an electrode diameter of 0.021 or 0.023 inch, respectively, was inserted percutaneously into the selected muscle with the major axis of the diamond configuration of the electrodes oriented in parallel with the muscle fibers. The conductive length was 5.0 mm for TDS-IM v1.0 or TDS-IM v2.0, while the effective penetration depth was 15.5 mm for TDS-IM v1.0 and 9.0 mm for TDS-IM v2.0. Following electrode insertion, the injection was initiated to distribute DNA (e.g., 1.0 ml) in the muscle. Following completion of the IM injection, a 250 V/cm electrical field (applied voltage of 142.4-157.6 V, applied current limits of 0.6-4 A, 0.16 A/sec) was locally applied for a total duration of about 400 ms at a 10% duty cycle (i.e., voltage is actively applied for a total of about 40 ms of the about 400 ms duration) with 6 total pulses. Once the electroporation procedure was completed, the TriGrid™ array was removed and the animals were recovered. The initial immunogenicity study focused on determining the cellular immune responses that would be elicited by the introduced HBV antigens.

Non-Human Primates

Cynomolgus macaques (n=30) were sourced from China (Covance Research Products Inc. USA), at 2.5 to 5 years of age and weighing 3.0 to 5.0 kg at start of study. They were socially housed in enriched environment according to veterinary guidelines and National Research Council, *Guide for the Care and Use of Laboratory Animals*, 8th Edition, Washington D.C.: National Academies Press (2011). Animals were acclimatized for a period of 2 weeks before starting the study. Monkeys were anesthetized with ketamine prior to each plasmid electroporation administration. Blood was collected 2 weeks after each immunization in vials containing sodium heparin. PBMCs were isolated using ficoll gradient and stored in liquid nitrogen tanks until analysis.

Intramuscular/Electroporation Administration in the Non-Human Primates

Plasmid administration was performed three times (group 1) at days 0, 36 and 62, as summarized in Table 4. pDK-Core (1.0 mg) and pDK-Pol (1.0 mg) were administered via electroporation with the delivery system set to 19 mm (short) injection depth in the quadriceps (vastus lateralis) muscle. For each injection, an alternate leg muscle was administered. The syringe containing DNA plasmid was equipped with an injection depth limiter suitable for NHP quadriceps muscle, for an injection target depth of about 10 mm into the muscle, with the major axis of the diamond configuration oriented in parallel with the muscle fibers. Immediately after the IM injection was completed, the electroporation apparatus was activated, resulting in the electrical stimulation of the muscle at an amplitude of up to 250 V per cm of electrode spacing for a total of up to 40 mS duration over a 400 mS interval. Samples were collected on days 0, 14, 50, and 76, and analyzed by ELISPOT and intracellular cytokine staining.

TABLE 4

NHP vaccination experimental design

| Group | N | pDNA | Unilateral admin site (alternate sides) | Dose each pDNA per site | Dose total pDNA per site | Admin days | Sample days |
|---|---|---|---|---|---|---|---|
| 1 | 5 | pDK-Core & pDK-Pol | CT + EP | 1.0 mg | 2.0 mg | 0, 36 and 62 | 0, 14, 50 and 76 |

ELISPOT Analysis

Figure 7A:
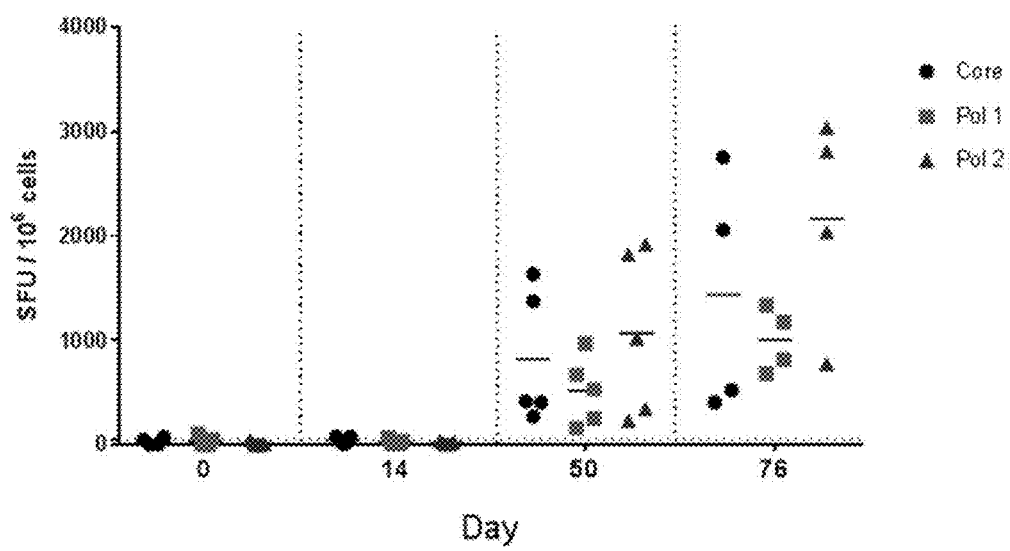
FIGS. 7A and 7B show the immunogenicity of a DNA vaccine according to an embodiment of the application in NHPs as described in Example 5.

Antigen-specific responses were analyzed and quantified by IFN-γ enzyme-linked immunospot (ELISPOT) using Primate IFN-γ ELISpot kit (R&D Systems, USA, Cat No. EL961). In this assay, isolated PBMCs of immunized animals were incubated in triplicate wells overnight with peptide pools (2 μg/ml) covering the Core protein and the Pol protein. These pools consist of 15 mer peptides that overlap by 11 residues matching the Genotypes ABCD consensus sequence of the Core and Pol vaccine vectors. The peptides were synthesized at 90% purity (JPT, Germany). The large 94 kDa HBV Pol protein was split in the middle into two peptide pools. IFN-γ release by a single antigen-specific T cell was visualized by appropriate antibodies and subsequent chromogenic detection as a colored spot on the microplate referred to as spot-forming cell (SFC). The results are shown in FIG. 7A.

Intracellular Cytokine Staining (ICS)

Figure 7B:
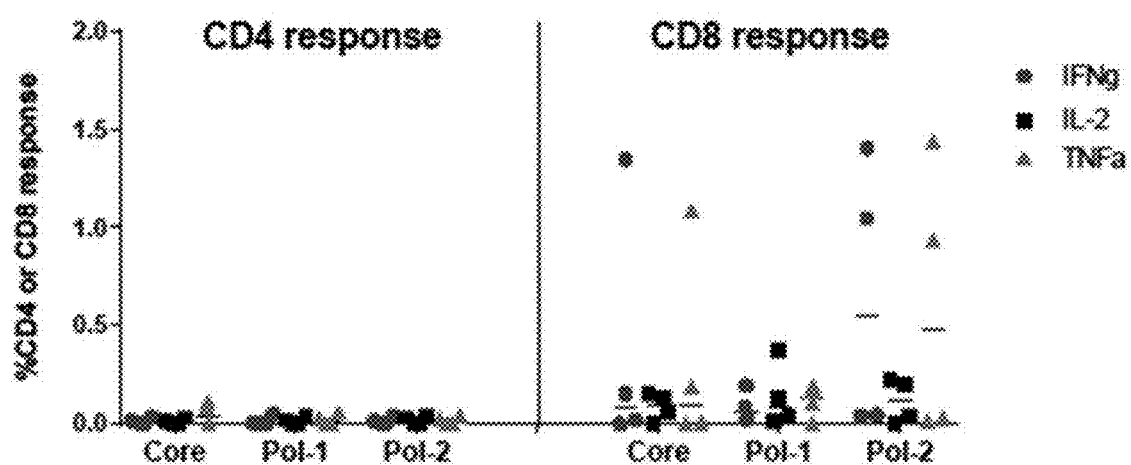

Intracellular cytokine staining (ICS) was used to study the vaccine-induced T-cell responses. Frozen PBMCs were thawed and rested overnight in 10% FBS, RPMI medium before stimulation with vaccine-insert matched Core, Pol-1 or Pol-2 peptide pools (2 ug/μl), DMSO or Leukocyte Activation cocktail for 6 hours in 10% FBS, RPMI medium containing Golgiplug Protein Transport Inhibitor (1 ug/μl). Stimulated cells were stained with fixable viability dye eFluor 780 (65-0865-14, eBioscience), and treated for 20 minutes with Fixation/Permeabilization solution (554714, BD Biosciences) before staining for 30 minutes with intracellular stain mix as shown in Table 5 below. Stained cells were acquired using Fortessa flowcytometer with the appropriate single color compensation controls. Response magnitudes were reported as the percentage of $CD4^+$ or $CD8^+$ T cells expressing IFN-γ, TNF-α or IL-2 after stimulation. The results are shown in FIG. 7B.

TABLE 5

Antibody panel used for intracellular cytokine staining assay

| BD Biosciences Cat no | Antibody | Fluorescence | Clone |
|---|---|---|---|
| 557705 | CD3 | Alexa fluor 488 | SP34 |
| 563823 | CD8 | BUV786 | RPA-T8 |
| 564107 | CD4 | BUV395 | L200 |
| 554701 | IFNg | PE | B27 |
| 554514 | TNF | APC | MAb11 |
| 564164 | IL-2 | BV421 | MQ1-17H12 |

Results

ELISPOT data (FIG. 7A) showed strong Core and Pol-2 responses after two immunizations. A third immunization greatly increased the IFN-γ magnitude. The Pol-1 peptide pool elicited an intermediate response that was also improved with a third immunization, although not as greatly improved as with Core and Pol-2. Day 76 data includes only the results from four NHPs, as blood draw from the fifth monkey was not successful. The high variation within each group is due to the NHPs being sourced from an outbred stock, and genetic diversity could account for the differing immune response.

The ICS assay data (FIG. 7B) showed that cytokine response from HBV peptide stimulation is CD8 driven and is specific to the Core and Pol-2 peptide pools, as previously observed with ELISPOT. The responding NHPs in the ICS assay are the same responding individuals as with the ELISPOT assay. Although a few individual ICS responses do not show positive as seen in the ELISPOT data, this may be attributed to the higher sensitivity of the ELISPOT assay.

Conclusion

The above results demonstrate that in NHPs immunized with a combination of pDK-Core and pDK-Pol vaccine by intramuscular injection via electroporation, considerable T-cell responses were found at doses of 1.0 mg of each plasmid, with peptide specific responses detected after two immunizations and even greater responses after three immunizations. At Day 76, ELISPOT assay results showed that peptide pools Core, Pol-1 and Pol-2 induced positive IFN-γ T cell responses in every tested NHP (4/5 NHP). The ICS assay on PBMCs from immunized NHPs show that the HBV peptide specific response is CD8 driven, with the highest responses against Core and Pol-2 peptide pools.

Example 7: Evaluation of the Efficacy of a DNA Vaccine in Human Subjects

The efficacy of a therapeutic HBV DNA vaccine delivered intramuscularly with electroporation is evaluated in human subjects.

Human Subjects

The human subjects are adult patients having chronic HBV infection that are HBsAg-positive. The human subjects are being treated with an HBV polymerase inhibitor (entecavir or tenofovir).

Vaccine

Human patients are administered a combination of two separate DNA plasmids encoding an HBV core antigen and HBV polymerase antigen, respectively. In particular, the DNA plasmids were pDK-Pol plasmid (encoding an HBV polymerase antigen having the amino acid sequence of SEQ ID NO: 4) and pDK-Core plasmid (encoding an HBV core antigen having the amino acid sequence of SEQ ID NO: 2), as shown in FIGS. 3A and 3B, respectively, and described in Example 1. The DNA plasmids are administered in a 1:1 mixture of both plasmids at different dosages, particularly dosages of 0.25 mg, 1 mg, and 6 mg of total plasmid according to a randomized, placebo-controlled escalating dose trial.

Intramuscular/Electroporation Administration in the Human Subjects

The DNA plasmids are administered to the human subjects by electroporation in 2 to 3 intramuscular immunizations using a TriGrid™ delivery system-intramuscular (TDS-IM) adapted for application in humans. Some patients are administered placebo (i.e., plasmids lacking the coding sequences for HBV antigens) as control. A TriGrid™ delivery system-intramuscular (TDS-IM) adapted for application in the human is used for the delivery of the plasmid DNA by electroporation. See International Patent Application Publication WO2017172838, and U.S. Patent Application Publication US20190184010 entitled "Method and Apparatus for the Delivery of Hepatitis B Virus (HBV) Vaccines," filed on the same day as this application for additional description on methods and devices for intramuscular delivery of DNA to humans by electroporation, the disclosures of which are hereby incorporated by reference in their entireties. For example, the TDS-IM array of TDS-IM v2.0 having an electrode array with a 6.0 mm spacing between the electrodes and an electrode diameter of 0.023 inch, respectively, can be inserted percutaneously into the selected muscle with the major axis of the diamond configuration of the electrodes oriented in parallel with the muscle fibers. The conductive length can be 5.0 mm, while the effective penetration depth can be 19 mm. Following electrode insertion, the injection is initiated to distribute DNA (e.g., 1.0 ml) in the muscle. Following completion of the IM injection, a 250 V/cm electrical field (applied voltage of 142.4-157.6 V, applied current limits of 0.6-4 A, 0.16 A/sec) is locally applied for a total duration of about 400 ms at a 10% duty cycle (i.e., voltage is actively applied for a total of about 40 ms of the about 400 ms duration) with 6 total pulses. Once the electroporation procedure is completed, the TriGrid™ array is removed and the human subject is recovered.

Blood samples are collected from the patients at various time points post-immunization. The development of HBsAg levels post immunization, particularly for levels consistent with evolution to clinical seroconversion are evaluated in the patients 3 to 6 months post-immunization. The persistent loss of HBsAg and a decrease in clinical disease (e.g., cirrhosis, hepatocellular carcinoma) are evaluated in the patients 6 to 12 months post-immunization.

Example 8: In Vivo Immunogenicity Study of Adenoviral Vectors in Mice

Figure 8A:
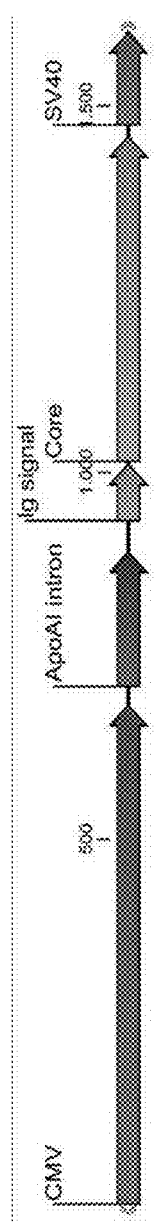
FIGS. 8A and 8B show the schematic representations of the expression cassettes in adenoviral vectors according to embodiments of the application.
Figure 8B:
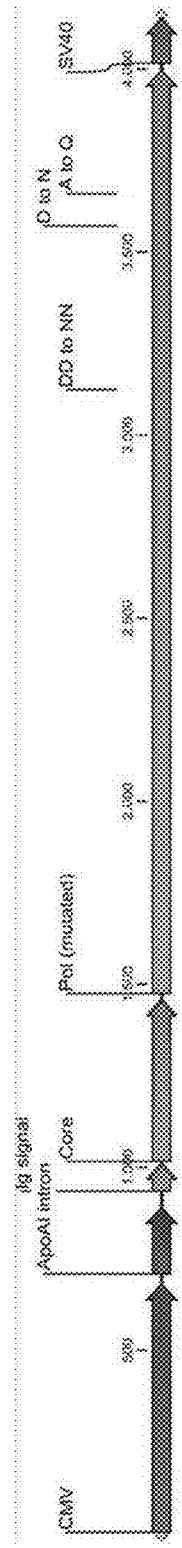

An immunotherapeutic vaccine containing adenoviral vectors encoding an HBV core antigen or an HBV polymerase antigen was tested in mice. The purpose of the study was to detect T-cell responses induced by the vaccine after intramuscular delivery into F1 mice (C57BL/6× Balb/C). Initial immunogenicity studies focused on determining the cellular immune responses that would be elicited by the introduced HBV antigens. In particular, the adenovectors tested contained the expression cassettes as shown in FIGS. 8A and 8B.

In vivo Immunogenicity Study

To evaluate the in vivo immunogenicity of the adenoviral vaccine, HBV adenoviral vectors were administered intramuscularly into F1 mice. These immunogenicity studies focused on determining the cellular immune responses elicited by the HBV antigens Core and Polymerase. The administration to F1 mice was performed as summarized in Table 6. Animals received one HBV adenoviral vector immunization. Splenocytes were collected nine weeks later.

TABLE 6

Experimental Design for Mouse Immunization with Adenoviral Vectors

| Group | N | Prime Day 0 | R | Dose (vp) | Endpt Day |
|---|---|---|---|---|---|
| 1 | 4 | Core Pol fusion + Core | IM | $10^8$ | 63 |
| 2 | 4 | Core Pol fusion + Core | IM | $10^9$ | 63 |
| 3 | 4 | Core Pol fusion + Core | IM | $10^{10}$ | 63 |
| 7 | 4 | Core Pol fusion | IM | $10^8$ | 63 |
| 8 | 4 | Core Pol fusion | IM | $10^9$ | 63 |
| 9 | 4 | Core Pol fusion | IM | $10^{10}$ | 63 |

IM: intramuscular;
vp: viral particles;

Evaluation of Immunogenicity of HBV Adenoviral Vectors

Antigen-specific responses were analyzed and quantified by IFN-γ enzyme-linked immunospot (ELISPOT). In this assay, isolated splenocytes of immunized animals were incubated with peptide pools covering the Core and the Pol protein (2 μg/ml of each peptide). The pools consist of 15-mer peptides that overlap by 11 residues matching the genotypes ABCD consensus sequences of the Core and Pol adenoviral vectors. The large 94 kDa HBV Pol protein was split in the middle into two peptide pools. In ELISPOT, IFN-γ release by a single antigen-specific T-cell was visualized by appropriate antibodies and subsequent chromogenic detection as a colored spot on the microplate referred to as spot-forming cell (SFC).

Figure 9:
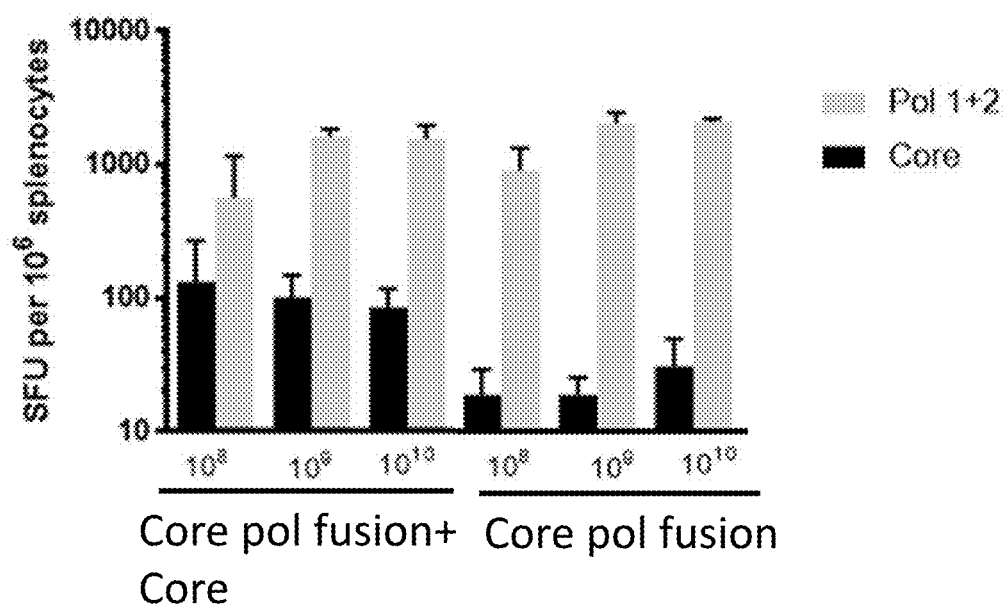
FIG. 9 shows ELISPOT responses in F1 mice (C57BL/6× Balb/C) immunized with HBV adenoviral vectors, as described in Example 8; HBV core or polymerase peptide pools used to stimulate splenocytes isolated from the various vaccinated animal groups are indicated in black (core) and grey (pol); Pol1 and pol2 responses were summed; the X-axis shows the adenovector dose and experimental groups. The number of responsive T-cells are indicated on the y-axis expressed as spot forming cells (SFC) per $10^6$ splenocytes.

The results are shown in FIG. 9. From the results, it can be seen that HBV adenoviral vectors, especially the combination of Core Pol fusion and Core adenovectors gave rise to Core and Pol specific T cell responses. These data indicate that adenoviral vectors encoding HBV core and pol antigens give rise to robust T cell responses against core and pol in F1 mice.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES

1. Cohen et al. "Is chronic hepatitis B being undertreated in the United States?" *J. Viral Hepat.* (2011) 18(6), 377-83.
2. Obeng-Adjei et al. "DNA vaccine cocktail expressing genotype A and C HBV surface and consensus core antigens generates robust cytotoxic and antibody responses and mice and Rhesus macaques" *Cancer Gene Therapy* (2013) 20, 652-662.
3. World Health Organization, Hepatitis B: Fact sheet No. 204 [Internet] 2015 March. Available from http://www.who.nt/mediacentre/factsheets/fs204/en/.
4. Belloni et al. "IFN-α inhibits HBV transcription and replication in cell culture and in humanized mice by targeting the epigenetic regulation of the nuclear cccDNA minichromosome" *J. Clin. Invest.* (2012) 122(2), 529-537.
5. Michel et al. "Therapeutic vaccines and immune-based therapies for the treatment of chronic hepatitis B: perspectives and challenges." *J. Hepatol.* (2011) 54(6), 1286-1296.

We claim:

1. An RNA replicon comprising a nucleic acid molecule encoding an HBV polymerase antigen comprising the amino acid sequence of SEQ ID NO: 4, wherein the HBV polymerase antigen does not have reverse transcriptase activity and RNase H activity.

2. The RNA replicon of claim 1, wherein the nucleic acid molecule further encodes a truncated HBV core antigen consisting of the amino acid sequence of SEQ ID NO: 2 or SEQ ID NO: 14.

3. The RNA replicon of claim 1, wherein the nucleic acid molecule encoding the HBV polymerase antigen comprises the polynucleotide sequence of SEQ ID NO: 3 or SEQ ID NO: 16.

4. The RNA replicon of claim 2, wherein the nucleic acid molecule encoding the HBV core antigen comprises the polynucleotide sequence of SEQ ID NO: 1 or SEQ ID NO: 15.

5. The RNA replicon of claim 1, further comprising a polynucleotide sequence encoding a signal sequence operably linked to the HBV antigen.

6. The RNA replicon of claim 5, wherein the signal sequence has the amino acid sequence of SEQ ID NO: 6 or SEQ ID NO: 19.

7. The RNA replicon of claim 1, wherein the RNA replicon is derived from a virus belonging to the alphavirus family.

8. The RNA replicon of claim 2, wherein the RNA replicon is a bicistronic expression vector.

9. The RNA replicon of claim 8, wherein the RNA replicon further comprises a ribosomal slippage site between the nucleic acid molecules encoding the HBV polymerase and HBV core polynucleotide sequences.

10. The RNA replicon of claim 9, wherein the ribosomal slippage site is a FA2 slippage site derived from foot-and-mouth disease virus (FMDV).

11. A method of inducing an immune response against a hepatitis B virus in a subject in need thereof, the method comprising administering to the subject the RNA replicon of claim 1.

12. A method of treating a viral infection comprising a hepatitis B virus (HBV) infection in a subject in need thereof, the method comprising administering to the subject the RNA replicon of claim 1.

13. The method of claim 12, wherein the HBV infection comprises a chronic HBV infection.

14. A method of treating a hepatitis B virus (HBV) infection in a subject in need thereof, the method comprising administering to the subject the RNA replicon of claim 1.

15. A composition comprising the RNA replicon of claim 1 and a pharmaceutically acceptable carrier comprising a lipid nanoparticle.

16. A pharmaceutical composition comprising:
   (1) an RNA replicon comprising:
      (a) a polynucleotide sequence encoding an HBV polymerase antigen comprising an amino acid sequence at least 98% identical to SEQ ID NO: 4, wherein the HBV polymerase antigen does not have reverse transcriptase activity and RNase H activity;
   and
   (2) a pharmaceutically acceptable carrier comprising a lipid nanoparticle.

17. The pharmaceutical composition of claim 16, wherein the RNA replicon further comprises:
   (b) a polynucleotide sequence encoding a truncated HBV core antigen consisting of the amino acid sequence of SEQ ID NO: 2 or SEQ ID NO: 14; and
   (c) a ribosomal slippage site between the polynucleotide sequences encoding the HBV polymerase and HBV core antigens; and
   (d) a polynucleotide sequence encoding a signal sequence operably linked to at least one of the HBV polymerase antigen and the truncated HBV core antigen,
   wherein the RNA replicon is a bicistronic expression vector that expresses individual HBV polymerase and HBV core antigens.

18. The pharmaceutical composition of claim 17, wherein the signal sequence has the amino acid sequence of SEQ ID NO: 6 or SEQ ID NO: 19.

19. A method of inducing an immune response against a hepatitis B virus in a subject in need thereof, the method comprising administering to the subject the pharmaceutical composition of claim 16.

20. A method of treating a viral infection comprising a hepatitis B virus (HBV) infection in a subject in need thereof, the method comprising administering to the subject the pharmaceutical composition of claim 16.

21. The method of claim 20, wherein the HBV infection comprises a chronic HBV infection.

22. A method of treating a hepatitis B virus (HBV) infection in a subject in need thereof, the method comprising administering to the subject the pharmaceutical composition of claim 16.

23. A pharmaceutical composition comprising a combination of:
   (a) a first RNA replicon encoding an HBV polymerase antigen comprising an amino acid sequence at least 98% identical to SEQ ID NO: 4, wherein the HBV polymerase antigen does not have reverse transcriptase activity and RNase H activity;

(b) a second RNA replicon encoding a truncated HBV core antigen consisting of an amino acid sequence at least 97% identical to SEQ ID NO: 2 or SEQ ID NO: 14; and (c) a pharmaceutically acceptable carrier comprising a lipid nanoparticle.

24. The pharmaceutical composition of claim 23, wherein at least one of the first and second RNA replicons further comprises a polynucleotide sequence encoding a signal sequence operably linked to the HBV antigen.

25. The RNA replicon of claim 24, wherein the signal sequence has the amino acid sequence of SEQ ID NO: 6 or SEQ ID NO: 19.

* * * * *